US008173361B2

(12) United States Patent
Vacanti et al.

(10) Patent No.: US 8,173,361 B2
(45) Date of Patent: May 8, 2012

(54) METHOD OF DETERMINING METABOLISM OF A TEST AGENT

(75) Inventors: Joseph P. Vacanti, Winchester, MA (US); Robert Rubin, Brookline, MA (US); Wing Cheung, Swampscott, MA (US); Jeffrey T. Borenstein, Newton, MA (US)

(73) Assignees: The General Hospital Corporation, Boston, MA (US); The Charles Stark Draper Laboratory, Cambridge, MA (US)

( * ) Notice: Subject to any disclaimer, the term of this patent is extended or adjusted under 35 U.S.C. 154(b) by 0 days.

(21) Appl. No.: 12/707,469

(22) Filed: Feb. 17, 2010

(65) Prior Publication Data

US 2011/0008765 A1   Jan. 13, 2011

Related U.S. Application Data

(60) Division of application No. 11/183,115, filed on Jul. 15, 2005, now Pat. No. 7,670,797, which is a continuation-in-part of application No. PCT/US2004/001098, filed on Jan. 16, 2004.

(60) Provisional application No. 60/440,539, filed on Jan. 16, 2003.

(51) Int. Cl.
C12Q 1/00 (2006.01)

(52) U.S. Cl. .......................................................... 435/4
(58) Field of Classification Search ........................ 435/4
See application file for complete search history.

(56) References Cited

U.S. PATENT DOCUMENTS

| 3,684,097 | A | 8/1972 | Mathewson, Jr. et al. |
| 3,839,204 | A | 10/1974 | Ingenito et al. |
| 3,892,533 | A | 7/1975 | Freedman et al. |
| 3,907,687 | A | 9/1975 | Hoeltzenbein |
| 3,927,981 | A | 12/1975 | Viannay et al. |
| 3,977,976 | A | 8/1976 | Spaan et al. |
| 4,008,047 | A | 2/1977 | Petersen |
| 4,176,069 | A | 11/1979 | Metz et al. |
| 4,191,182 | A | 3/1980 | Popovich et al. |
| 4,229,290 | A | 10/1980 | Raj |
| 4,636,310 | A | 1/1987 | Bellhouse |
| 4,666,668 | A | 5/1987 | Lidorenko et al. |
| 5,034,188 | A | 7/1991 | Nakanishi et al. |
| 5,061,620 | A | 10/1991 | Tsukamoto et al. |
| 5,110,548 | A | 5/1992 | Montevecchi |
| 5,204,055 | A | 4/1993 | Sachs et al. |
| 5,222,982 | A | 6/1993 | Ommaya |
| 5,225,161 | A | 7/1993 | Mathewson et al. |
| 5,263,924 | A | 11/1993 | Mathewson |
| 5,266,480 | A | 11/1993 | Naughton et al. |
| 5,316,724 | A | 5/1994 | Mathewson et al. |
| 5,443,950 | A | 8/1995 | Naughton et al. |
| 5,486,359 | A | 1/1996 | Caplan et al. |
| 5,518,680 | A | 5/1996 | Cima et al. |
| 5,601,727 | A | 2/1997 | Bormann et al. |
| 5,626,759 | A | 5/1997 | Krantz et al. |
| 5,665,596 | A | 9/1997 | Mussi |
| 5,686,289 | A | 11/1997 | Humes et al. |
| 5,695,717 | A | 12/1997 | Polaschegg et al. |
| 5,785,964 | A | 7/1998 | Naughton et al. |
| 5,843,780 | A | 12/1998 | Thomson |
| 5,849,553 | A | 12/1998 | Anderson et al. |
| 5,885,829 | A | 3/1999 | Mooney et al. |
| 5,888,248 | A | 3/1999 | Berg et al. |
| 5,906,828 | A | 5/1999 | Cima et al. |
| 6,045,818 | A | 4/2000 | Cima et al. |
| 6,107,043 | A | 8/2000 | Jauregui et al. |
| 6,136,212 | A | 10/2000 | Mastrangelo et al. |
| 6,139,574 | A | 10/2000 | Vacanti et al. |
| 6,143,293 | A | 11/2000 | Weiss et al. |
| 6,165,486 | A | 12/2000 | Marra et al. |
| 6,183,781 | B1 | 2/2001 | Burke |
| 6,197,575 | B1 | 3/2001 | Griffith et al. |
| 6,200,802 | B1 | 3/2001 | Greene et al. |
| 6,228,607 | B1 | 5/2001 | Kersten et al. |
| 6,245,566 | B1 | 6/2001 | Gearhart et al. |
| 6,287,558 | B1 | 9/2001 | Lanza et al. |
| 6,372,482 | B1 | 4/2002 | Mitrani et al. |
| 6,376,169 | B1 | 4/2002 | Adams et al. |
| 6,455,311 | B1 | 9/2002 | Vacanti |

(Continued)

FOREIGN PATENT DOCUMENTS

EP    0836453 A1    4/1998

(Continued)

OTHER PUBLICATIONS

Jaeger, Introduction to Microelectronic Fabrication, Addison-Wesley Pub. Co., Reading, MA 1988.
U.S. Appl. No. 10/187,247, filed Jun. 28, 2002, Vacanti et al.
Supplementary European Search Report, Mar. 13, 2007, WO.
International Search Report in PCT/US04/0198, Sep. 8, 2004, WO.
Written Opinion in PCT/US04/01098, Sep. 8, 2004, WO.
International Search Report in PCT/US00/11407, Dec. 6, 2000, WO.
Written Opinion in PCT/US00/11407, Apr. 9, 2001, WO.
Supplemental European Search Report in EP 03 71 8019, Jul. 11, 2007, WO.

(Continued)

*Primary Examiner* — Ralph Gitomer
(74) *Attorney, Agent, or Firm* — Edwards Wildman Palmer LLP; Peter C. Lauro, Esq.; George N. Chaclas, Esq.

(57) ABSTRACT

A method for detecting one or more metabolites of a test agent in a tissue including: A) incubating a test agent and an enzyme within a three-dimensional structure comprising a first mold or polymer scaffold, a semi-permeable membrane, and a second mold or polymer scaffold, wherein the semi-permeable membrane is disposed between the first and second molds or polymer scaffolds, and wherein the first mold or polymer scaffold has microchannels that form a fluidic branching network that mimics the forces and transport of natural vasculatures and wherein the second mold or polymer scaffold comprises cells; B) forming an enzyme-substrate complex between the enzyme and the test agent; and C) detecting one or more metabolites of the test agent.

19 Claims, 47 Drawing Sheets

U.S. PATENT DOCUMENTS

| | | | |
|---|---|---|---|
| 6,458,275 | B1 | 10/2002 | Shukla et al. |
| 6,479,064 | B1 | 11/2002 | Atala |
| 6,479,072 | B1 | 11/2002 | Morgan et al. |
| 6,525,242 | B1 | 2/2003 | Wu et al. |
| 6,542,858 | B1 | 4/2003 | Grass et al. |
| 6,547,994 | B1 | 4/2003 | Monkhouse et al. |
| 6,573,063 | B2 | 6/2003 | Hochman |
| 6,607,910 | B1 | 8/2003 | Dimitrijevich et al. |
| 6,645,715 | B1 | 11/2003 | Griffith et al. |
| 6,647,358 | B2 | 11/2003 | Grass et al. |
| 6,942,873 | B2 | 9/2005 | Russell et al. |
| 7,670,797 | B2 * | 3/2010 | Vacanti et al. ............ 435/30 |
| 2001/0041964 | A1 | 11/2001 | Grass et al. |
| 2002/0010550 | A1 | 1/2002 | Grass et al. |
| 2002/0013662 | A1 | 1/2002 | Grass et al. |
| 2002/0035459 | A1 | 3/2002 | Grass et al. |
| 2002/0055092 | A1 | 5/2002 | Hochman |
| 2002/0061540 | A1 | 5/2002 | Grass et al. |
| 2002/0090725 | A1 | 7/2002 | Simpson et al. |
| 2002/0160471 | A1 | 10/2002 | Kisiday et al. |
| 2002/0173033 | A1 * | 11/2002 | Hammerick et al. ...... 435/305.2 |
| 2002/0182241 | A1 | 12/2002 | Borenstein et al. |
| 2003/0113708 | A1 | 6/2003 | Flint et al. |
| 2003/0121594 | A1 | 7/2003 | Brill |
| 2003/0124099 | A1 | 7/2003 | Atala |
| 2003/0125252 | A1 | 7/2003 | Underhill et al. |
| 2003/0129736 | A1 | 7/2003 | Mitrani |
| 2003/0173965 | A1 | 9/2003 | Oesingmann |
| 2003/0215941 | A1 | 11/2003 | Campbell et al. |
| 2004/0057869 | A1 | 3/2004 | Dingley |
| 2004/0084370 | A1 | 5/2004 | Singh et al. |
| 2004/0147016 | A1 | 7/2004 | Rowley et al. |
| 2005/0136545 | A1 * | 6/2005 | Schmid et al. ............. 436/45 |
| 2005/0169962 | A1 | 8/2005 | Bhatia et al. |
| 2005/0202557 | A1 | 9/2005 | Vacanti et al. |
| 2005/0260745 | A1 * | 11/2005 | Domansky et al. ....... 435/294.1 |
| 2010/0240086 | A1 * | 9/2010 | Kashanin et al. ............ 435/29 |

FOREIGN PATENT DOCUMENTS

| | | |
|---|---|---|
| WO | WO 96/09423 | 3/1996 |
| WO | WO 96/40002 | 12/1996 |
| WO | WO-9640002 | 12/1996 |
| WO | WO-9809582 | 3/1998 |
| WO | WO-9952356 | 10/1999 |
| WO | WO-0038758 | 7/2000 |
| WO | WO-00/66036 | 11/2000 |
| WO | WO 01/11011 | 2/2001 |
| WO | WO-0238735 | 5/2002 |
| WO | WO-02076529 | 10/2002 |
| WO | WO 03/061585 A3 | 7/2003 |
| WO | PCT/US03/29880 | 9/2003 |
| WO | 2004065616 A2 | 8/2004 |

OTHER PUBLICATIONS

Folch, et al; "Cellular micropatterns on biocompatible materials", Biotechnology Progress, vol. 14, No. 3, May 1998. pp. 388-392.

Den Braber, et al, "Orientation of ECM protein deposition, fibroblast cytoskeleton, and attachment complex components on silicone microgrooved surfaces", Journal of Biomedical Materials Research, vol. 40, No. 2, May 1998, pp. 291-300.

O. Schueller, et al., *Fabrication and Characterization of Glassy Carbon MEMS*," Chem. Mater., 1997, vol. 9, pp. 1399-1406.

N. Patel, et al., *Spatially contolled cell engineering on biodegradable polymer surfaces*, The FASB Journal, vol. 12, Nov. 1998, pp. 1448-1454.

S. Huang, et al., "Control of Cyclin D1, p27Kip1, and Cell Cycle Progression in Human Capillary Endothelial Cells by Cell Shape and Cytoskeletal Tension," Molecular Biology of the Cell, Nov. 1998, vol. 9, pp. 3179-3193.

E. Delamarche, et al., "Patterned Delivery of Immunoglubulins to Surfaces Using Microfluidic Networks," Science, vol. 276, May 2, 1997, pp. 779-781.

C. Chen, et al., "*Geometric Control of Cell Life and Death*," Science, May 30, 1997, vol. 276, pp. 1425-1428.

Y. Xia, et al., "Micromolding of Polymers in Capillaries: Applications in Microfabrication," Chem. Mater., 1996, vol. 8, pp. 1558-1567.

E. Delamarche, et al., "Microfluidic Networks for Chemical Patterning of Substrates: Design and Application to Bioassays," J. Am. Chem. Soc., 1998, vol. 120, pp. 500-508.

A. Folch, et al., "Molding of Deep Polydimethylsiloxane Microstructures for Microfluidics and Biological Applications," Journal of Biomechanical Engineering, Feb. 1999, vol. 121, pp. 28-34.

K. Heselmeyer, et al., "Gain of Chromosome 3q defines the transition from severe dysplasia to invasive carcinoma of the uterine cervix," Proc. Natl. Acad. Sci. USA, vol. 93, Jan. 1996, pp. 479-484.

E. Kim, et al., "*Polymer microstructures formed by moulding in capillaries*," Nature, vol. 376, Aug. 17, 1995, pp. 581-584.

O. Schueller, et al., "Fabricaton of Glassy Carbon Microstructures by Pyrolisis of Microfabricated Polymeric Precursors," Adv. Mater., 1997, vol. 9, No. 6, pp. 477-480.

M. Trau, et al., "Microscopic patterning of orientated mesoscopic silica through guided growth," Nature, vol. 390, Dec. 1997, pp. 674-676.

M. Bailly, et al., "Regulation of Protrusion Shape and Adhesion to the Substratum during Chemotactic Responses of Mammalian Carcinoma Cells," Experimental Cell Research, vol. 241, (1998), pp. 285-299 (Article No. EX984031).

Thompson, et al; "A Novel Pulsatile, Laminar Flow Bioreactor for the Development of Tissue-Engineered Vascular Structures"; Tissue Engineering, vol. 8, No. 6, 2002, pp. 1083-1088.

Liu, et al; Characterization and Evaluation of Detoxification Functions or a Nontumorigenic Immortalized Porcine Hepatocyte Cell Line (HepLiu[1]); Cell Transplantation, vol. 8, 1999, pp. 219-232.

Griffith, et al; "In Vitro Organogenesis of Liver Tissue"; Bioartificial Organs, vol. 831 of the Annals of the New York Academy of Sciences, Dec. 31, 1997, pp. 382-397.

Ames, et al; "Methods for Detecting Carcinogens and Mutagens with the *Salmonella*/Mammalian-Micorsome Mutagenicity Test"; Mutation Research, 31 (1975), pp. 347-364.

Hoganson, David, et al., "Report on Tissue Engineered Liver Scaffold Development".

Rennie, J. Scientific American 280, 37 (1999).

Lysaght, et al., Tissue Eng 4(3), 231 (1998).

Amedee et al., Differentiation, 58:157-164 (1994).

Burke, et al., Ann Surg 194, 413 (1981).

Compton, et al., Laboratory Investigation 60, 600 (1989).

Marler, J. et al., "Transplantation of cells in matrices for tissue regeneration", Advanced Drug Delivery Reviews, vol. 33, pp. 165-182, 1998.

Bell, et al., Science 221, 1052 (1981).

Langer, et al., Science 260, 920 (1993).

Vacanti, et al., Materials Research Society 252, 367 (1992).

Vacanti, et al., Lancet 354, 32 (1999).

Parenteau, et al., Journal of Cellular Biochemistry 45, 24 (1991).

Parenteau, et al., Biotechnology and Bioengineering 52, 3 (1995).

Purdue, et al., J. Burn Care Rehab 18, 52 (1997).

Hansbrough and Franco, Clinical Plastic Surg 25, 407 (1998).

Kane, et al., Biomaterials 20, 2363 (1999).

Griffith, et al., Annals of Biomed. Eng., 26(1998).

Griffith, et al., Annals of Biomed. Eng., 831 (1997).

Folch, et al., Biotechnology Progress, 14, 388 (1998).

Eiselt, et al., Biotechnol. Prog. 14, 134 (1998).

Wang, et al., Nature Biotech 20, 602 (2002).

Runyan, et al., Semiconductor Integrated Circuit Processing Technology (Addison-Wesley Publishing Co., Reading, MA 1990); Proceedings of the IEEE Micro Elecro Mechanical Systems Conference 1987-1998.

Jansen, et al., The Black Silicon Method IV: The Fabrication of Three-Dimensional Structures in Silicon with IEEE Proceedings of Micro Electro Mechanical Systems Conference, pp. 88-93 (1995).

Frazier, et al., "Two dimensional metallic microelectrode arrays for extracellular stimulation and recording of neurons", IEEE Proceedings of the Micro Electro Mechanical Systems Conference, pp. 195-200 (1993).

Lehmann, "Porous Silicon—A New Material for MEMS", IEEE Proceedings of the Micro Electro Mechanical Systems Conference, pp. 1-6 (1996).

Laermer, et al., "Bosch Deep Silicon Etching: Improving Uniformity and Etch Rate for Advanced MEMS Applications", Micro Electro Mechanical Systems, Orlando, FL, USA, (Jan. 17-21, 1999).

Despont, et al., "High-Aspect-Ratio, Ultrathick, Negative-Tone Near-UV Photoresist for MEMS", Proc. of IEEE 10$^{th}$ Annual International Workshop on MEMS, Nagoya, Japan, pp. 518-522 (Jan. 26-30, 1997).

Henry, et al., "Micromachined Needles for the Transdermal Delivery of Drugs", Micro Electro Mechanical Systems, Heidelberg, Germany, pp. 494-498 (Jan. 26-29, 1998).

A.A. Ayon, et al., "Tailoring etch directionality in a deep reactive ion etching tool", J. Vac. Sci. Tech. B 18, 1412 (2000).

Sachs, et al., Manufacturing Review 5, 117-126 (1992).

Xu, et al. Nat. Biotechnol., 19, 971 (2001).

Keller, et al. (1999) Exp. Hematol. 27:777-787.

Marti, et al. (1995) Nature. 375: 322-325.

Prelle, et al. (2000) Biochem. Biophy. Res. Commun. 277:631-638.

Hardt, et al. (1985) Eur. J. Immunol. 15:472-478.

Huelsken, et al. (2001) Cell. 105:533-545.

Ji, et al. (2000) J. Bone Miner. Metab. 18:132-139.

Migliorati, et al. (1987) J. Immunol. 138:3618-3625.

Eghbali, et al. (1991) Proc. Natl. Acad. Sci. USA. 88:795-799.

Niijima, et al. (1995) J. Neurosci. 15:1180-1194.

Guo, et al. (1997) Dev. Biol. 184:61-69.

Ling, et al. (1998) Exp. Neurol. 149:411-423.

Lopez-Fernandez, et al. (2000) J. Biol. Chem. 275:21653-60.

Wang, et al. (1989) Leuk. Res. 13:1091-1097.

Lako, et al. (2001) Mech. Dev. 103:49-59.

Evans et al., (1981) Nature 292:154-156.

Matsui et al., (1991) Nature 353:750-2.

Thomson et al. (1995) Proc. Natl. Acad. Sci. USA 92:7844-8.

Thomson et al. (1998) Science 282:1145-1147.

Shamblott et al. (1998) Proc. Natl. Acad. Sci. USA 95:13726-31.

Mitaka, et al., Biochem Biophys Res Commun 214, 310 (1995).

Taneto, et al., Am Jpathol 148, 383 (1996).

Mitaka, et al., Hepatology 29, 111 (1999).

Teebken, et al., Eur J. Vasa Endovasc. Surg. 19, 381 (2000).

Ranucci, et al., Bionnaterials 21, 783 (2000).

Burg et al., J. Biomed. Mater. Res 51, 642 (2000).

Jo et al., SPIE 3877, 222 (1999).

Camporese, et al., IEEE Electron. Device Lett. EDL 2, 61(1981).

Block, et al., J. Cell Biol, 132, 1133 (1996).

Landry, et al., J. Cell Biol. 101, 914 (1985).

Nishikawa, et al., Exp. Cell Res. 223, 357 (1996).

Uyama, et al., Transplantation 55, 932 (1993).

Den Braber, et al. J. Biomed. Mater. Res. 40, 291 (1998).

Aiken, et al., J. Pediatr Surg 25, 140 (1990).

Seglen, Methods Cell Biol 13, 29 (1976).

Schwerer, et al., Clinica Chemica Acta 163, 237 (1987).

Peterson JE J Pathol Bacteriol 89, 153 (1965).

Duffy, et al., Anal. Chem. 70, 4974 (1998).

Mitaka, et al., Gastroenterol Hepatol 13 Suppl. S70 (1998).

Tateno, et al., Am J. Pathol 149, 1593 (1996).

Laconi, et al., Am J. Pathol 153, 319 (1998).

Hansborough & Franco (1998) "Skin Replacements", Clin. Plast. Surg. 25(3):407-23.

Henry, et al. (1998) "Micromachined Needles for the Transdermal Delivery of Drugs", The Eleventh Annual International Workshop on Micro Electro Mechanical Systems, Heidelberg, Germany, Jan. 25-29, 1998.

Kourepenis et al. (1998) "Performance of MEMS Inertial Sensors", Position Location and Navigation Symposium, Aerospace & Electronic Systems Society, Palm Springs, California, Apr. 20-23, 1996.

McWhorter et al. (1997) "vol. 2: Micromachining and Trends for the Twenty-First Century", Handbook of Microlithography, Micromachinery and Microfabrication. Ed. P. Rai-Choudhury, Bellingham, WA: SPIE Press.

Rennie, J. Ed. (1999) Special Report: The promise of tissue engineering. Scientific American 280: 37.

Vacanti et al. (1992) "Tissue-Inducing Biomaterials", Materials Research Society Symposium Proceedings 252: 367.

Langer & Vacanti, (1993) "Tissue Engineering", Science 260(5110): 920-6.

Langer & Vacanti, (1999) "Tissue Engineering: The obstacles to building new organs from cells and synthetic polymers are daunting but surmountable", Scientific American 280, 86-89.

Sunback & Vacanti, "Alternatives to liver transplantation: From hepatocyte transplantation to tissue-engineered organs", Gastroenterology 118: 438-442 (2000).

King, Kevin R.., et al., "Biodegradable Microfluidics", Advanced Materials, 2004, 16, No. 22, Nov. 18.

Shin, Michael et al., "Hybrid Bio/Artifical Microdevices", Biomedical Microdevices 6:4, 269-278, 2004.

Borenstein, Jeffrey T. et al., "Microfabrication Technology for Vascularized Tissue Engineering", Biomedical Microdevices 4:3, 167-175, 2002.

Fidkowski, Christina et al., "Endothelialized Microvasculature Based on a Biodegradable Elastomer", Tissue Engineering, vol. 11, No. 1/2, 2005.

Allen, et al., "Engineering Liver Therapies for the Future", Tissue Engineering (2002), vol. 8, No. 5, pp. 725-737.

Godbey, W.T., et al., "In Vitro Systems for Tissue Engineering", Ann. N. Y. Acad. Sci. 961: 10-26 (2002).

"Tissue", Merriam-Webster Online Dictionary. (2009). Merrian-Webster Online. May 21, 2009 URL: <http://www.m-w.com/dictionary/tissue>.

Carraro, Amedeo, et al., "Invitro analysis of a hepatic device with intrinsic microvascular-based channels", Biomed Microdevices (2008) 10:795-805.

Griffith, Linda G., et al., "In Vitro Organogenesis of Liver Tissue", Bioartificial Organs, vol. 831 of the Annals of the New York Academy of Sciences, Dec. 31, 1007.

King, Kevin R., "Biodegradable Microfluidics", Adv. Metter, 2004, 16, No. 22, Nov. 18, 2004.

Wang, Gou-Jen, et al., "Structure optimization of microvascular scaffolds", Biomed Microdevices (2005) 10: 51-58.

Kassab, Ghassan S. et al., "Morphometry of pig coronary arterial trees", American Physiological Society, 1993, 0363-6135/93.

Griffith, Linda G., et al., "In Vitro Organogenesis of Liver Tissue", Bioartificial Organs, vol. 831, pp. 382-397 of the Annals of the New York Academy of Sciences, Dec. 31, 1997.

* cited by examiner

MEMBRANE FORMATION (TIPS)

RENAL REPLACEMENT DEVICE: MICROPOROUS BIODEGRADABLE POLYMER

ULTRAFILTRATE

REABSORBED ULTRAFILTRATE

PROXIMAL TUBULE CELLS IN PDMS DEVICE DAY 0 +5hrs

PROXIMAL TUBULE CELLS IN PDMS DEVICE DAY 2

PROXIMAL TUBULE CELLS IN PDMS DEVICE DAY 6

METHOD OF DETERMINING METABOLISM OF A TEST AGENT

RELATED APPLICATIONS

This application is a division of application Ser. No. 11/183,115, filed Jul. 15, 2005, now U.S. Pat. No. 7,670,797, which is a continuation-in-part application of International Application Ser. No. PCT/US04/01098, filed Jan. 16, 2004, which claims priority to U.S. Ser. No. 60/440,539, filed on Jan. 16, 2003, the contents each of which are hereby incorporated herein by reference.

Reference is made herein to U.S. Ser. No. 10/187,247, filed Jun. 28, 2002, which claims priority to U.S. Ser. No. 60/367,675, filed Mar. 25, 2002, and which is a CIP of Ser. No. 09/560,480, filed Apr. 28, 2000, now U.S. Pat. No. 6,455,311, which claims priority to U.S. Ser. No. 60/165,329, filed Nov. 12, 1999 and to U.S. Ser. No. 60/131,930, filed Apr. 30, 1999, the contents each of which are expressly incorporated herein by reference. Reference is also made herein to U.S. Ser. No. 10/038,891, filed Jan. 2, 2002, which claims priority to U.S. Ser. No. 60/259,283 filed Jan. 2, 2001. Reference is also made herein to International Appln. No. PCT/US03/29880, which claims priority to U.S. Ser. No. 60/412,981, filed on Sep. 23, 2002, and U.S. Ser. No. 60/449,291, filed on Feb. 21, 2003, the contents each of which are hereby incorporated herein by reference.

GOVERNMENT RIGHTS NOTICE

This invention was made with Government support under Grant No. DAMD17-99-2-9001 awarded by the U.S. Department of the Army. The U.S. Government has certain rights in this invention.

JOINT RESEARCH AGREEMENT

Inventions described in this application were made by or on behalf of The General Hospital Corporation and The Charles Stark Draper Laboratory, Inc. which are parties to a joint research agreement that was in effect on or before the date such inventions were made and such inventions were made as a result of activities undertaken within the scope of the joint research agreement.

Each of the foregoing applications and patents and articles, and each document cited or referenced in each of the foregoing applications and patents and articles, including during the prosecution of each of the foregoing applications and patents ("application and article cited documents"), and any manufacturer's instructions or catalogues for any products cited or mentioned in each of the foregoing applications and patents and articles and in any of the application and article cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein can be used in the practice of this invention. Documents incorporated by reference into this text are not admitted to be prior art. Furthermore, authors or inventors on documents incorporated by reference into this text are not to be considered to be "another" or "others" as to the present inventive entity and vice versa, especially where one or more authors or inventors on documents incorporated by reference into this text are an inventor or inventors named in the present inventive entity.

FIELD OF THE INVENTION

The present invention generally relates to a combination of the fields of tissue engineering, drug discovery and drug development. It more specifically provides new methods and materials for testing the efficacy and safety of experimental drugs, defining the metabolic pathways of experimental drugs and characterizing the properties (e.g., side effects, new uses) of existing drugs. Preferably, evaluation is carried out in three-dimensional tissue-engineered systems, wherein drug toxicity, metabolism, interaction and/or efficacy can be determined.

BACKGROUND

Drug discovery and development consists of an arduous testing process, beginning with the demonstration of pharmacological effects in experimental cell and animal models and ending with drug safety and efficacy studies in patients. It is estimated that only 1 out of 5,000 screened compounds receives FDA approval as a safe and effective new medicine. Approximately 25% of compounds are eliminated in pre-clinical toxicological studies. Thus, a significant number of drug candidates in pre-clinical development fail to progress out of this stage due to unacceptable levels of toxicity in test systems.

Multiple pharmacologic parameters are considered when evaluating a drug candidate. Knowledge of the absorption, distribution, metabolism and excretion profile ("ADME") of a drug and its metabolites in humans (and animals used in toxicology assessments) is crucial to understanding differences in effect among individuals in a population and for optimizing dosimetry. Absorption and bioavailability are standard measures of the amount of biologically active material distributed to the systemic circulation or local site of action. Duration of drug action is often dependent on how rapidly the body eliminates the active molecules, either through metabolism, which involves chemical modification by drug-metabolizing enzymes, or by excretion, which involves binding and transport away from biologically active sites in the body. Thus, typical pre-clinical studies involve monitoring permeation across epithelial membranes (e.g., gastrointestinal mucosa), studies of drug metabolism, identification of plasma protein binding and evaluation of transport into and out of tissues, especially organs that eliminate drug products, such as the kidney and liver.

New Drug Applications, or NDAs, are submitted on the basis of data obtained from a small number of patients (>10,000), which is usually not indicative of the general population at large. Often, limited toxicity is observed and the selected patients have relatively normal organ function. Toxicity refers to any unwanted effect on normal structural or functional integrity. A toxic dose refers to a dose producing an unwanted or overly exaggerated pharmacological effect in a subject (i.e., the dose received by a subject when the first truly toxic signs develop). Failure in development of candidate drugs often occurs when an unacceptable level of toxicity develops.

Often, healthy subjects take part in early stage clinical studies. However, patient responses to drugs are typically more complex and less predictable than responses in the healthy subjects. The chances of adverse drug effects in patients are greatly increased due to increased susceptibility (e.g., increased susceptibility due to drug to drug interactions and comorbid conditions). There can be significant differences in toxicology and metabolism among groups of patients that are not detected until the after drug has advanced from pre-clinical studies. In the worst case, significant effects on a patient population are not detected until after a drug receives approval from the Food and Drug Administration. Therefore, pre-clinical approaches to identify toxicity in the early phases of drug discovery represent an important step towards efficient drug development.

Current pre-clinical toxicity and pharmacology studies utilize in vitro assays involving cultured cells or subcellular organelles, as well as in vivo animal models to investigate drug metabolism, toxicity and possible efficacy. While technological advances in cell, molecular, and biochemical assays have made significant strides, a number of problems still exist. First, in vitro assays using purified or recombinant enzymes and cell cultures provide the first step in determining pharmacologic and toxicologic parameters to be used thereafter in animal models, but are often too simplistic to account for the multifactorial events that occur during drug metabolism in a human system or human organ. Second, data obtained in animal models cannot be reliably extrapolated to human systems. Third, many drugs used to treat chronic diseases such as HIV infection or Alzheimer's disease necessitate dosing regimens that are applied over long periods of time, and in some cases, over the lifetime of an individual. Currently, development of chronic toxicity is most practically observed during long-term patient use.

The high attrition rate of drug candidates is a major economic deterrent in the pharmaceutical industry, as drug failure may be identified only after great time and expense are invested. These failures can be attributed, in part, to a lack of effective pre-clinical models and assay systems. Accordingly, there is a great need in the art to develop an in vitro human system that can effectively evaluate the pharmacologic and toxicologic properties of drug candidates. Improved in vitro model systems will allow the drug development process to reliably predict the in vivo response before the drug reaches the clinic, decreasing time, expense and significant risks to patient health. In addition, many serious diseases (e.g., hepatitis C) lack reliable animal model systems, a problem that has severely handicapped the drug discovery process. Improved in vitro model systems will also provide an opportunity for meaningful pre-clinical experimentation, which is essential for the development of therapeutics in the absence of animal model systems.

OBJECTS AND SUMMARY OF THE INVENTION

The invention provides a method for determining metabolism of a test agent in a tissue, the method comprising:
A) providing a test agent to a three-dimensional tissue engineered system;
B) incubating the test agent in the presence of an enzyme within said system, such that an enzyme-substrate complex is formed between the enzyme and the test agent; and
C) detecting one or more metabolites of the test agent.

Three-dimensional tissue-engineered systems of the invention can comprise liver tissue, kidney tissue, cardiac tissue, cartilage tissue, or bone marrow tissue, and combinations thereof. Preferably, the three-dimensional tissue engineered system of the invention comprises microfabricated polymer scaffolds.

Test agents include, but are not limited to, opioid analgesics, anti-inflammatory drugs such as antihistamines and non-steroidal anti-inflammatory drugs (NSAIDs), diuretics such as carbonic anhydrase inhibitors, loop diuretics, high-ceiling diuretics, thiazide and thiazide-like agents, and potassium-sparing diuretics, agents that impinge on the renal and cardiovascular systems such as angiotensin converting enzyme inhibitors, cardiac drugs such as organic nitrates, calcium channel blockers, sympatholytic agents, vasodilators, β-adrenergic receptor agonists and antagonists, α-adrenergic receptor agonists and antagonists, cardiac glycosides, anti-arrhythmic drugs, agents that affect hyperlipoproteinemias such as 3-hydroxymethylglutaryl-coenzyme A (HMG-CoA) inhibitors, anti-neoplastic agents such as alkylating agents, antimetabolites, natural products, antibiotics, and other drugs, immunomodulators, anti-diabetic agents, and anti-microbial agents such as antibacterial agents, antiviral agents, antifungal agents, antiprotozoal agents, and antihelminthic agents.

Enzyme-substrate complexes can comprise enzymes including, but not limited to, cytochrome P450, alkaline phosphatase, α-galactosidase, β-galactosidase, α-glucosidase, β-glucosidase, α-glucuronidase, β-glucuronidase, α-amylase, NADPH-cytochrome P450 reductase, cytochrome $b_5$, N-demethylase, O-demethylase, acetylcholinesterase, pseudocholinesterase, epoxide hydrolase, amidases, uridine diphosphate (UDP)-glucuronosyltransferases, phenol sulfotransferase, alcohol sulfotransferase, sterid sulfotransferase, and arylamine sulfotransferase, UDP-glycosyltransferases, purine phosphoribosyltransferase, N-acetyltransferases, glutathione S-transferase, phenylethanolamine N-methyltransferase, non-specific N-methyltransferase, imidazole N-methyltransferase, catechol-O-methyltransferase, hydroxyindole-O-methyltransferase, S-methyltransferase, alcohol dehydrogenase, aldehyde dehydrogenase, xanthine oxidase, monoamine oxidases, diamine oxidases, flavoprotein N-oxidases, hydroxylases, aromatases, cysteine conjugate β-lyase, and alkylhydrazine oxidase. The enzyme can be endogenously expressed in the tissue, and can have either normal enzymatic activity or altered enzymatic activity, for example, such as where the enzyme contains a polymorphism or mutation.

The enzyme can be a recombinant enzyme.

In a preferred embodiment, the enzyme is cytochrome P450.

Enzyme metabolites can be detected by methods including, but not limited to, liquid chromatography, mass spectrometry, nuclear magnetic resonance, or spectrophotometry.

The invention provides a method for determining toxicity of a test agent in a tissue, the method comprising:
A) providing a test agent to a three-dimensional tissue engineered system;
B) incubating the test agent in the presence of the tissue; and
C) detecting an undesired effect.

The test agent can be provided for any duration selected by one of skill in the art, but preferably, the test agent is provided for at least 24 hours. Methods of the invention are also well suited for providing the test agent for longer durations (e.g., 90 days or longer).

The undesired effect can comprises carcinogenicity, cell death, changes in gene expression, changes in protein expression or irregular metabolism and combinations thereof. Other undesired effects can be readily identified by one skilled in the art, and may be specific to the type of test agent provided, or the type of tissue that the test agent is provided to.

Carcinogenicity can be detected by changes in gene expression, changes in protein levels, abnormal cell proliferation, or changes in expression of antigenic determinants and combinations thereof.

Cell death can be detected by vital dyes, lactate dehydrogenase release, caspase activity, annexin V staining, phosphatidylserine staining or TUNEL assay.

Changes in gene expression can be detected by microchip analysis, RT-PCR, in situ hybridization, fluorescence in situ hybridization or Northern analysis.

Changes in protein expression can be detected by quantitative Western blot, immunohistochemistry, immunofluorescence, enzyme-linked immunosorbent assay, amino acid sequence analysis, fluorescence activated cell sorting or protein concentration assays.

Irregular metabolism can be indicated by detecting abnormal enzyme function in enzymes including, but not limited to, cytochrome P450, alkaline phosphatase, α-galactosidase, β-galactosidase, α-glucosidase, β-glucosidase, α-glucuronidase, β-glucuronidase, α-amylase, NADPH-cytochrome P450 reductase, cytochrome $b_5$, N-demethylase, O-demethylase, acetylcholinesterase, pseudocholinesterase, epoxide hydrolase, amidases, uridine diphosphate (UDP)-glucuronosyltransferases, phenol sulfotransferase, alcohol sulfotransferase, sterid sulfotransferase, and arylamine sulfotransferase, UDP-glycosyltransferases, purine phosphoribosyltransferase, N-acetyltransferases, glutathione S-transferase, phenylethanolamine N-methyltransferase, non-specific N-methyltransferase, imidazole N-methyltransferase, catechol-O-methyltransferase, hydroxyindole-O-methyltransferase, S-methyltransferase, alcohol dehydrogenase, aldehyde dehydrogenase, xanthine oxidase, monoamine oxidases, diamine oxidases, flavoprotein N-oxidases, hydroxylases, aromatases, cysteine conjugate β-lyase, and alkylhydrazine oxidase.

In one embodiment, methods of the invention are used to identify test agents having anti-viral activity against hepatitis C. Accordingly, the invention provides a method for determining efficacy of a test agent, wherein efficacy comprises activity sufficient to decrease or eliminate hepatitis C virus in liver tissue, the method comprising:
  A) providing a test agent to a three-dimensional liver tissue engineered system;
  B) incubating the test agent in the presence of the tissue; and
  C) measuring levels of hepatitis C virus.

The invention further provides a method for determining efficacy of a test agent, wherein efficacy comprises activity sufficient to decrease or eliminate hepatitis C virus in liver tissue, the method comprising:
  A) providing a test agent to a three-dimensional liver tissue engineered system;
  B) incubating the test agent in the presence of the tissue; and
  C) detecting improved liver function.

Improved liver function is indicated by detecting normal enzyme levels, histology or protein production and combinations thereof.

These and other embodiments are disclosed or are obvious from and encompassed by, the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

FIG. 12 shows phase-contrast photographs of small hepatocytes and nonparenchymal cells cultured on regular culture flasks.

FIG. 13 shows a cell sheet lifted from a silicon wafer.

FIG. 15 shows H & E staining of implanted constructs.

FIG. 16 shows immunohistochemical staining of implanted constructs.

FIG. 33 illustrates a branching sequence in which a fractal algorithm was used to create a hexagonal pattern.

FIG. 34 illustrates a three-dimensional design, Hextak, in accordance with an embodiment of the invention. The layers in Hextak contain vessels in the plane of the wafer. Black lines mark vessels in the plane of the wafer; red and blue circles mark locations where vertical vessels meet these patterns.

FIG. 35 illustrates four separate layers of vertical vessels in the Hextak design.

FIG. 42 shows a full network appropriate for use as support for a tissue engineered organ.

A related graph shown in FIG. 47 depicts the same data in terms of micromoles of ECOD or its metabolites

DETAILED DESCRIPTION

Definitions

Figure 1A:
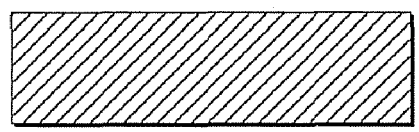
FIG. 1 shows a schematic describing a process for the production of a complex structure comprising channels wherein all channels do not have the same depth. The steps of the process are as follows: The process begins with a substrate wafer (A); Masking material is deposited (B); Masking material is patterned (C); Substrate wafer is etched (D); a second masking layer is deposited (E); The second masking layer is patterned (F); The substrate wafer is etched again (G); The masking layer is removed (H).
Figure 1E:
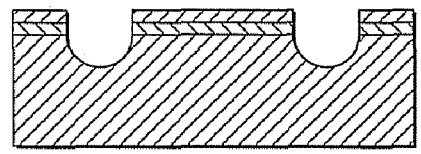
Figure 1B:
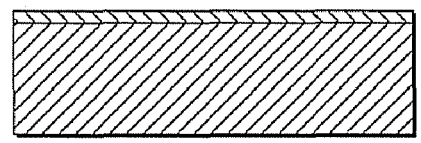
Figure 1F:
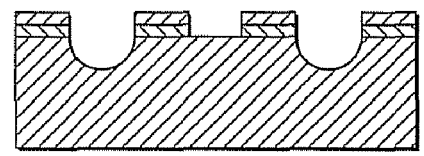
Figure 1C:
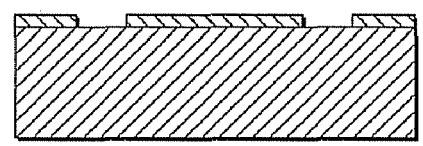
Figure 1G:
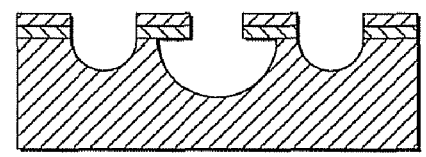
Figure 1D:
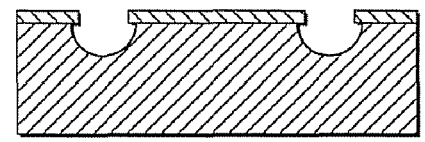
Figure 1H:
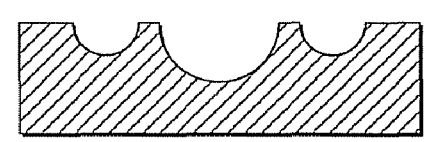
Figure 2:
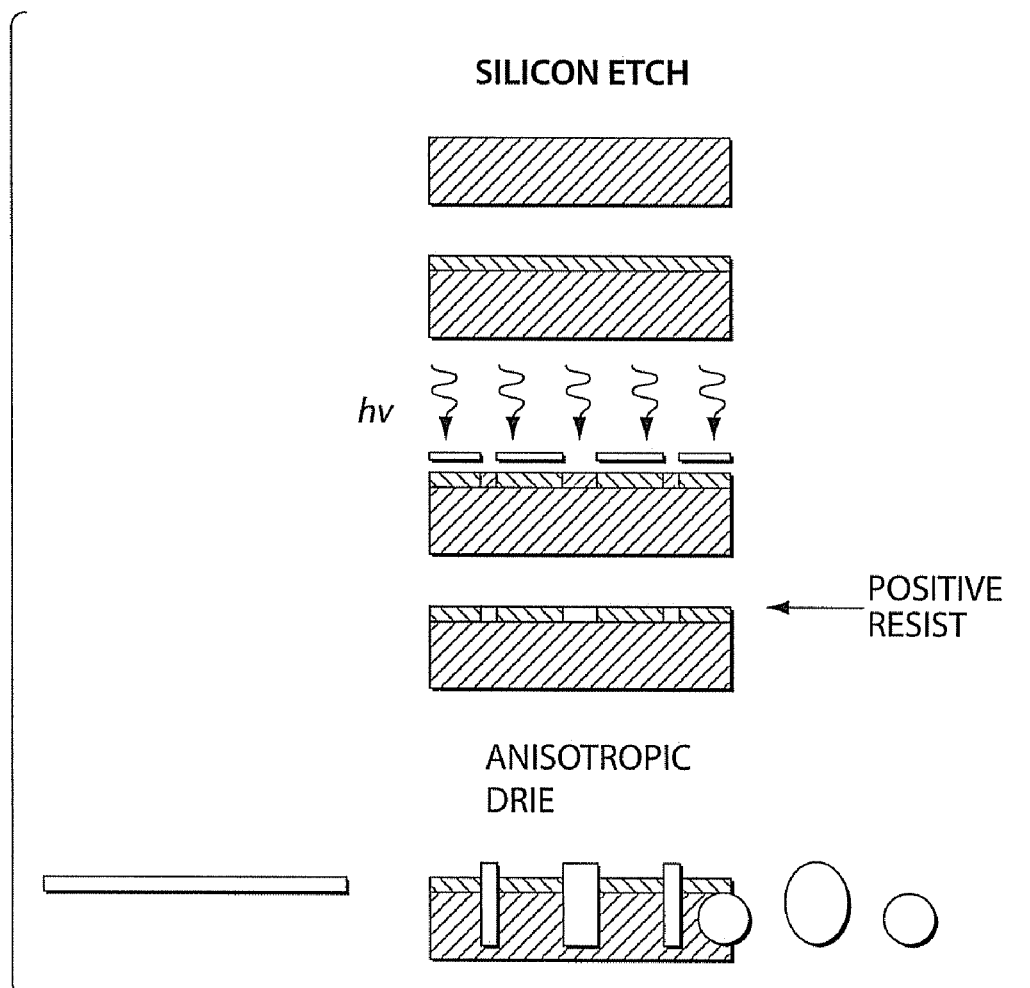
FIG. 2 shows a schematic of a pattern etched using an inductively-coupled plasma (ICP) system.
Figure 3A:
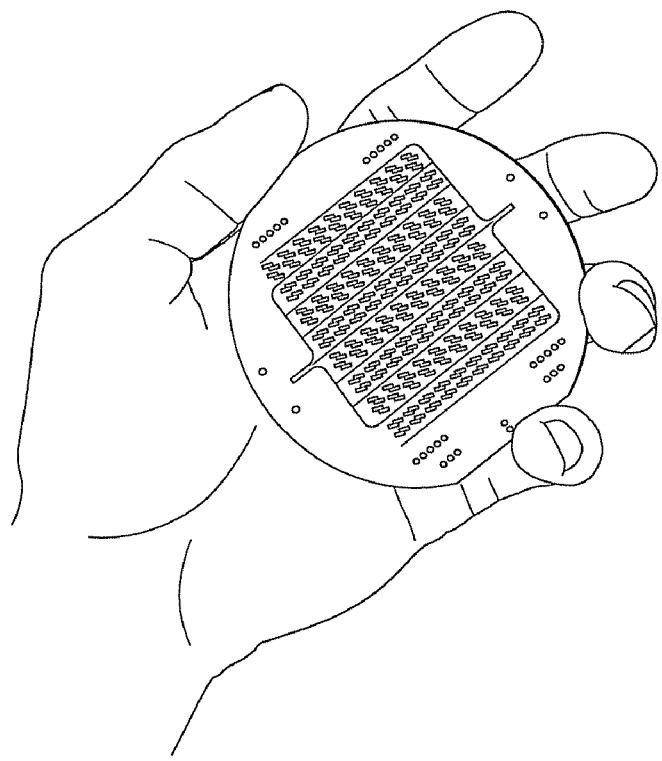
FIG. 3A shows a silicon wafer with a network of microchannels and FIG. 3B shows a polymer scaffold with a network of microchannels.
Figure 3B:
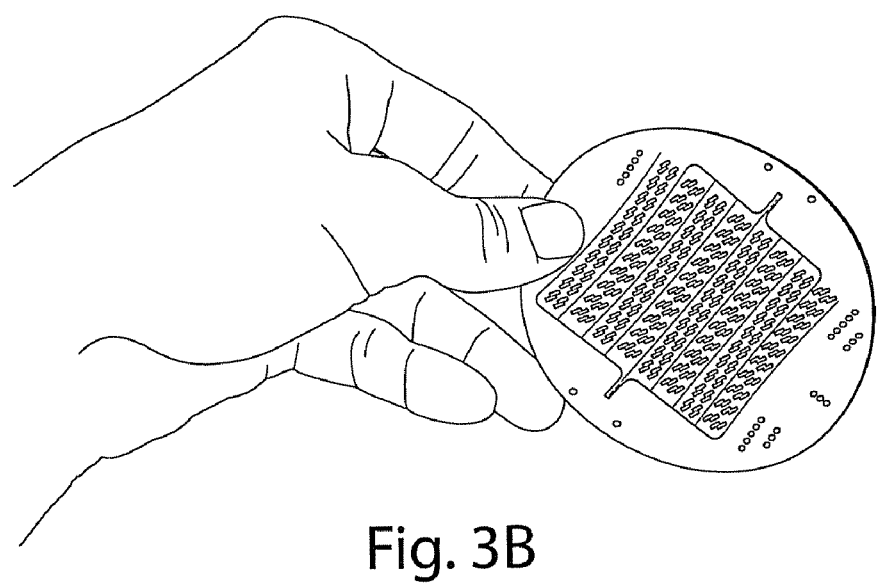
Figure 4:
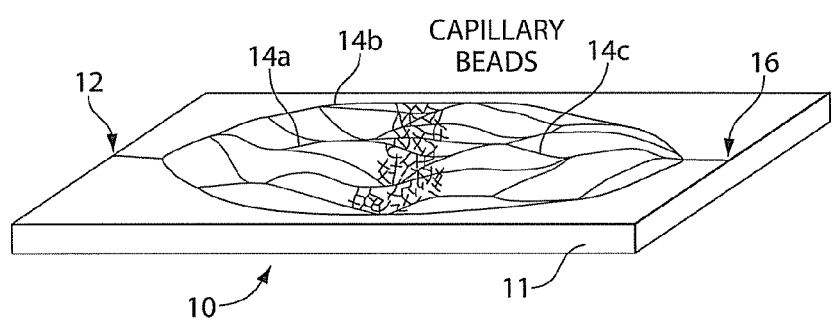
FIG. 4 shows a schematic of an etched surface showing a branching structure that branches out from a single inlet and then converges back into a single outlet.
Figure 5A:
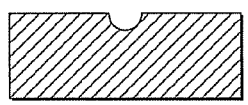
FIGS. 5 A, B, and C show schematics of a cross-sectional view of different etched channels in the surface of FIG. 4.
Figure 5B:
Figure 5C:
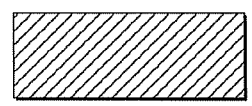
Figure 6A:
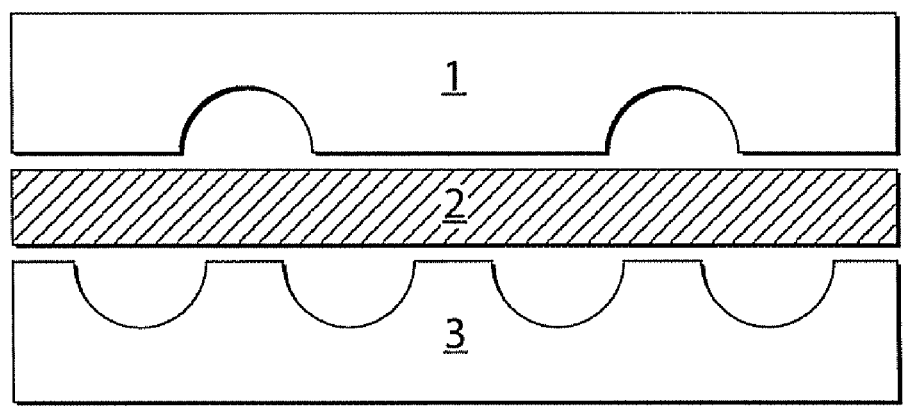
FIG. 6 shows schematic diagram of a cross section of an apparatus for tissue engineering and artificial organ support. The apparatus in FIG. 6A comprises a compartment for circulatory flow (1), a semi-permeable membrane for mass transfer of oxygen, nutrients and waste (2), and a compartment for functional cells and excretory system.
FIG. 6B shows the apparatus of 6A seeded with vascular cells or cells that form lumen (e.g. biliary ducts) (4) and functional cells (e.g. hepatocytes) (5).
Figure 6B:
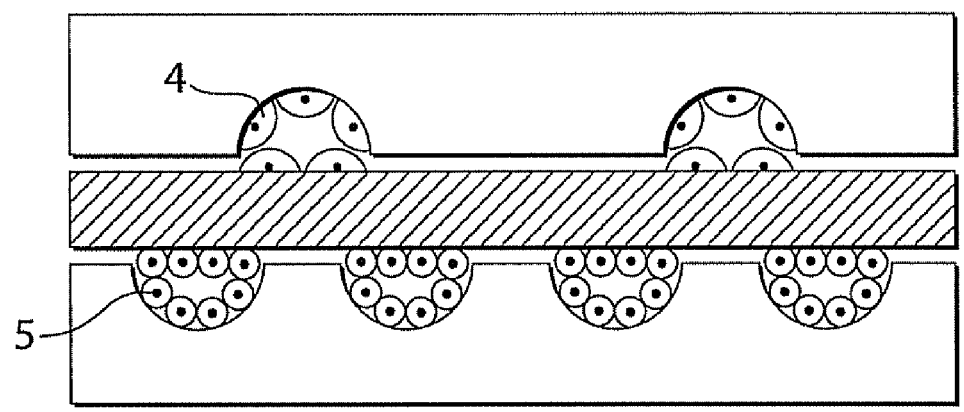
Figure 7:
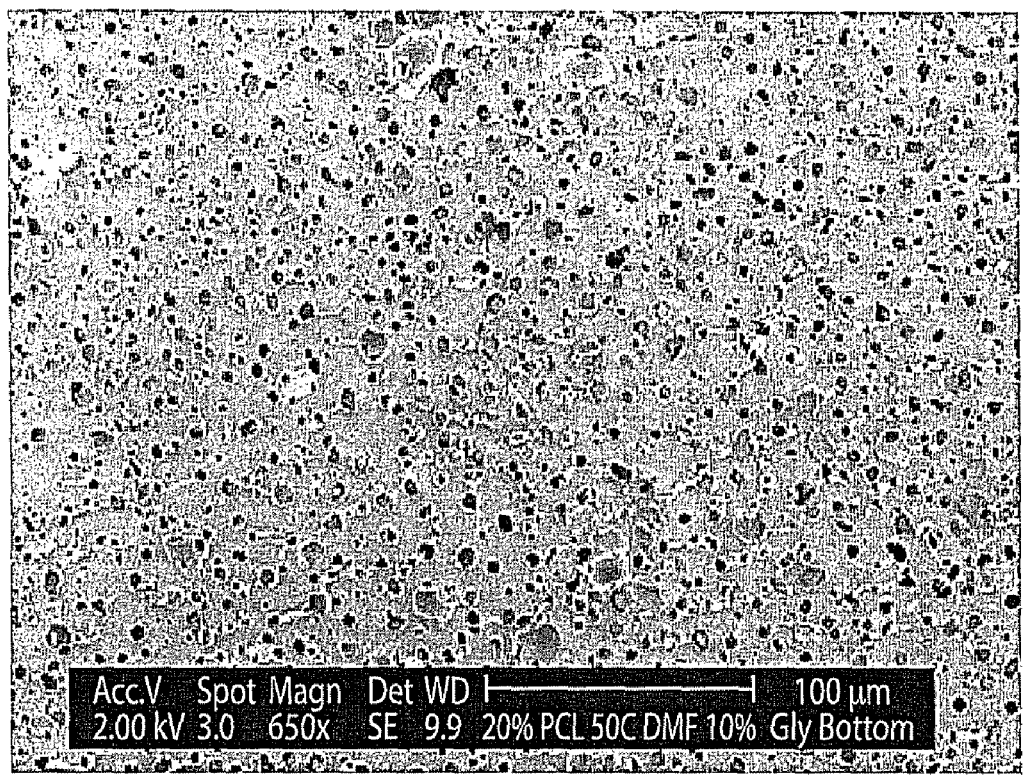
FIG. 7 shows electron micrographs of a semi-permeable membrane made using the TIPS procedure.
Figure 8:
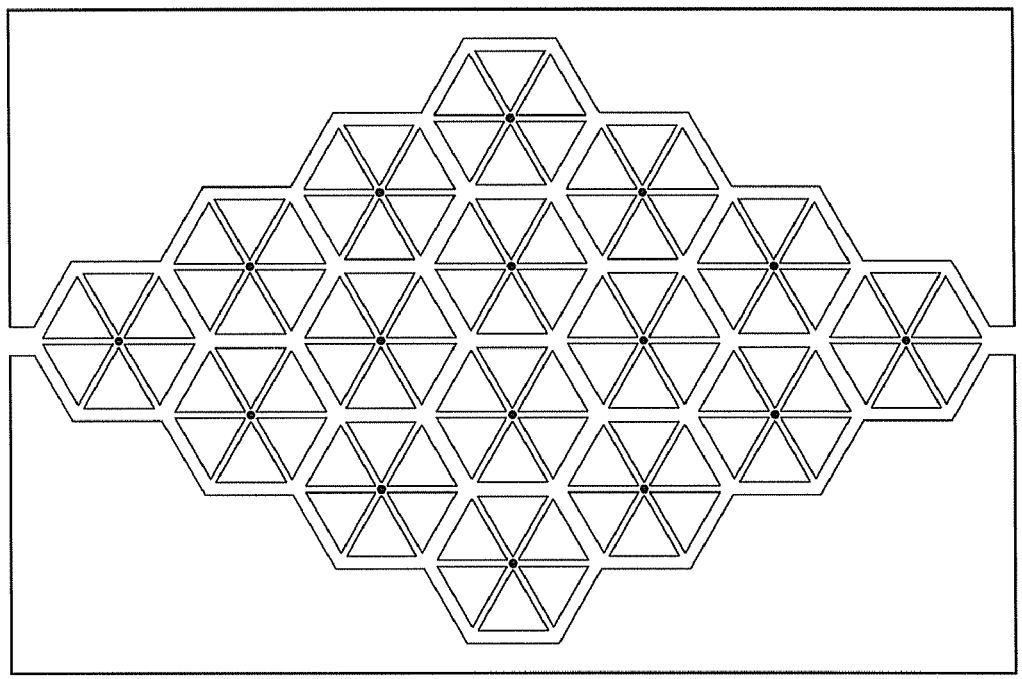
FIG. 8 shows a schematic top drawing of a mold or polymer scaffold. The triangles represent areas coated with cell adhesion molecules to promote the adhesion of cells (e.g. hepatocytes). The white areas between the triangles represent microchannels; in some applications, they are not coated with cell adhesion molecules, and so are open for colonization by cells that can form vascular tissue (e.g. endothelial cells). The black circle in the middle of each hexagon is a vertical through-hole.
Figure 9:
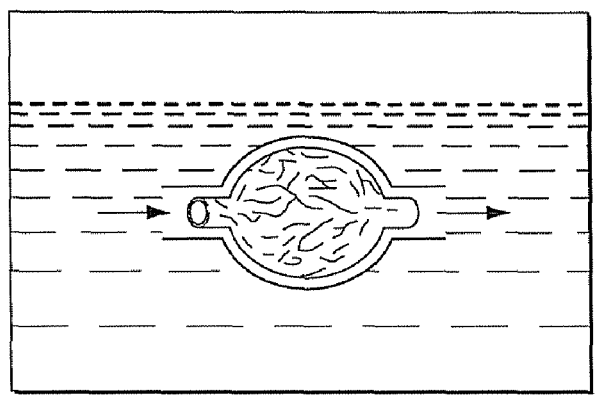
FIG. 9 shows how the organ of FIG. 6 can be connected to a fluid by anastomosis of the inlet and outlet.

As used herein, the term "toxicity" is defined as any unwanted effect on human cells or tissue caused by a test agent, or test agent used in combination with other pharmaceuticals, including unwanted or overly exaggerated pharmacological effects. An analogous term used in this context is "adverse reaction."

In the pharmaceutical arts, the term "efficacy" can describe the strength of a response in a tissue produced from a single drug-receptor complex. In the context of this disclosure, "efficacy" can also be defined as a response elicited by a drug or test agent that improves the phenotype of a cell or tissue.

A "test agent" is any substance that is evaluated for its ability to diagnose, cure, mitigate, treat, or prevent disease in a subject, or is intended to alter the structure or function of the body of a subject. A test agent in an embodiment can be a "drug" as that term is defined under the Food Drug and Cosmetic Act, §321(g)(1). Test agents include, but are not limited to, chemical compounds, biologic agents, proteins, peptides, nucleic acids, lipids, polysaccharides, supplements, diagnostic agents and immune modulators.

"Pharmacokinetics" refers to the actions of the body on a drug. Pharmacokinetic processes include, but are not limited to, absorption, distribution, metabolism, and elimination of drugs.

"Pharmacodynamics" refers to the actions of a drug on the body. Because certain classes of drugs exhibit similar effects on the body, pharmacodynamic properties determine the group in which a drug or agent is classified.

An "agonist" is a drug, agent, or compound that binds to and activates its cognate receptor in some fashion, which directly or indirectly brings about a physiological effect.

An "antagonist" is an agent that binds to a receptor, and which in turn prevents binding by other molecules.

"Phase I metabolism" refers to biochemical reactions that usually convert the parent drug, agent, or compound by introducing or unmasking a functional group, including but not limited to, hydroxyl, amino, or sulfhydryl groups. The products of Phase I metabolism are often inactive, though in some instances activity is only modified or even higher than the parent drug.

"Phase II metabolism" encompasses biochemical reactions that couple or conjugate polar molecules to parent drugs or their phase I metabolites that contain suitable functional groups for conjugation. Phase II metabolic reactions require energy. Phase II metabolism can occur before or in the absence of Phase I reactions.

A "substrate" is a molecule that binds to the active site of the enzyme, and upon which an enzymatic reaction can be catalyzed. As used herein, a "substrate" is typically the test agent, or a metabolite thereof, which acts as a substrate for one or more metabolic enzymes.

"Comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Methods of the Invention

Three-dimensional tissue engineered systems of the invention are useful for studying several parameters of a test agent, including metabolism, toxicity and efficacy. Methods of the invention can be used to screen experimental drugs or "test agents" that have no known metabolic or pharmacokinetic profile, in order to obtain such information, including information necessary to assess toxicity. Toxicity can often occur as a result of drug-to-drug interactions. Thus, methods of the invention can be used to study the combination of test agents with known drugs or other test agents. These methods are particularly relevant to use in clinical settings since many patients are treated with multiple drugs.

In general, test agents are incubated with the three-dimensional tissue engineered systems of the invention in a dosage range estimated to be therapeutic and for a duration sufficient to produce an effect (e.g., metabolic effects or effects indicating to toxicity or efficacy). The incubation time can range between about 1 hour to 24 hours, or can be extended as necessary for several days or even weeks. The incubation conditions typically involve standard culture conditions known in the art, including culture temperatures of about 37° C., and culture mediums compatible with the particular cell type selected.

Test agents that can be analyzed according to methods of the invention include, but are not limited to, opioid analgesics, anti-inflammatory drugs such as antihistamines and non-steroidal anti-inflammatory drugs (NSAIDs), diuretics such as carbonic anhydrase inhibitors, loop diuretics, high-ceiling diuretics, thiazide and thiazide-like agents, and potassium-sparing diuretics, agents that impinge on the renal and cardiovascular systems such as angiotensin converting enzyme (ACE) inhibitors, cardiac drugs such as organic nitrates, calcium channel blockers, sympatholytic agents, vasodilators, $\beta$-adrenergic receptor agonists and antagonists, $\alpha$-adrenergic receptor agonists and antagonists, cardiac glycosides, antiarrhythmic drugs, agents that affect hyperlipoproteinemias such as 3-hydroxymethylglutaryl-coenzyme A (HMG-CoA) inhibitors, anti-neoplastic agents such as alkylating agents, antimetabolites, natural products, antibiotics, and other drugs, immunomodulators, anti-diabetic agents, and anti-microbial agents such as antibacterial agents, antiviral agents, antifungal agents, antiprotozoal agents, and antihelminthic agents, but are not limited to these agents.

Metabolism

The cytochrome P450 enzyme family is the major catalyst of drug biotransformation reactions, and can be used in vitro to determine drug binding and drug metabolism in the tissue-engineered systems of the present invention. Assays for monitoring enzyme metabolism, including cytochrome P450 enzyme function, can be performed according to methods well known in the art. Several of these assays are described below.

The cytochrome P450 superfamily of enzymes, which are primarily liver enzymes, catalyzes a wide variety of oxidative and reductive reactions and has activity towards a chemically diverse group of substrates. Cytochrome P450 enzymes are heme-containing membrane proteins localized in the smooth endoplasmic reticulum of numerous tissues. These hemoproteins are in close association with a second membrane protein, NADPH-cytochrome P450 reductase. Oxidative biotransformations catalyzed by cytochrome P450 monooxygenases include aromatic and side chain hydroxylation, N-, O-, and S-dealkylation, N-oxidation, sulfoxidation, N-hydroxylation, deamination, dehalogenation, and desulfuration. Cytochrome P450 enzymes, generally under conditions of low oxygen tension, also catalyze a number of reductive reactions. The only common structural feature of the diverse group of drugs oxidized by cytochrome P450 enzymes is their high lipid solubility.

A plurality of cytochrome P450 gene families has been identified in humans, and a number of distinct cytochrome P450 enzymes often exist within a single cell. The cytochrome P450 multigene family is classified by sequence similarity of the individual proteins. A given cytochrome P450 family is further divided into subfamilies, such that protein sequences within the same subfamily are >55% identical. The cytochrome P450 1, 2, 3, and 4 families (CYP1, CYP2, CYP3, CYP4) encode the enzymes involved in the majority of all drug biotransformations, while the gene products of the remaining cytochrome P450 families are important in the metabolism of endogenous compounds, such as steroids and fatty acids. The relevant CYP enzymes that are expressed in humans include, but are not limited to, CYP1A1, CYP1A2, CYP2A3, CYP2B6, CYP2B7, CYP2B8, CYP2C8, CYP2C9, CYP2C10, CYP2D6, CYP2D7, CYP2D8, CYP2E1, CYP2F1, CYP3A3, CYP3A4, CYP3A5, and CYP4B1. As a result of the relatively low substrate specificity among the cytochrome P450 proteins, two or more individual enzymes often can catalyze a given biotransformation reaction. CYP3A4 is involved in the biotransformation of a majority of all drugs and is expressed at significant level extrahepatically.

Cytochrome P450 is a hemoprotein that when reduced and complexed with carbon monoxide, a characteristic absorption spectrum results. The reduced carbon monoxide spectrum of cytochrome P450 absorbs maximally at around 450 nm and the extinction coefficient for the wavelength couple 450-490 nm has been accurately determined to be 91 mM$^{-1}$ cm$^{-1}$, thus allowing quantitative determination of this hemoprotein. If high turbidity is present in the sample containing cytochrome P450, spectrophotometric determination of the hemoprotein can be carried out in a split beam instrument, i.e. one containing both a sample and reference compartment to offset turbidity. Solid sodium dithionite, for example, is used as a reducing agent, and the samples can be gassed with carbon monoxide shortly after dithionite addition (the reduced ferrous form of CYP450 is relatively unstable). Excessively high gas flow rates can result in frothing and protein denaturation. If a prominent peak is observed at 420 nm after gassing with carbon monoxide, this is indicative of the presence of inactive cytochrome P420, and is to be avoided.

The tissue content of cytochrome $b_5$ can also be analysed using the same sample. If both cytochrome P450 and cytochrome $b_5$ concentration are required from the same sample, the cytochrome $b_5$ must be determined first as in the method given below. This is achieved by determining the difference absorbance spectrum of NADH-reduced versus oxidized cytochrome $b_5$. The reduced, ferrous form of cytochrome $b_5$ has an absorbance maximum at 424 nm in difference spectrum and the extinction coefficient for the wavelength couple 424-490 nm is 112 mM$^{-1}$ cm$^{-1}$. NADH can be used as the reductant because of the presence of the flavoprotein enzyme NADH-cytochrome $b_5$ reductase in tissue preparations, an enzyme that relatively specifically and quantitatively reduces cytochrome $b_5$.

Many agents can bind to cytochrome P450, resulting in characteristic perturbations of the absorbance of the heme iron. The absorbance changes can be utilized to quantitatively describe drug binding to the hemoprotein, resulting in the determination of the apparent spectral dissociation constant ($K_s$) and maximum spectral change elicited by the drug ($\Delta A_{max}$). These two parameters are formally similar to the $K_m$ and $V_{max}$ values described by Michaelis-Menten kinetics for enzyme-catalysed reactions. In the broadest sense, $K_s$ is a measure of drug affinity for cytochrome P450 and $\Delta A_{max}$ is the maximum spectral change. These two spectral parameters are therefore of use in comparing the interactions of test agents with various forms of cytochrome P450 or in comparing the interactions of different test agents, or combinations thereof, with the same form of cytochrome P450.

NADPH-cytochrome c (P450) reductase is a flavoprotein enzyme localized in the microsomal fraction of the liver that transfers the necessary reducing equivalents from NADPH to cytochrome P450 during certain drug metabolism reactions as:

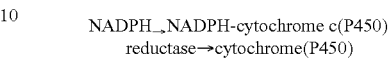

NADPH→NADPH-cytochrome c(P450) reductase→cytochrome(P450)

As the reduction of cytochrome P450 is relatively difficult to assay directly, a simplified determination of enzyme activity is widely used, utilizing exogenous cytochrome c (oxidized, ferric form) as an artificial election acceptor. Accordingly, the reduction of cytochrome c by NADPH-cytochrome c (P450) reductase mirrors the reduction of cytochrome P450. The principle of the method is that oxidized (ferric) cytochrome c has a characteristic absorption spectrum, as does the reduced (ferrous) form. However, the reduced form has a characteristic absorption band at 550 nm, a band that is absent in the oxidized form. Therefore, the enzyme activity can be conveniently assayed by measuring the increase in absorbance at 550 nm as a function of time.

Many drugs are hydroxylated in the liver by the cytochrome P450-dependent, mixed-function oxidase system, and the 4-hydroxylation of aniline is a convenient, reproducible assessment of this reaction as:

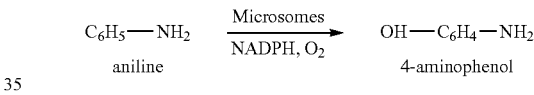

$$C_6H_5-NH_2 \xrightarrow[\text{NADPH, } O_2]{\text{Microsomes}} OH-C_6H_4-NH_2$$
aniline → 4-aminophenol The 4-aminophenol metabolite produced is chemically converted to a phenolindophenol complex with an absorption maximum at 630 nm and is based on the method of Schenkman et al. Addition of aniline HCl solution initiates the enzyme reaction. The reaction is terminated with ice-cold 20% trichloroacetic acid and centrifuged to yield a clear solution (5 min in a bench centrifuge at maximum speed is usually sufficient). The supernatant can then be added to a 1% phenol solution in a separate test tube in the presence of sodium carbonate. After a 30-minute incubation, the absorbance is read at 630 nm.

N-demethylation of drugs is a common metabolic pathway and usually proceeds by initial hydroxylation at the α-carbon atom and subsequent breakdown of the carbinolamine intermediate liberating formaldehyde. Therefore, if the formaldehyde produced could be measured, this would then yield an appropriate assay for the N-demethylase activity. Formaldehyde may be trapped in solution as the semicarbazone and measured by the colorimetric procedure of Nash (1953), based on Hantzsch reaction. A solution including semicarbazide, MgCl$_2$, and aminopyrine can be added to microsomes or post-mitochondrial supernatant, and the reaction occurs over 30 minutes. The reaction is terminated by addition of zinc sulfate on ice. A saturated barium hydroxide solution is added to the mix, and centrifuged to a clear supernatant. The Nash reagent is then added to the supernatant and incubated at 60° C. for 30 minutes. After cooling the tubes, the absorbance is read at 415 nm.

In a similar manner to N-demethylation, many drugs can undergo O-demethylation reactions, catalyzed by the microsomal, cytochrome P450-dependent, mixed-function oxidase system. A useful substrate to monitor O-demethylation reactions is 4-nitroanisole, which is converted to 4-nitrophenol as

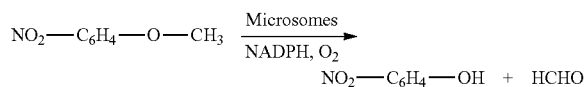

$$NO_2-C_6H_4-O-CH_3 \xrightarrow[\text{NADPH, O}_2]{\text{Microsomes}} NO_2-C_6H_4-OH + HCHO$$

The 4-nitrophenol thus produced, forms an intense yellow color at pH 10, with an absorbance maximum at 400 nm. Hence the activity of the enzyme system can be followed spectrophotometrically.

A number of nonspecific esterases and amidases have been identified in the endoplasmic reticulum of liver, intestine, and other tissues. Such enzymes include acetylcholinesterase, pseudocholinesterase, other esterases, epoxide hydrolase, but are not limited to these examples. The alcohol and amino groups exposed following hydrolysis of esters and amides are suitable substrates for conjugation reactions. Epoxide hydrolase is found in the endoplasmic reticulum of essentially all tissues and is in close proximity to the cytochrome P450 enzymes. Epoxide hydrolase generally is considered a detoxification enzyme; hydrolyzing highly reactive arene oxides generated from cytochrome P450 oxidation reactions to inactive, water-soluble transdihydrodiol metabolites. Proteases and peptidase enzymes are widely distributed in many tissues and are involved in the biotransformation of polypeptide drugs.

The glucuronosyl transferase family of enzymes is important in phase II drug conjugation reactions. Uridine diphosphate glucuronosyltransferases (UDP-glucuronosyltransferases) catalyze the transfer of an activated glucuronic acid molecule to aromatic and aliphatic alcohols, carboxylic acids, amines, and free sulfhydryl groups of both exogenous and endogenous compounds to for O-, N-, and S-glucuronide conjugates. The UDP-glucuronosyltransferases are microsomal enzymes. Their location in the microsomal membrane facilitates direct access to the metabolites formed in phase I reactions. In addition to high expression levels in the liver, UDP-glucuronosyltransferases are also found in the kidney, intestine, brain, and skin.

A useful compound to assess glucuronosyl transferase activity is 2-aminophenol, because this phenol readily forms as O-linked glucuronide conjugate in the presence of UDP-glucuronic acid. The assay for glucuronidation of 2-aminophenol is based on the colorimetric diazotisation method for free primary amino groups. The principle of the analytical method is based on the observation that when an aqueous solution of sodium nitrite is added to a cold, acidified solution of an aromatic amine, a diazonium salt is formed. Excess nitrite is removed by the addition of ammonium sulfamate and the diazonium salt is finally reacted with a complex aromatic amine (N-naphthylethylene diamine), to produce a brightly coloured azo compound that can be analysed spectrophotometrically. This method, therefore, detects the amino group of the 2-aminophenyl glucuronide. The method is relatively specific because excess substrate (2-aminophenol) is destroyed under the assay conditions (at pH 2.7) and therefore does not take part in the diazotisation reaction.

As the glucuronosyl transferases usually exhibit enzyme latency in the microsomal membrane, the assay is carried out in the presence of a detergent (usually Triton X-100) to offset the latency. Ascorbic acid is included as an anti-oxidant. The substrate 2-aminophenol can be added to test samples comprising, for example, either microsomal or post-mitochondrial fraction, at 37° C. in a shaking water bath, and the reaction allowed to proceed for 30 minutes. The reaction is terminated by addition of ice-cold 20% trichloroacetic acid in phosphate buffer, pH 2.7, allowed to stand on ice for 5 minutes and clarified by centrifugation. Fresh 0.1% sodium nitrite is added, followed by 0.5% ammonium sulfamate, and 0.1% N-naphthylethylene diamine, incubated at room temperature in the dark for 60 minutes. The absorbance is read at 540 nm against the substrate blank.

Sulfation also is an important conjugation reaction for hydroxyl groups. Cytosolic sulfotransferases catalyze the transfer of inorganic sulfur from the activated 3'-phosphoadenosine-5'-phosphosulfate donor molecule to the hydroxyl group on phenols and aliphatic alcohols. Examples of sulfotransferases include, but are not limited to, phenol sulfotransferase, alcohol sulfotransferase, sterid sulfotransferase, and arylamine sulfotransferase.

UDP-glycosyltransferases transfer glucose moieties in a similar fashion that glucuronosyltransferases conjugate glucuronic acid to pharmacologic agents. Ribose and deoxyribose sugar moieties can also be added, mediated by enzymes such as purine phosphoribosyltransferase, among others.

A family of N-acetyltransferases is responsible for the acetylation of amines, hydrazines, and sulfonamides. In contrast to most drug conjugates, acetylated metabolites are often less soluble in water than the parent drug, a property that prolongs their elimination from the body. Conjugation of electrophilic metabolites with the tripeptide glutathione represents a major detoxification pathway for drugs and carcinogens.

The glutathione-S-transferases are a family of isoenzymes that catalyse the conjugation of the endogenous tripeptide glutathione (gamma-glutamylcysteinylglycine) with a large number of structurally diverse, electrophilic drugs or their metabolites. The glutathione S-transferase enzymes are expressed in virtually all tissues. Glutathione conjugates are cleaved to cysteine derivatives and subsequently are acetylated by a series of enzymes located primarily in the kidney to give N-acetylcysteine conjugates collectively referred to as mercapturic acids. The glutathione-S-transferases consist of two subunits each of which is inducible by many drugs, and although some exceptions are known, their prime function is in the detoxification of biologically reactive electrophiles.

A convenient spectrophotometric method has been developed for the analysis of glutathione-S-transferase activity based on the enzyme-catalyzed condensation of glutathione with the model substrate 2,4-dinitro-1-chlorobenzene. The product formed (2,4-dinitrophenyl-glutathione) absorbs light at 340 nm and the extinction coefficient of this product is known to be 9.6 mM$^{-1}$ cm$^{-1}$, thus facilitating the analysis of enzyme activity based on product formation. It known in the art that the glutathione-S-transferase isoenzymes have similar but overlapping substrate specificities for the electrophilic substrate to be conjugated. Therefore one substrate that is readily reactive with a particular isoenzyme may not be substrate for another isoenzyme. Dinitrochlorobenzene is a good substrate for most of the glutathione-S-transferase isoenzymes, when results are interpreted with the knowledge that observed activity can represent a composite result of the activity of each isoenzyme present in the tissue preparation. One skilled in the art can readily interpret the data to consider the results as a composite rather than an individual measure of metabolic activity.

A glutathione solution can be prepared in the presence of dinitrochlorobenzene and potassium phosphate buffer, pH 6.5. Since the reaction is measured as a function of time, the reaction is directly assayed in cuvettes placed in the spectrophotometer. The reaction is initiated by adding a post-mitochondrial or microsomal fraction from liver, mixed thoroughly, and the increase in absorbance at 340 nm over a 5 minute period should be measured as quickly as possible.

Methylation and conjugation with the amino acids glycine, glutamine, and taurine are less common reactions for drugs but represent important reactions for endogenous compounds. Methyltransferases include, but are not limited to, phenylethanolamine N-methyltransferase, non-specific N-methyltransferase, imidazole N-methyltransferase, catechol-O-methyltransferase, hydroxyindole-O-methyltransferase, and S-methyltransferase.

Other enzymes that are involved in drug metabolism, and that can be assayed in accordance with methods of the invention to determine the metabolic profile of a test agent, include, but are not limited to, alcohol dehydrogenase, aldehyde dehydrogenase, xanthine oxidase, amine oxidases such as monoamine oxidases, diamine oxidases, flavoprotein N-oxidases, and hydroxylases, aromatases, cysteine conjugate β-lyase, α-galactosidase, β-galactosidase, α-glucosidase, β-glucosidase, α-glucuronidase, β-glucuronidase, α-amylase, and alkylhydrazine oxidase.

Levels of metabolites, if known, can be detected using methods well known in the art as a reflection of metabolic activity, such as liquid chromatography. Liquid chromatography coupled with tandem mass spectrometric detection (LC/MS/MS) can be used as an analytical method to monitor early absorption, distribution, metabolism and elimination testing. This method provides excellent sensitivity, specificity and high sample throughput. The quantitative selectivity afforded by reaction monitoring on a triple quadrupole instrument precludes the need for high chromatographic resolution or extensive sample clean up. Using automated sample-processing techniques, such as on-line column switching, combined with high-sample-density microtiter plates, can further maximize analytical throughput. Modern LC/MS/MS also offers limits of detection extending down to the sub-nanogram per ml range using only minimal quantities of biological matrix.

LC/MS/MS enables rapid and sensitive quantitation of new drug candidates, as well as providing important structural information on metabolites. A full scan LC/MS analysis can initially suggest possible oxidative and/or conjugative metabolic transformations on the basis of the ionic species observed. In the MS/MS mode, the instrument can be tuned to a selected precursor ion of interest, which is then further fragmented to form productions that uniquely identify the metabolic (production scan).

Selectivity can be further enhanced by the quadrupole ion trap, a device that "traps" ions in a space bounded by a series of electrodes. The unique feature of the ion trap is that an MS/MS experiment (or, in fact, multi-step MS experiments) can be performed sequentially in time within a single mass analyzer, yielding a wealth of structural information. Hybrid quadrupole-time-of-flight (Q-TOF) LC/MS/MS systems can also be used for the characterization of metabolite profiles. The configuration of Q-TOF results in high sensitivity in mass resolution and mass accuracy in a variety of scan modes.

Liquid chromatography coupled with nuclear magnetic resonance spectroscopy (LC-NMR) provides a way of confirming absolute molecular configurations. A linear ion-trap mass spectrometer possesses significantly enhanced production-scanning capabilities, while retaining all of the scan functions of a triple quadrupole MS. The ultra-high resolution and sensitivity of Fourier transform ion-cyclotron resonance MS (FI-ICRMS) can be useful for the analysis and characterization of biological mixtures. Data processing and interpretation software packages also enable efficient identification and quantification of metabolites using the tissue-engineered devices of the present invention.

A widely used method to study in vitro drug metabolism is the use of tissue homogenates. The tissues within the three-dimensional systems of the invention can be cultured in the presence of a test agent and harvested to obtain tissue homogenate preparations for use in enzyme analysis. Preparation of tissue homogenates is well known in the art and involves the steps of tissue homogenization and subcellular fractionation to yield two main fractions routinely studied in drug metabolism: the post-mitochondrial supernatant and the endoplasmic reticulum (microsomal) fraction.

For preparation of the post-mitochondrial supernatant, the tissue homogenate can be centrifuged as 12,500×g for 15 minutes to pellet intact cells, cell debris, nuclei and mitochondria. The resultant supernatant (the post-mitochondrial supernatant) is carefully decanted and contains the microsomal plus soluble fractions of the cell. Microsomal tissue fractions can be prepared from the post-mitochondrial supernatant by one of two centrifugation techniques, one involving the use of an ultracentrifuge and the other involving a calcium precipitation of the microsomes at a lower g force.

The ultracentrifugation method uses aliquots (approximately 10-12 ml) of the post-mitochondrial supernatant, which are transferred to ultracentrifuge tubes and centrifuged at 100,000×g for 45 minutes in a refrigerated ultracentrifuge. After centrifugation, the supernatant is decanted and discarded and the microsomal pellet resuspended in a suitable buffer containing physiological concentrations of salt, such as Tris. This procedure yields the final microsomal suspension.

The calcium precipitation method is based on the calcium dependent aggregation of endoplasmic reticulum fragments and subsequent 'low speed' centrifugation of the aggregated microsomal particles. The advantages of this method are that it is less time-consuming and does not require an ultracentrifuge. Aliquots of post-mitochondrial supernatant are mixed with a final $CaCl_2$ concentration of 8 mM and left to stand on ice for 5 min, with occasional gentle swirling.

The mixture is then centrifuged at 27,000×g for 15 min, the supernatant discarded and the pellet resuspended by homogenization in a buffer such as Tris at physiological pH, yielding the microsomal suspension.

The microsomal fractions prepared by both of the above methods may be further washed by resuspending the microsomal pellet in 0.1 M Tris buffer, pH 7.4, containing 0.15 M KCl to remove either adventitious protein or excess $CaCl_2$. The microsomal pellet can then precipitated as above and resuspended in Tris buffer. It is not mandatory to resuspend the final microsomal preparations in Tris buffer and other buffers such as phosphate may be used. When comparing tissue fractions for their ability to catalyze drug biotransformation, a measure of the tissue protein is required. Amongst several methods, protein is readily determined by the colorimetric method of Lowry et al. (1951), with reference to a standard curve of bovine serum albumin. The colored complex is a result of a complex between the alkaline copper-phenol reagent used and tyrosine and tryptophan residues of the protein, and can be detect by spectrophotometer at 705 nm. Other protein detection methods are well known in the art and include the Bradford assay.

Reduced nicotinamide adenine dinucleotide phosphate (NADPH) is often a necessary cofactor for many drug biotransformation reactions and serves as a source of reducing equivalents in the reaction (particularly hydroxylation and demethylation reactions).

Toxicity

There are three general classes of toxicity. Acute toxicity is a toxic effect that occurs after less than about 24 hours of exposure to the drug. Subacute toxicity occurs later, after about 14 to 90 days of exposure to the drug. Chronic toxicity occurs after about 90 days (or longer) exposure to the drug. Current methods in the art are suboptimal for use in detecting subacute and chronic toxicity due to the requirement for extended periods of monitoring in a living subject. While methods of the invention can encompass these longer intervals of exposure, effects may be detected more rapidly, such that the incubation time for the test agent need not be extended. Accordingly, incubation times can range between about 1 hour to 24 hours, or can be extended as necessary for several days or even weeks.

The undesired effects of toxicity caused by administration of a test agent can be screened in several ways. Tissue engineered systems of the invention can be used to determine the range of toxic dosimetry of a test agent. The effect of increasing concentrations of the test agent (i.e., dose) on tissues of interest can be monitored to detect toxicity. A toxic effect, when observed, can be equated with a measurement of test agent concentration/cells $cm^2$. By calculating the toxic concentration according to the distribution of cells in the tissue engineered system, one of skill in the art can extrapolate to the living system, to estimate toxic doses in subjects of various weights and stages in development.

Using methods of the present invention, various doses of individual test agents and combinations of test agents with other pharmaceuticals will be screened to detect toxic effects, including but not limited to irregular metabolism, carcinogenicity and cell death. To detect irregular changes in metabolism, standard methods known in the art for assaying metabolite production, including but not limited to glucose metabolism and enzymatic assays, can be employed. The particular metabolic pathway assayed, or metabolite measured, can vary according to the tissue type selected.

In detecting carcinogenicity, cells can be screened for a transformed phenotype using methods well known in the art, for example, methods detecting changes in gene expression, protein levels, abnormal cell cycles resulting in proliferation and changes in expression of cell surface markers, including, but not limited to, antigenic determinants. Gene expression patterns can be determined, for example, by evaluating mRNA levels of genes of interest according to standard hybridization techniques, such as RT-PCR, in situ hybridization, and fluorescence in situ hybridization (FISH), Northern analysis or microchip-based analysis. Protein expression patterns can be determined by any methods known in the art, for example, by quantitative Western blot, immunohistochemistry, immunofluorescence, and enzyme-linked immunosorbent assay (ELISA), amino acid sequence analysis, and/or protein concentration assays. For details, see Sambrook, Fritsch and Maniatis, Molecular Cloning, A Laboratory Manual, 2nd Ed., Cold Spring Harbor Laboratory Press, 1989. Cell counting and/or separation techniques, such as FACS analysis, can be employed to measure proliferation or detect aberrant cell surface marker expression.

Standard methods well known in the art can also be used to detect cell death, including but not limited to, tunnel assays. Traditional approaches of in vitro toxicology to toxicological screening has been to measure comparatively late events in the process of cell death, such as lactate dehydrogenase release or differential counting of viable and dead cells using vital dyes, such as trypan blue, 4,6-diaminophenylindole (DAPI), propidium iodide, and LIVE/DEAD® stain available from Molecular Probes. Prediction of lethality in vivo is one proposed application of this type of in vitro screen, although cell death is not a common mechanism by which the animal's death is induced following acute exposure to a toxic agent. In contrast, caspase activation is at the center the common features of chronic toxicity, cell death, hyperproliferation and inflammatory reactions. Caspase activity can be measured relatively quickly after a toxic insult (30 min to 4 hr) by fluorescence spectroscopy, thus lending itself to high-throughput screening techniques. Other markers and assays commonly used to monitor apoptosis or necrosis of cells can include, but are not limited to, the presence of phosphatidylserine on the outer leaflet of the plasma membrane of affected cells, annexin V staining, and terminal deoxynucleotidyltransferase nick-end labeling assay (TUNEL).

Using methods of the invention, various doses of individual test agents and combinations of test agents will be screened in panels comprised of tissues having diverse genetic backgrounds to determine the pharmacogenetic toxicity profile of the test agents. For example, multiple doses of, or combinations with, test agents will be screened for toxic effects specific to one or more genetic backgrounds. Toxic effects to be screened for genetic variance include, but are not limited to, irregular metabolism, carcinogenicity and cell death.

Tissue-engineered devices of the present invention can be modified in parallel to generate a comprehensive array of the currently known genetic polymorphisms of different metabolic enzymes. A salient example is the CYP450 monooxygenase system, wherein the population comprises multiple isoforms and polymorphisms that impinge on and complicate predictive models of drug metabolism, drug clearance, and toxicity. For example, in the metabolism of thiopurines, such as thioguanine, the rate-limiting enzyme is a methyltransferase that has different polymorphic forms. Polymorphism in the methyltransferases is known to affect metabolism of the thiopurines. Where the polymorphism gives rise to slower metabolism of the thiopurine, clinical benefit is decreased and where the polymorphism gives rise to an increased rate of metabolism, toxicity can result. Thus, methods of the invention can be used to determine the metabolic profile of various test agents in the presence of various polymorphic forms of an enzyme, such as methyltransferase.

In testing for differential toxicity due to polymorphic variation, or other genetic defects, genetically engineered cells comprising gene knockouts or knock-ins of specific enzymes known to affect drug metabolism and toxicity can be used in the systems of the invention. Cells can be modified using techniques that are known to the skilled artisan, such as RNA interference (RNAi), antisense technology, ribozymes, site-directed mutagenesis, among others.

Efficacy

Efficacy can be detected by measuring individual parameters associated with the repair, enhancement, improvement and/or regeneration of a disease model comprising an injured tissue grown in a three-dimensional system of the invention. In disease models of the invention, the injury can be induced or can be the result of a pre-existing condition in the tissue donor, including conditions relating to inherited genetic abnormalities. Either the induced or pre-existing condition can comprise a weakened state resulting from a previous drug exposure. Test agents, or combinations of test agents, can be analyzed for efficacy in disease models of the invention.

In one embodiment, selected tissues of interest can be treated with agents known in the art to cause cellular damage (e.g., toxins, mutagens, radiation, infectious agents and chemical agents), inducing injury in the tissue. In another embodiment, selected tissues of interest can be altered using standard recombinant techniques to induce a disease state. For example, techniques of homologous recombination can be used to insert a transgene into a cell, or "knock-out" gene expression of a gene of interest. For a review of homologous recombination, see Lewin, B., *Genes V*, Oxford University Press, New York, 1994, pp. 968-997; and Capecchi, M., (1989) Science 244:1288-1292; Capecchi, M., (1989) Trends Genet. 5 (3):70-76. In another embodiment, the selected tissue of interest is injured as a result of an inherited genetic defect, which can be a single gene defect or a multifactorial defect. For a discussion of inherited disorders, see Thompson, McInnes and Willard, Genetics in Medicine, $5^{th}$ Ed., W.B. Saunders Company, 1991.

Tissue engineered systems of the invention can be used to determine the range of effective dosimetry of a test agent. The effect of increasing concentrations of the test agent (i.e., dose) on tissues of interest can be monitored to detect efficacy. A therapeutic effect, when observed can be equated with a measurement of concentration/cells $cm^2$. By calculating the effective concentration according to the distribution of cells in the tissue engineered system, one of skill in the art can extrapolate to the living system, to estimate therapeutic doses in subjects of various weights.

Using methods of the invention, various doses of individual test agents and combinations of test agents will be screened in panels comprised of tissues having diverse genetic backgrounds to determine the pharmacogenetic efficacy profile of the test agents. For example, multiple doses of, or combinations with, test agents will be screened for efficacy, or the lack thereof, specific to one or more genetic backgrounds.

Tissues of Interest

Methods of the invention can be carried out using tissues of any kind. The following description provides specific information relating to five preferred embodiments of the invention.

1. Liver

A. Toxicity

The liver plays a major role in carbohydrate metabolism by removing glucose from the blood, under the influence of the hormone insulin, and storing it as glycogen. When the level of glucose in the blood falls, the hormone glucagon causes the liver to break down glycogen and release glucose into the blood. The liver also plays an important role in protein metabolism, primarily through deamination of amino acids, as well as the conversion of the resulting toxic ammonia into urea, which can be excreted by the kidneys. In addition, the liver participates in lipid metabolism by storing triglycerides, breaking down fatty acids, and synthesizing lipoproteins. The liver also secretes bile, which helps in the digestion of fats, cholesterol, phospholipids, and lipoproteins.

Analysis of metabolic function will indicate toxicity in liver. Thus, in liver tissue engineered systems of the invention, metabolic assays to detect toxicity of a particular test agent are preferred. Metabolic enzymes, including but not limited to, cytochrome P450, alkaline phosphatase, glycolytic enzymes such as α-galactosidase, β-galactosidase, α-glucosidase, β-glucosidase, α-glucuronidase, β-glucuronidase, and α-amylase, NADPH-cytochrome P450 reductase, cytochrome $b_5$, N-demethylase, O-demethylase, acetylcholinesterase, pseudocholinesterase, among other esterases, epoxide hydrolase, amidases, Uridine diphosphate (UDP)-glucuronosyltransferases, phenol sulfotransferase, alcohol sulfotransferase, sterid sulfotransferase, and arylamine sulfotransferase, UDP-glycosyltransferases, purine phosphoribosyltransferase, N-acetyltransferases, glutathione S-transferase, phenylethanolamine N-methyltransferase, non-specific N-methyltransferase, imidazole N-methyltransferase, catechol-O-methyltransferase, hydroxyindole-O-methyltransferase, and S-methyltransferase, alcohol dehydrogenase, aldehyde dehydrogenase, xanthine oxidase, amine oxidases such as monoamine oxidases, diamine oxidases, flavoprotein N-oxidases, and hydroxylases, aromatases, cysteine conjugate β-lyase, and alkylhydrazine oxidase can be tested for metabolic activity using assays well known in the art (this is described in great detail in other portions of the application). Cytochrome p450 enzymes that can be tested include, but are not limited to, CYP1A1, CYP1A2, CYP2A3, CYP2B6, CYP2B7, CYP2B8, CYP2C8, CYP2C9, CYP2C10, CYP2D6, CYP2D7, CYP2D8, CYP2E1, CYP2F1, CYP3A3, CYP3A4, CYP3A5, and CYP4B1.

In a preferred embodiment, the test agent comprises antiviral activity, most preferably, antiviral activity against hepatitis. Currently, there is a great need for safe and effective treatments for hepatitis (Mutchnick, M. G., et. al., Antiviral Research (1994) 24:245-257). For example, clinical tests on the use of the nucleoside analog fialuridine (FIAU) for treatment of chronic hepatitis B were suspended recently due to drug-related liver failure leading to death in some patients. Test agents demonstrating efficacy against hepatitis can also be screened for acute, subacute and chronic toxicity by monitoring metabolic function, preferably of metabolic function of cytochrome P450 and alkaline phosphatase, following administration.

B. Efficacy

Test agents can be screened for efficacy in tissue engineered systems of the invention comprising liver cells affected with diseases including, but not limited to, cancer, diabetes, acute hepatitis, fulminant hepatitis, chronic hepatitis, hepatic cirrhosis, fatty liver, alcoholic hepatopathy, drug induced hepatopathy (drug addiction hepatitis), congestive hepatitis, autoimmune hepatitis, primary biliary cirrhosis and hepatic porphyria, and pericholangitis, sclerosing cholangitis, hepatic fibrosis and chronic active hepatitis, which have been reported to occur with a high frequency as complications of inflammatory bowel diseases such as ulcerative colitis and Crohn's disease.

Preferably, test agents will assayed for their ability to reduce or prevent of progress of hepatic necrocytosis and/or accelerate hepatic regeneration. For example, expression levels of Rasp-1, a gene that is upregulated during regeneration of liver tissue, can be monitored following administration of a test agent. Rasp-1 is described in U.S. Pat. No. 6,027,935, the contents of which are incorporated herein by reference for their description of Rasp-1 sequences, antibodies and assays.

In a preferred embodiment, test agents are screened for efficacy in the treatment of hepatitis viral infections, particularly infections of hepatitis B and hepatitis C. Other hepatitis viruses that are significant as agents of human disease include hepatitis A, hepatitis delta, hepatitis E, hepatitis F, and hepatitis G (Coates, J. A. V., et. al., Exp. Opin. Ther. Patents (1995) 5 (8): 747-756). The test agent can comprise, for example, nucleoside analog antivirals, immunomodulators, immunostimulators (e.g., interferons and other cytokines) or other immune system-affecting drug candidates, including, but not limited to, thymic peptides, isoprinosine, steroids, Schiff base-forming salicylaldehyde derivatives such as Tucaresol, levamisol, and the like (Gish, R. G., et al., Exp. Opin. Invest. Drugs (1995) 4 (2):95-115; Coates, J. A. V., et al., Exp. Opin. Ther. Patents (1995) 5 (8):747-765).

Anti-hepatitis efficacy of a test agent can be determined according to methods known in the art. For example, following treatment with a test agent, the amount of hepatitis virus or viral DNA in the culture medium can be determined by PCR analysis (e.g., of sedimented particles). DNA measurements can be correlated with viral replication to assess post-treatment infectivity. Alternatively, viral loads can be measured directly. Other measures of efficacy include measurement of enzyme levels, including but not limited to SGOT, ALT and LDH, histologic analysis and normal production of total liver proteins, such as the clotting factors.

In a preferred embodiment, the efficacy of a test agent is determined in liver tissues infected with the hepatitis C virus.

In a preferred embodiment, test agents are screened for efficacy in the treatment of liver cancer. Reduction or elimination of transformed liver cells in response to treatment with a test agent can be detected by measuring decreases in hypercalcaemia and CEA expression. Reduction in proliferation can also be determined by cell counting.

C. Combination Three-Dimensional Systems

Three-dimensional systems of the invention can be connected in series to evaluate drug toxicity and efficacy in multiple systems. Preferably, the combination three-dimensional system would comprise a liver unit. Even more preferred is a combination system that comprises an interconnected liver unit and kidney unit. Thus, the effect of a test agent administered to the liver unit can additionally be assayed for its direct and/or indirect effect on the kidney unit. Most preferred is a combination system that comprises an interconnected liver unit, kidney unit and cardiac unit.

2. Kidney

A. Toxicity

Toxicity in the kidney can occur, for example, as a result of allergic or hypersensitive immune responses to a test agent. The appearance of excess protein, such as albumin and creatinine, in the urine is indicative of toxicity. Thus, in kidney tissue engineered systems of the invention, assays to detect toxicity of a particular test agent preferably comprise measurement of proteins including, but not limited to albumin and creatinine.

B. Efficacy

The kidney is a complex organ with an intricate vascular supply and at least 15 different cell types, which performs the critical functions of filtration, reabsorption and excretion. The basic functional unit of the kidney, the nephron, is composed of a vascular filter, the glomerulus, and a resorptive unit, the tubule. Filtration is dependent on flow and specialized glomerular endothelial cells. The majority (50-65%) of reabsorption is performed by the proximal tubule cells using active sodium transport through the energy-dependent $Na^+$—$K^+$-ATPase located on the basolateral membrane. Only 5-10% of the approximately one million nephrons in each human kidney is required to sustain normal excretory function.

Test agents can be screened for efficacy in tissue engineered systems of the invention comprising kidney cells affected with diseases including, but not limited to, glomerulonephritis, ischemia reperfusion injury; bacterial and viral glomerulonephritides, IgA nephropathy and Henoch-Schonlein Purpura, membranoproliferative glomerulonephritis, membranous nephropathy, Sjogren's syndrome, diabetic nephropathy, nephrotic syndrome (minimal change disease, focal glomerulosclerosis and related disorders), acute renal failure, acute tubulointerstitial nephritis, pyelonephritis, genetic renal disease (medullary cystic, medullary sponge, polycystic kidney disease (autosomal dominant polycystic kidney disease, autosomal recessive polycystic kidney disease, tuborous sclerosis), von Hippel-Lindau disease, familial thin-glomerular basement membrane disease, collagen III glomerulopathy, fibronectin glomerulopathy, Alport's syndrome, Fabry's disease, Nail-Patella Syndrome, congenital urologic anomalies), monoclonal gammopathies (multiple myeloma, amyloidosis and related disorders), febrile illness (familial Mediterannean fever, HIV infection), inflammatory disease (systemic vasculitides, polyarteritis nodosa, Wegener's granulomatosis, polyarteritis, necrotizing and crescentic glomerulonephritis), bacterial infection, allergies and congenital defects.

The kidney is able to repair damage to the proximal tubule epithelium through a complex series of events involving cell death, proliferation of surviving proximal tubule epithelial cells, formation of poorly differentiated regenerative epithelium over the denuded basement membrane, and differentiation of the regenerative epithelium to form fully functional proximal tubule epithelial cells (Wallin et al., Lab. Invest. 66:474-484, 1992; Witzgall et al., Mol. Cell. Biol. 13:1933-1942, 1994; Ichimura et al., Am. J. Physiol. 269: F653-662, 1995; Thadhani et al., N. Engl. J. Med. 334:1448-1460, 1996). KIM genes are upregulated in renal tissue after injury to the kidney, during kidney regeneration. KIM genes are described in U.S. Pat. No. 6,664,385, the contents of which are incorporated herein by reference for their description of DNA sequences, antibodies and assays. Preferably, test agents will assayed for their ability to reduce or prevent of progress of renal failure and/or accelerate renal regeneration. For example, expression levels genes that are upregulated during regeneration of kidney tissue, such as the KIM genes, can be monitored following administration of a test agent. As another example, total protein levels, albumin levels, restored sodium, and clearance of creatinine can be monitored following administration of a test agent. Clearance of tracer molecules, such as inulin, diethylene-triaminepentaacetic acid and $^{99m}Tc$ can also be monitored as indicator of the clearance of other molecules following administration of a test agent.

3. Heart

A. Toxicity

The toxic effect of a test agent in cardiac tissue engineered systems of the invention can be detected using a variety of assays known in the art. For example, assays to detect toxicity of a particular test agent preferably comprise measurement of QT intervals, changes in electrophysiology (e.g., changes in $K^+/Ca^{2+}$ channels) and/or arrhythmia by T-wave alternans (TWA).

Alternans of the electrocardiogram is defined as a change in amplitude and/or morphology of a component of the ECG that occurs on an every-other-beat basis (Walker, M. L. and Rosenbaum, D. S., (2003) Cardiovasc. Res. 57: 599-614). TWA is the beat-to-beat alternation of T-wave amplitude, and is closely linked to electrical instability in the heart. Beat-to-beat microvolt fluctuation of the T wave can be detected using high-resolution electrodes and signal processing techniques (Gold, M. R., and Spencer, W. (2003) Curr. Opin. Cardiol. 18: 1-5). A large number of beats, generally 128, are sampled, and the voltages of multiple corresponding points on the T-wave are computed and averaged. Through fast-Fourier transformation, these consecutive amplitudes are displayed spectrally, yielding several frequency peaks. These peaks correspond to thoracic excursions with respiration, other repetitive body movements, and ambient electrical noise. The peak at 0.5 cycles/beat, if present, is caused by TWA. The alternans magnitude, $V_{alt}$, represents the difference between the even or odd beat and the mean amplitude, in microvolts. A threshold of 1.9 uV is used for significance. The alternans ratio (k) is another parameter measured and represents the ratio of the alternans amplitude to the SD of the background noise. It is required to be greater than 3.0 for significance. Additionally, TWA must be sustained for more than one minute.

B. Efficacy

Test agents can be screened for efficacy in tissue engineered systems of the invention comprising cardiac cells affected with diseases including, but not limited to, congestive heart failure, coronary artery disease, myocardial infarction, myocardial ischemia, effects of atherosclerosis or hypertension, cardiomyopathy, cardiac arrhythmias, muscular dystrophy, muscle mass abnormalities, muscle degeneration, myasthenia gravis, infective myocarditis, drug- and toxin-induced muscle abnormalities, hypersensitivity myocarditis, autoimmune endocarditis, and congenital heart disease. Preferably, test agents will assayed for their ability to accelerate cardiac regeneration. In general, efficacy can be indicated by detection of improved contractility, electromechanical conduction and/or association, susceptibility to electrical dysfunction, ventricular fibrillation (sudden death), ionotropy, chronotropy, and decreased leakage of enzymes (e.g., CPK and SGOT).

4. Bone Marrow

A. Toxicity

The toxic effect of a test agent in bone marrow engineered systems of the invention can be detected primarily by monitoring the effect of the agent on stem cell production. Stem cell production can be monitored by methods well known in the art, such as FACS analysis. Stem cells to be monitored include, but are not limited to hematopoietic progenitors, lymphoid progenitors and myeloid progenitors. In addition, the toxic effect of a test agent in bone marrow engineered systems of the invention can be detected by screening for the development of adverse secondary effects, such as B12 deficiency, pernicious anemia and maturation arrest (failure to divide). Bone marrow engineered systems of the invention can also be used as an indicator system for the development of autoimmune responses. Adverse autoimmune responses will result in the production of antibodies against albumin-drug conjugates. Suspected adverse autoimmune responses in patients could be confirmed by assaying for the undesired albumin-drug conjugates in bone marrow engineered systems of the invention.

B. Efficacy

Preferably, test agents of the invention can be screened for their ability to increase or decrease production of specific stem cell progenitors, and the differentiated progeny thereof, including, but not limited to erythrocytes, platelets, neutrophils, T cells, B cells, eosinophils, basophils, neutrophils, and monocytes. Alternatively, test agents of the invention can be screened for their ability to improve the function of suboptimal marrow. For example, improvement in bone marrow proliferation can be monitored by cell counting methods known in the art.

5. Cartilage

A. Toxicity

The toxic effect of a test agent in cartilage tissue engineered systems of the invention can be detected using a variety of assays known in the art. Toxicity in cartilage involves abnormal growth, altered metabolic function (e.g., glucose metabolism), protein production and altered histology. For example, test agents known to have adverse effects on cartilage in developing subjects (e.g., children) comprise a family of anti-bacterial agents known as the fluoroquinolones. Although fluoroquinolones are likely to possess extremely useful anti-microbial properties, they are potentially harmful to cartilage, and must be carefully screened for toxicity. Methods of the invention can be applied to the screening of test agents, such as test agents comprising fluoroquinolones, to identify those that do not cause toxicity in cartilage.

Three-Dimensional Systems of the Invention

Three-dimensional systems of the invention are described in U.S. Ser. No. 10/187,247, filed Jun. 28, 2002; Ser. No. 09/560,480, filed Apr. 28, 2000, now U.S. Pat. No. 6,455,311; U.S. Ser. No. 10/038,891, filed Jan. 2, 2002; and PCT/US03/29880; filed on Sep. 23, 2003, now U.S. Ser. No. 10/528,737, filed Mar. 22, 2005, the contents of which are incorporated herein by reference for their detailed descriptions, figures and examples, which describe the structure and function of three-dimensional tissue engineered systems. Descriptions of these systems are also reiterated below.

Manufacture of Molds and Polymer Scaffolds

For purposes of this invention a "mold" is a device on the surface of which the branching structure of the microchannels is etched or formed. Fabrication of a mold begins by selection of an appropriate substrate. The choice of a substrate material is guided by many considerations, including the requirements placed on the fabrication process by the desired mold dimensions, the desired size of the ultimate template, and the surface properties of the wafer and their interaction with the various cell types, extracellular matrix ("ECM") and polymeric backbone. Also important are the thermal properties, such as the glass transition temperature (Tg), which must be high enough so that the network of pores in the mold does not collapse upon solvent removal.

Molds of the present invention can comprise a variety of materials, including, but not limited to, inert materials such as silicon, polymers such as polyethylene vinyl acetate, polycarbonate, and polypropylene, and materials such as a ceramic or material such as hydroxyapatite. In particular, the mold can comprise from metals, ceramics, semiconductors, organics, polymers, and composites. These materials are either inherently suitable for the attachment and culture of animal cells or can be made suitable by coating with materials described herein to enhance cell attachment and culture (e.g. gelatin, matrigel, vitrogen and other tissue culture coatings known in the art).

In an alternative embodiment, MEMS replica molding can be used to make a "polymer scaffold" for seeding cells. In this method, a mold is made as described herein, preferably of silicon, and is then used as a template on which a polymeric material is cast. Optionally, the polymer scaffold can then be peeled away from the mold and seeded with cells.

A "tissue-defining surface" is the surface of a mold or a polymer scaffold, and a "substrate" is the mold or polymer scaffold itself.

The term "polymer" includes polymers and monomers that can be polymerized or adhered to form an integral unit. The polymer can be non-biodegradable or biodegradable, typically via hydrolysis or enzymatic cleavage. For implantation, polymer scaffolds are preferably used, which can be biodegradable polymer scaffolds. For embodiments relating to extracorporeal support devices, biocompatible, nondegradable polymers may facilitate size reduction.

In one embodiment, the biodegradable polymer scaffold comprises biodegradable elastomers formed from hydrolyzable monomers as described in Wang et al, Nature Biotech 20, 602 (2002), the contents of which are incorporated herein by reference. These biodegradable elastomers are analogous to vulcanized rubber in that crosslinks in a three-dimensional network of random coils are formed. These biodegradable elsatomers are hydrolyzed over time, preferably within 60 days.

Polymer material for implantation should be selected for biocompatibility. Any degradation products should also be biocompatible. Relatively high rigidity is advantageous so that the polymer scaffold can withstand the contractile forces exerted by cells growing within the mold. A biocompatible degradable polymer and its degradation products are non-toxic toward the recipient.

The term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used in reference to polymers, the term "degrade" refers to cleavage of the polymer chain, such that the molecular weight stays approximately constant at the oligomer level and particles of polymer remain following degradation. The term "completely degrade" refers to cleavage of the polymer at the molecular level such that there is essentially complete loss of mass. The term "degrade" as used herein includes "completely degrade" unless otherwise indicated.

Materials suitable for polymer scaffold fabrication include, but are not limited to, poly-dimethyl-siloxane (PDMS), poly-glycerol-sebacate (PGS), polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl fluoride, polyvinyl imidazole, chlorosulphonated polyolifins, polyethylene oxide, polyvinyl alcohol, Teflon®, nylon silicon, and shape memory materials, such as poly(styrene-block-butadiene), polynorbornene, hydrogels, metallic alloys, and oligo(ε-caprolactone)diol as switching segment/oligo(p-dioxyanone)diol as physical crosslink. Other suitable polymers can be obtained by reference to The Polymer Handbook, 3rd edition (Wiley, N.Y., 1989). Combinations of these polymers may also be used.

Polylactide-co-glycolides (PLGA), as well as polylactides (PLA) and polyglycolides (PGA) have been used to make biodegradable implants for drug delivery. See U.S. Pat. No. 6,183,781 and references cited therein. Biodegradable materials have been developed for use as implantable prostheses, as pastes, and as templates around which the body can regenerate various types of tissue. Polymers that are both biocompatible and resorbable in vivo are known in the art as alternatives to autogenic or allogenic substitutes. In a preferred embodiment, polymers are selected based on the ability of the polymer to elicit the appropriate biological response from cells, for example, attachment, migration, proliferation and gene expression.

Solvents for most of the thermoplastic polymers are known, for example, methylene chloride or other organic solvents. Organic and aqueous solvents for protein and polysaccharide polymers are also known. The binder can be the same material as is used in conventional powder processing methods or can be designed to ultimately yield the same binder through chemical or physical changes that occur as a result of heating, photopolymerization, or catalysis.

Properties of the mold and/or polymer scaffold surface can be manipulated through the inclusion of materials on the mold or in polymer scaffold material which alter cell attachment (for example, by altering the surface charge or structure), porosity, flexibility or rigidity (which may be desirable to facilitate removal of tissue constructs). Moreover, advances in polymer chemistry can aid in the mechanical tasks of lifting and folding as well as the biologic tasks of adhesion and gene expression.

For example, molds can be coated with a unique temperature-responsive polymer, poly-N-isopropyl acrylamide (PNIPAAm), which demonstrates a fully expanded chain conformation below 32° C. and a collapsed, compact conformation at high temperatures. When grafted onto surfaces of silicon wafers using electron beam irradiation, it can be used as a temperature switch for creating hydrophilic surfaces below 32° C. and hydrophobic surfaces above 32° C. Since PNIPAAm is insoluble in water over the lower critical solution temperature (LCST about 32° C.) and reversibly solubilized below the LCST, cells detach from the substratum by simply lowering the temperature below the LCST. One of skill in the art can 1) engraft the polymer on silicon wafers that are pre-coated with polystyrene or 2) engraft the polymer on silicon wafers whose surface is first modified by vinyl-tricholorosilane. Either of these techniques will ensure that the polymer is better integrated and conjugated to its substratum (polystyrene in the former case and vinyl groups in the later case) so that it can serve as an effective thermal switch, useful in reversing cell attachment and detachment as a single contiguous layer of cells without the usual cell damage.

Another system for promoting both cellular adhesion and lifting of cells as intact sheets can involve the use of RGD (Arg-Gly-Asp) peptides. The RGD sequence is part of the domain within the fibronectin molecule that endows it with the ability to interact with adhesion molecules present on the cell surface of fibroblasts. Fibronectin itself is a well-characterized extracellular, structural glycoprotein which interacts strongly with other extracellular matrix molecules and which causes the attachment and spreading of most cells. This function of the fibronectin molecule is localized primarily to the RGD sequence. One of skill in the art can synthesize RGD peptides with a structural backbone of PMMA that has an RGD peptide sequence at its tips, bound to one another with the intermediate layering of polyethylene oxide. This allows differential cell adhesion in only selected areas and not others. Once the tissue of desired quality is formed, release of this intact monolayer of tissue from its substratum is straightforward; it requires only the addition of soluble RGD to the culture medium to act as a competitive substrate to the insolubilized RGD substrate on the silicon mold surface.

Attachment of the cells to the mold and/or polymer scaffold can be enhanced by coating the substrate with compounds such as basement membrane components, agar, agarose, gelatin, gum arabic, types I, II, III, IV, and V collagen, fibronectin, laminin, glycosaminoglycans, matrigel, vitrogen, mixtures thereof, and other materials known to those skilled in the art of cell culture.

Thus, by the methods of the invention, cells can be grown on molds that are uncoated or coated as described herein, depending upon the material used for mold construction. Alternatively, cells can be grown on polymer scaffolds made by replica molding techniques.

Design of Apparatus

In a preferred embodiment, mold and/or polymer scaffold pieces are fitted together and optionally separated by a semipermeable membrane. The vascular cells can be seeded into one layer and cultured to form vascular channels based on the pattern etched in the surface of the mold. Organ or tissue specific cells can be added to the second patterned surface, where they attach and proliferate to form a vascularized tissue bilayer. The second patterned surface optionally comprises inlets for neural innervation, urine flow, biliary excretion or other activity.

Channel designs can be incorporated into a matrix, with each design corresponding to a polymer layer arranged in a repeating pattern in three dimensions. Fabrication allows for multiple silicon master molds, each master mold with a different channel design with intervening through-hole layers, rather than having only inlet and outlet layers at opposing diagonal corners, and has a much more complex and dense array of through-holes connecting large numbers of smaller vessels.

FIGS. 1-27 depict the molds, microfabrication of the molds, physiological growth of cells in culture that have been seeded on the microfabricated molds, and configuration of the molds and/or polymer scaffolds into three-dimensional systems.

Construction of Tissue or Organ Equivalents

Engineered tissue lamina can be systematically folded and compacted into a three-dimensional vascularized structure. The two-dimensional surface of the mold can be varied to aid in the folding and compacting process. For example, the surface can be changed from planar to folded accordion-like. It can be stacked into multiple converging plates. It could be curvilinear or have multiple projections.

Different types of tissue, or multiple layers of the same type of tissue, can be superposed prior to folding and compacting, to create more complex or larger structures. For example, a tubular system can be layered onto a vascular system to fabricate glomerular tissue and collecting tubules for kidneys. Bile duct tubes can be overlaid on vascularized liver or hepatocyte tissue, to generate a bile duct drainage system. Alveolar or airway tissue can be placed on lung capillaries to make new lung tissue. Nerves or lymphatics can be added using variations of these same general techniques.

Three-dimensional tissue and organ formation can be achieved by the addition of the second mold or polymer scaffold which allows the functional unit of the organ to be added, and likewise allows precision for patterning of exocrine outflow. For example, in the liver, the parenchymal cells are hepatocytes and the exocrine system is the biliary system. By the addition of the second compartment containing hepatocyes and biliary cells, the functional tissue of the liver can be achieved and biliary excretion can be designed and enfolded.

This patterning can be made more complex with the addition of further layers separated by permeable membranes. Several molds and/or polymer scaffolds, with or without semi-permeable membranes between them, can be stacked in rational arrays to produce complex tissue in 3-dimensional space. These layers of molds and/or polymer scaffolds, and optionally, semi-permeable membranes, can be appropriately interdigitated and connected (e.g. via through-holes) to produce vascular connections through the depths of the stack, as well as excretory outflow systems through the depths of the tracts.

Stacking Molds and/or Polymer Scaffolds to Achieve Three-Dimensionality.

Extension of the two-dimensional technology into the third dimension can be accomplished by stacking the two-dimensional layers on top of each other. This stacking method begins with many molds and/or polymer scaffolds produced by the techniques described in previous sections. Once these molds and/or polymer scaffolds (nominally of the same size) are created, they are lain down or bonded to other separate molds and/or polymer scaffolds, atop one another. The layers are connected at points within small and/or midsized vessels by vertical links, which serve as through-holes extending through the z-axis of the molds and/or polymer scaffolds. The pattern of microchannels on the surface of each mold or polymer scaffold can differ or be similar to the previous layer, depending upon fluid mechanical considerations. Alignment provided by vertical links generates vessel structures that extend up into the third (vertical) dimension.

By extending this technology as needed, one can move from the presently achievable formation of small (~100 cm$^2$) tissue sheets, each containing one plane of blood vessels, to the formation of perhaps 100 cm$^3$ of material, enough to build an organ. The process is low-cost, scalable, can be customized for the physiology of a particular patient, and is based upon currently available microfabrication technology.

Fastening the Stacked Layers.

An aspect of this invention is the fastening or sealing of the polymeric mold layers. Preferably, the layers are irreversibly bound before implantation into the host. Depending on the composition of the layered material, the layers can be sealed by solvent bonding; reflow by heating (40° C.); treating surface with oxygen plasma; or by polymer flow at the surface. Biocompatible polymer materials maybe bonded together by plasma activation to form sealed structures (Jo et al., *SPIE* 3877, 222 (1999)). The basic process results in bonded layers with channel architecture closely resembling that obtained with silicon etched molds.

Silicon-Glass Microfluidic Chambers to Test Sealing of Stacks.

Microfluidic tests have been performed that demonstrate that bonded apparatuses are leakproof and support fluid pressures necessary for dynamic cell seeding. One of the most common methods used to seal micromachined wafers together is anodic bonding, a technique based on the high concentration of mobile ions in many glasses (Camporese, et al., *IEEE Electron. Device Lett. EDL* 2, 61 (1981)). This process produces a permanent seal; fracture testing of silicon-glass anodically bonded interfaces produces a failure within the bulk of the glass.

Etched wafers maybe bonded together, producing closed lumens suitable for fluidic experiments. A fluidic test was performed with a mixed-phase flow of alcohol with 10 μm fluorescent microspheres. An unetched glass-capping layer was mechanically drilled for inlet and outlet fluid ports, and then anodic ally bonded to a silicon wafer plasma-etched with the TEP-1-geometry. A permanent seal with no leaks was produced, enabling one to obtain highly accurate pressure and flow data.

Alternatively, the multilayer device of the invention can be configured such that each of the layers has an alignment indentation on one surface of the layer and an alignment protrusion on the opposing surface of another layer. The alignment indentations shaped to mate with the alignment protrusion, so that the layers are held together.

Alternative Methods of Stacking.

To build up the mold and/or polymer scaffold layers by mechanical assembly, the layers can be mechanically mated using biodegradable or non-biodegradable barbs, pins, screws, clamps, staples, wires, string, or sutures (See U.S. Pat. No. 6,143,293). With this mechanical assembly approach, each prefabricated section can comprise different mold and/or polymer scaffold material and/or different mold microstructures. Different sections of these can be seeded with cells before assembly. Cells thus be can be embedded into the mold or polymer scaffold by assembling sections around these components. In addition, surface features on each mold, which are readily fabricated, become part of the internal microstructure (e.g., molded surface channels become conduits for cell infusion, or for blood flow to stimulate angiogenesis). A surface feature on an individual mold or polymer scaffold will become an internal feature when another segment is assembled over it. For example, surface features such as channels can be micromachined into a first mold or polymer scaffold layer. When a second mold or polymer scaffold layer is placed atop that a first layer, the micromachined surface feature becomes an internal feature of the apparatus.

Rolling or Folding to Achieve Three-Dimensionality

An alternate method for achieving three-dimensionality is to generate a long strip of polymer mold material, which contains repeating units of the blood vessel network along with through-holes, and to fold the mold film in a z-fold fashion while aligning the through-holes to one another.

The rolling or folding process begins with the generation of a lengthy strip of polymer mold material, which contains a serial array of unit cells each of which is comprised of an array of channels mimicking the vascular network, produced from a wafer mold by molding, embossing, or the like. These unit cells can be identical or can be different. The units are linked to through-holes that provide the vertical channel connections between horizontal blood vessel layers. Once the polymeric scaffold strip has been formed, it is folded in a z-fold fashion, and bonded together so that each fold is attached to the film portions above and below it with alignment to the through-holes.

This roll can be of a length to provide sufficient scaffolding material for an entire human organ, which can be hundreds or even more multiples of the area of a single wafer. Each section of the roll is a sheet of polymeric mold with closed lumens, or vessels. The vessels in each folded section of sheet are connected to a through-hole at the edge of the sheet (for example, one on each side, for inlet and outlet blood flow). During folding, the sheet sections are folded such that the through-hole openings align, forming a vessel in the third (z) dimension. The roll can be in the shape of a spiral, helix, jelly roll or other cylindrically shaped objects.

The described three-dimensional tissue structures can then be implanted into animals or patients by directly connecting the blood vessels to flow into and out of the apparatus. Immediate perfusion of oxygenated blood occurs, which allows survival and function of the entire living mass.

In a one embodiment, tissue-engineered liver is formed. Preferably, tissue engineered liver comprises both functioning hepatocytes and bile ducts. The biliary system of native liver begins with a minute hexagonal bile canaliculus, which is formed from specialization of the adjacent surfaces of individual hepatocytes, which are sealed with tight junctions. These canaliculi are confluent with terminal biliary ductules, which are initially made of squamous cells, but give way to low cuboidal biliary epithelium as they approach the interlobular bile ducts. One liter of bile per day is secreted by hepatocytes and moved out of the liver through this system. There have been previous reports of the formation of duct-like structures in a variety of long-term in vitro and in vivo hepatocyte cultures (Block, et al., *J Cell Biol,* 132, 1133 (1996); Landry, et al., *J Cell Biol,* 101, 914 (1985); Mitaka, et al., *Hepatology* 29, 111 (1999); Nishikawa, et al., *Exp Cell Res,* 223, 357 (1996); Uyama, et al., *Transplantation* 55, 932 (1993)).

In a yet another embodiment, tissue-engineered kidney is formed. Preferably, tissue engineered kidney comprises functioning proximal tubules. Tissue-engineered kidney functions as a native kidney; glomerular ultrafiltrate can flow from the glomerular endothelium and passes through a semipermeable membrane into a proximal tubule network where reabsorption occurs.

System for Modeling and Designing Physiological Networks

Three-dimensional systems of the invention can comprise a physiological fluidic network having stacked, two-dimensional layers comprised of blood vessels, wherein small and/or midsized vessels in one layer are vertically connected to small and/or midsized vessels in at least one additional layer by vertical links. Methods of integrating the two dimensional networks, in which small and midsized vessels are arranged to link the networks vertically in a more complex manner, enable high cell densities and a large number of small vessels to be incorporated into the three-dimensional structure of the tissue engineered constructs.

These three-dimensional designs comprise stacked, folded or rolled series of two-dimensional layers, with the two-dimensional layers arranged such that large numbers of interconnection points exists between layers. Each two-dimensional layer is generated by using a computational fluid dynamic (CFD) model, which produces a model network to simulate the critical structure and function of the tissue or organ of interest. The CFD model generates multiple, preferably at least two, distinct two-dimensional layers, which are arranged to allow for a very large number of vertical interconnects between layers. Within each two-dimensional layer, unit cells are arranged in a hexagonal pattern, and the thickness of each line in the pattern corresponds to the width of the fluidic channel.

The resulting three-dimensional structure is comprised of a large number of two-dimensional layers, arranged in a repeating fashion, and are stacked vertically in a total stack of at least 15 layers. This design can comprise between about 50 and 2000 layers, more preferably between about 100 and 1000 layers and most preferably about 500 layers. Advantageously, such designs have increased space in the lateral dimension, enabling a much larger number of small channels. It enables at least one order of magnitude but not more than two orders of magnitude increase in the number of small channels.

Preferably, the tissue engineered constructs have a small vessel or capillary capacity in an amount greater than about 2000 capillaries/cc, greater than about 5000 capillaries/cc, greater than about 10,000 capillaries/cc, greater than about 15,000 capillaries/cc, up to about 100,000 capillaries/cc. Most preferably, the tissue engineered constructs having a small vessel or capillary capacity in an amount equal to or greater than about 10,000 capillaries/cc. Tissue engineered constructs of the present invention can maintain physiological pressure and fluid velocities in the network, maximum oxygen diffusion length, and vessel size distribution, which for small vessels is between about 100-200 microns. Blood vessels of all sizes are oriented along all three axes and along all angles in between. Simultaneous matching of all physiological parameters results from organization of tissues in a true three-dimensional coordinated fashion.

Figure 28:
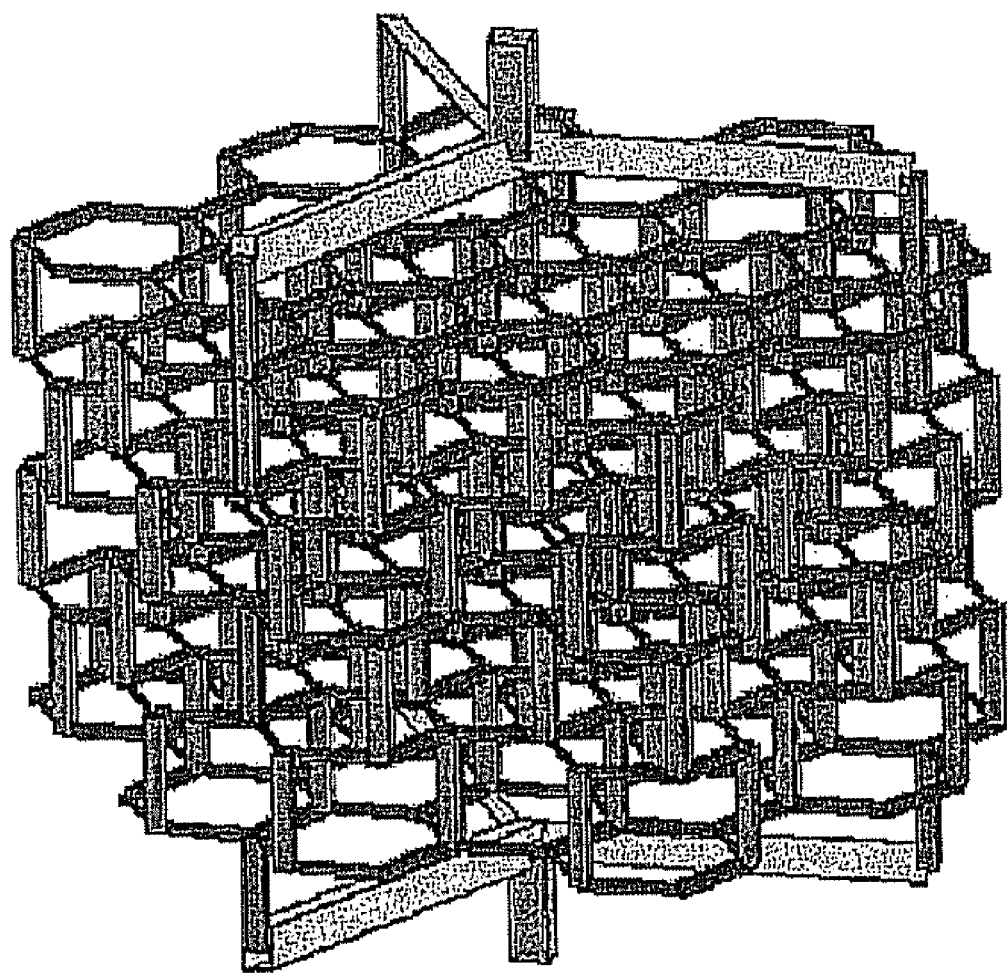
FIG. 28 shows a three-dimensional network having a very large number of vertical interconnects between layers.

Three-dimensional systems of the invention can comprise a physiological fluidic network having stacked, two-dimensional layers comprised of blood vessels, wherein small and/or midsized vessels in one layer are vertically connected to small and/or midsized vessels in at least one additional layer by vertical links (FIG. 28). In a preferred embodiment, the tissue engineered construct has a small blood vessel capacity of at least about 10,000 capillaries/cc and the distance between small blood vessels is less than about 200 microns.

As used herein, the term "vessel" and blood vessel" are interchangeable.

A "small vessel" or "capillary" refers to a blood vessel that is less than 20 microns in diameter.

A "midsized vessel" refers to a blood vessel that is between 20 and 100 microns in diameter.

"Physiological" refers to the condition of a blood vessel within a normal living system. In context, "physiological" can also refer to the condition of a tissue or organ within a normal living system. A "condition" refers to one or more parameters, such as pressure, velocity and capacity of blood flow, shear wall stress, hematocrit distribution and distance between vessels, which for small vessels is between about 100-200 microns. Data from two physiological systems are described in Kassab et al, Am. J. Physiol 265 (1): H350 (1993) and Kassab, Ann Biomed Eng 28 (8): 903 (2000), the contents of which are incorporated herein by reference.

A "vertical link" refers to a partial or complete through hole within one layer that vertically connects at least one second layer. Vertical links are perpendicular to the layers which they connect. An "inlet" or "outlet" refers to the placement of tubing within a through hole.

A system for modeling and designing physiological networks can be embodied, in whole or in part, in a software program to be executed by a general purpose computing device and/or a specific purpose device having embedded instructions for performing tasks included in said system. For illustrative purposes, the invention will be described as embodied in software programs executed using a general purpose computing device.

Figure 29:
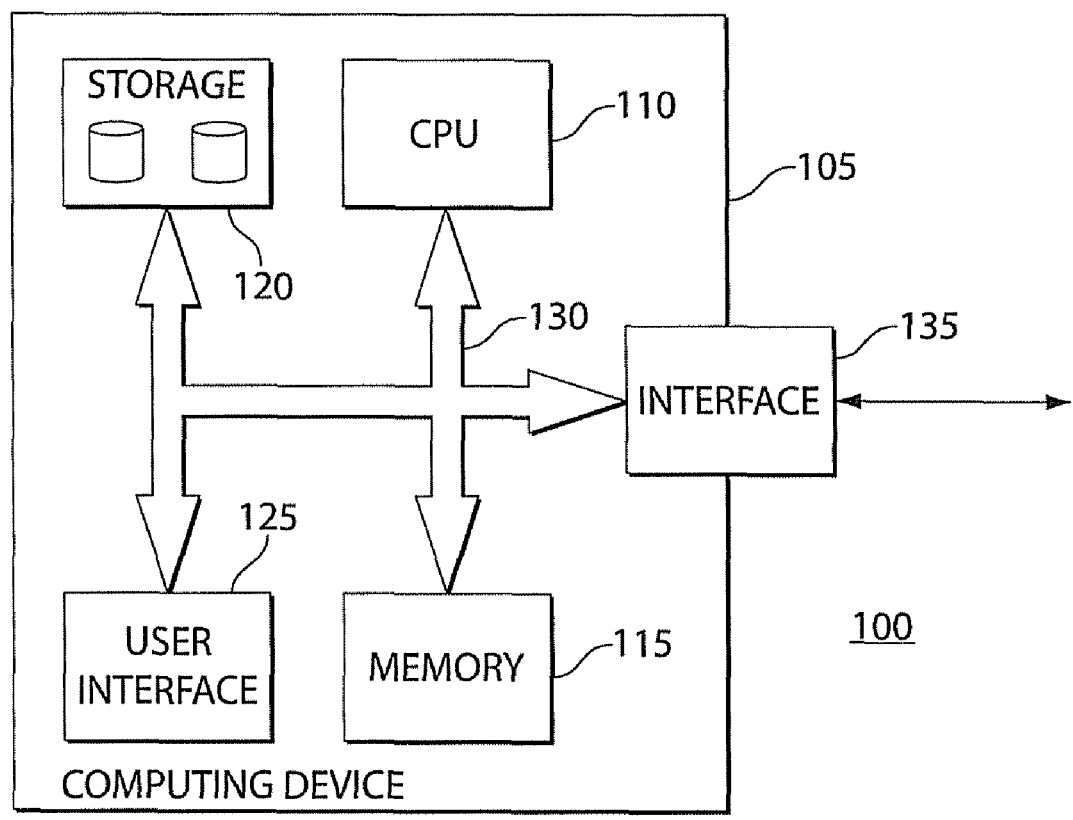
FIG. 29 is a diagram illustrating a system for designing and modeling fluidic networks.

FIG. 29 is a diagram illustrating a system configuration 100. As shown in FIG. 29, system 100 may comprise a computing device 105, which may be a general purpose computer (such as a PC), workstation, mainframe computer system, and so forth. Computing device 105 may include a processor device (or central processing unit "CPU") 110, a memory device 115, a storage device 120, a user interface 125, a system bus 130, and a communication interface 135. CPU 110 may be any type of processing device for carrying out instructions, processing data, and so forth. Memory device 115 may be any type of memory device including any one or more of random access memory ("RAM"), read-only memory ("ROM"), Flash memory, Electrically Erasable Programmable Read Only Memory ("EEPROM"), and so forth. Storage device 120 may be any data storage device for reading/writing from/to any removable and/or integrated optical, magnetic, and/or optical-magneto storage medium, and the like (e.g., a hard disk, a compact disc-read-only memory "CD-ROM", CD-ReWritable "CD-RW", Digital Versatile Disc-ROM "DVD-ROM", DVD-RW, and so forth). Storage device 120 may also include a controller/interface (not shown) for connecting to system bus 130. Thus, memory device 115 and storage device 120 are suitable for storing data as well as instructions for programmed processes for execution on CPU 110. User interface 125 may include a touch screen, control panel, keyboard, keypad, display or any other type of interface, which may be connected to system bus 130 through a corresponding input/output device interface/adapter (not shown). Communication interface 135 may be adapted to communicate with any type of external device, system or network (not shown), such as one or more computing devices on a local area network ("LAN"), wide area network ("WAN"), the internet, and so forth. Interface 135 may be connected directly to system bus 130, or may be connected through a suitable interface (not shown).

While the above exemplary system 100 is illustrative of the basic components of a suitable system, many variations of the hardware configuration are possible. As described above, system 100 provides for executing processes, by itself and/or in cooperation with one or more additional devices, that may include programs for modeling and designing physiological networks according to flow parameters in accordance with the present invention. System 100 may be programmed or instructed to perform these processes according to any communication protocol, programming language on any platform. Thus, the processes may be embodied in data as well as instructions stored in memory device 115 and/or storage device 120 or received at interface 135 and/or user interface 125 for execution on CPU 110. Exemplary processes will now be described in detail.

Overview of Design Method

Software tools executed on system 100 may be used to design fluidic networks appropriate for use as vasculatures in tissue engineered organs. A fluidic network may be considered appropriate for use in tissue-engineered organs if the network mimics vital behavior of natural vasculatures. Two kinds of measurable data on blood vessel networks in nature may be used for evaluating a fluidic network: measurements of the geometry of blood vessels, and measurements of the blood flow behavior in the vessels. Measurements of the geometry of the blood vessels may include vessel diameters, vessel lengths, and the branching pattern of the network. Measurements of the blood flow behavior may include flow velocities, fluidic pressures, and forces exerted by the fluid shearing against the vessel wall.

The flow behavior in a single blood vessel may be modeled by a single equation. The equation used may vary depending on the type of vessel and type of fluid in question. A network of blood vessels may be modeled by a system of equations, where each vessel is represented by a single equation. There may be overlap in the equations: for example, if two vessels are connected, the amount of fluid flowing through one (the flow rate) will equal the amount of fluid flowing into the other. The equations are thus interrelated, and this type of system is known as a system of "simultaneous" equations. More equations may be added to the system to represent constraints on the network, such as requiring that two vessels have the same flow rate. Thus, a fluidic network having thousands of individual vessels may be described by a system of thousands of simultaneous equations.

A software program for use with system 100 may include steps as follows: receiving a branching pattern, indicating how many vessels there are, how they are connected to each other, and how large the tissue or organ supported by the fluidic network is. The system may set up an equation for each vessel, keeping track of how the equations are related to each other. The system may need more information to solve all of the equations. If the geometry is provided to the system, indicating the length and diameter of each vessel, the software can solve the system and determine the flow behavior throughout the network. Furthermore, with flow velocities and pressure, the software can solve the system and provide an optimal diameter for each vessel.

Figure 30:
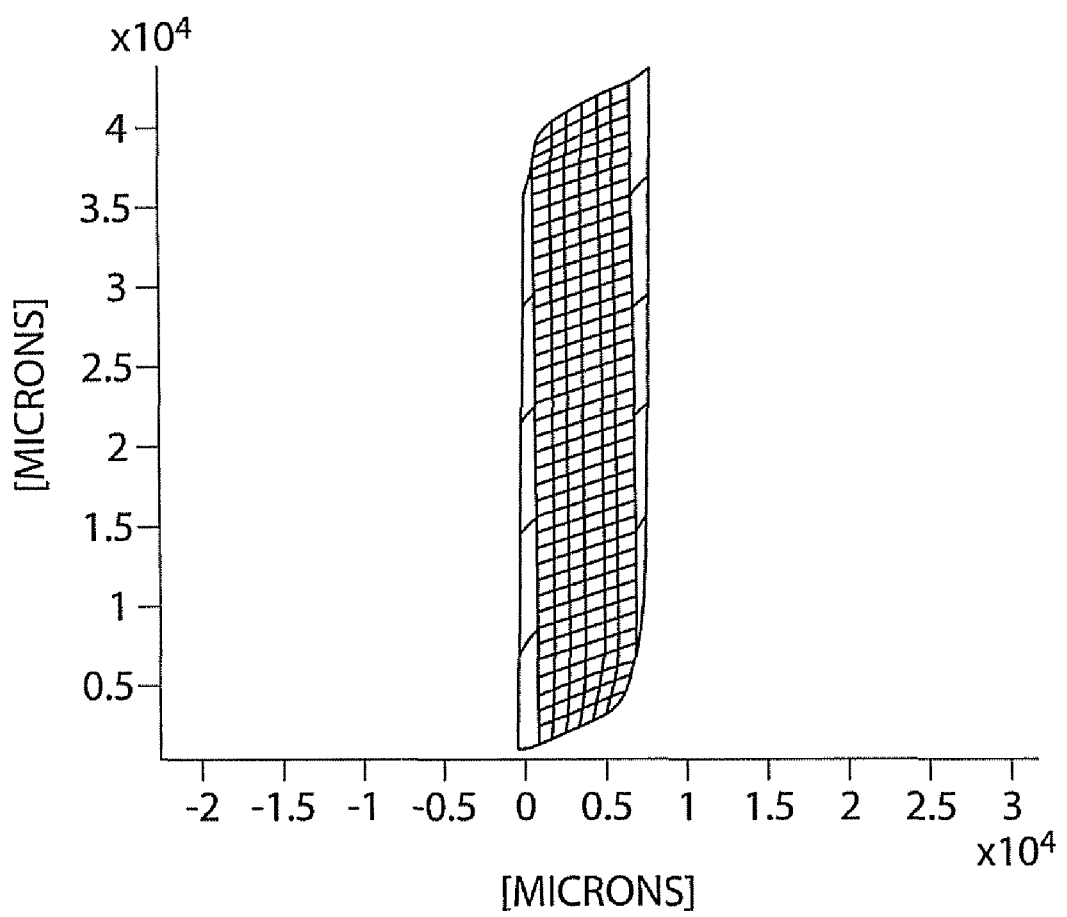
FIG. 30 illustrates a network, referred to as Testnet-0.

A combination of geometry and flow behavior may be used: for a branching pattern, flow may be distributed evenly throughout the network; and limits on the pressures and flow rates may be placed on the network. FIG. 30 illustrates a network designed using this method.

The technique described above accounts for each vessel by a single equation and the entire system of equations can be solved at once. The single equation for each vessel assumes that the fluid in the vessel is behaving as a simple fluid. Blood, however, may be modeled as something other than a simple fluid: cells and other materials that affect flow properties may also be taken into account.

Therefore, a program may be provided to accurately model the flow of blood in networks and to account for these factors. Including these effects expands the system of equations from thousands of equations to hundreds of thousands of equations, and advanced techniques may be required to solve a system of this size.

Physiological Network Topology

In a blood vessel network, vessels larger than ~20 μm in diameter may show a treelike topology. That is, a large vessel may divide into two or more smaller vessels. Blood vessels smaller than ~20 μm, including the capillaries, may be arranged in bundles, where a number of vessels of the same size are interconnected. The topology of a vasculature network can be described using a numbering system. In accordance with an embodiment of the invention, a diameter-defined Strahler ordering system can be used (Jiang et al., Journal Of Applied Physiology 76 (2):882 (1994), the contents of which are incorporated herein by reference). In this system, vessels may be given order numbers, where the smallest vessels are order 0 and the larger vessels have higher numbers. Useful information can be extracted from the ordered network, such as which order vessels are likely to be connected to each other and how many vessels of each order exist in the network.

Physiological Flow Behavior

There are several properties the flow through a vasculature may need to satisfy in order to support a living organ. Basic requirements of a vascular network may include:
1. allowing cells to be seeded on the inside of the vessels;
2. providing nutrient transport to and from all parts of the tissue being supported; and
3. being able to be implanted without disturbing blood flow to other organs.

From each basic requirement more specific required characteristics of the network can be derived:
1. The process of seeding cells on the inside of the vessels and the behavior of those cells may be highly dependent on the shear stresses applied by the fluid at the wall. A network may be generated such that the shear throughout the network is constant to give uniform seeding and growth. This is consistent with hypothetical and experimental investigations of physiological vasculature.
2. The network may include a sufficient number of vessels distributed throughout the volume of the tissue to provide nutrient transport throughout the organ. The distribution of various-sized vessels has been measured in numerous physiological systems, and a network may be generated to match the physiological distribution.
3. The network may be generated such that conditions at the boundary match those of the network being replaced, thus allowing implantation without disturbing blood flow to other organs. The boundary conditions are the pressure drop across the network and the total flow rate through the network. These values have been measured for various organs in numerous animals.

A vasculature design satisfying the above-listed criteria may be used to support a living organ.

Device Topology Design

The first step of designing a fluidic network is to specify a network topology. Networks may be described using a node-vessel form often used to describe networks of electrical resistors. This format may consist of a list of nodes and a list of vessels. In the list of nodes, an x, y, and z location is assigned to each node. For n nodes the list may be:

$$Nodes = \begin{vmatrix} 1 x_1 y_1 z_1 \\ 2 x_2 y_2 z_2 \\ \vdots \\ n x_n y_n z_n \end{vmatrix}. \quad (1)$$

A vessel connects two nodes, so in the list of vessels each vessel may be defined by the two nodes at its ends. For m vessels:

$$Vessels = \begin{vmatrix} 1 \; node_{1a} \; node_{1b} \\ 2 \; node_{2a} \; node_{2b} \\ \vdots \\ m \, node_{ma} \, node_{mb} \end{vmatrix}, \quad (2)$$

where $node_{ia}$ is the node at one end of vessel i and $node_{ib}$ is the node at the other end. Such a network may be created and manipulated in a programming environment on system 100, such as Matlab® and the like.

Figure 31:
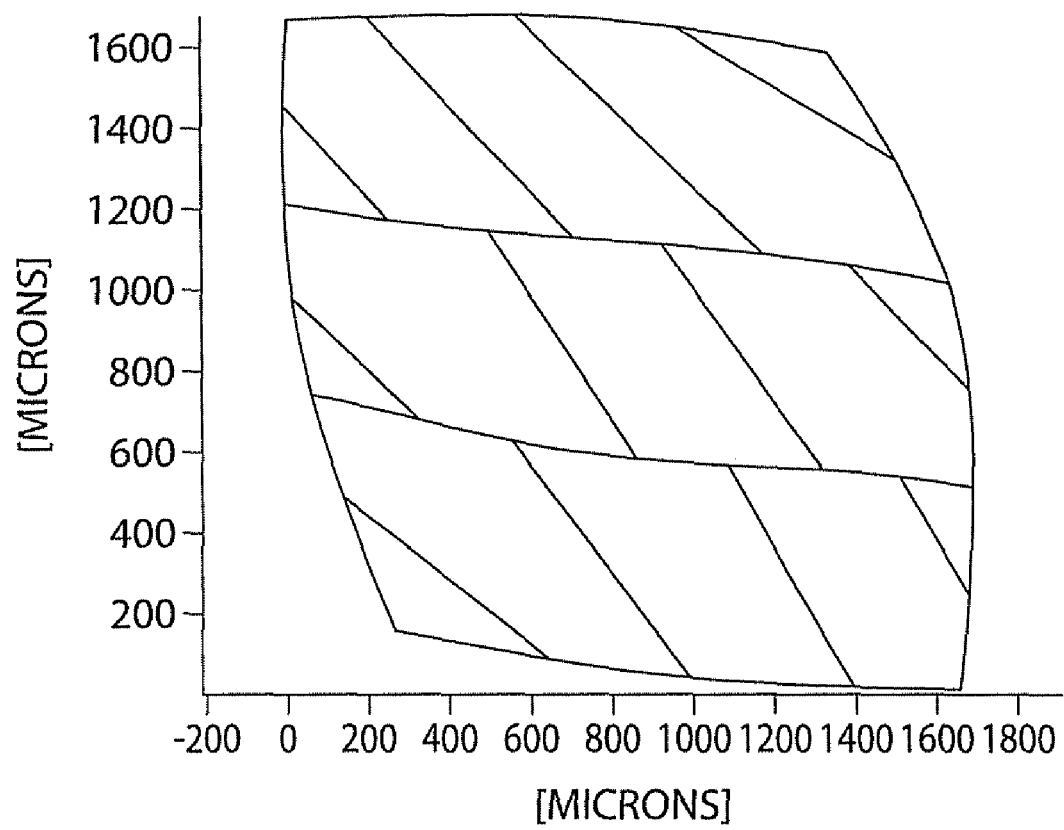
FIG. 31 is a diagram showing capillary bed topology for a network, Testnet-0, created using node-vessel data.

FIG. 31 is a diagram showing a network, Testnet-1, created by placing nodes on a grid and using an algorithm to connect selected nodes. The algorithm may count through all of the nodes on the grid and create vessels to connect each node to its nearest neighbors. Modifications may be made to the network by manually changing node locations and deleting some vessels.

A network may be created using a different method. A graphical user interface, for example, the Matlab® interface, may be used to create a drawing program. Lines drawn by a user are recorded in node-vessel format. Each time a new line is drawn the distances between its endpoints and all other existing endpoints are measured. If the distance between any two points is short enough, they can be considered to be the same point.

Figure 32:
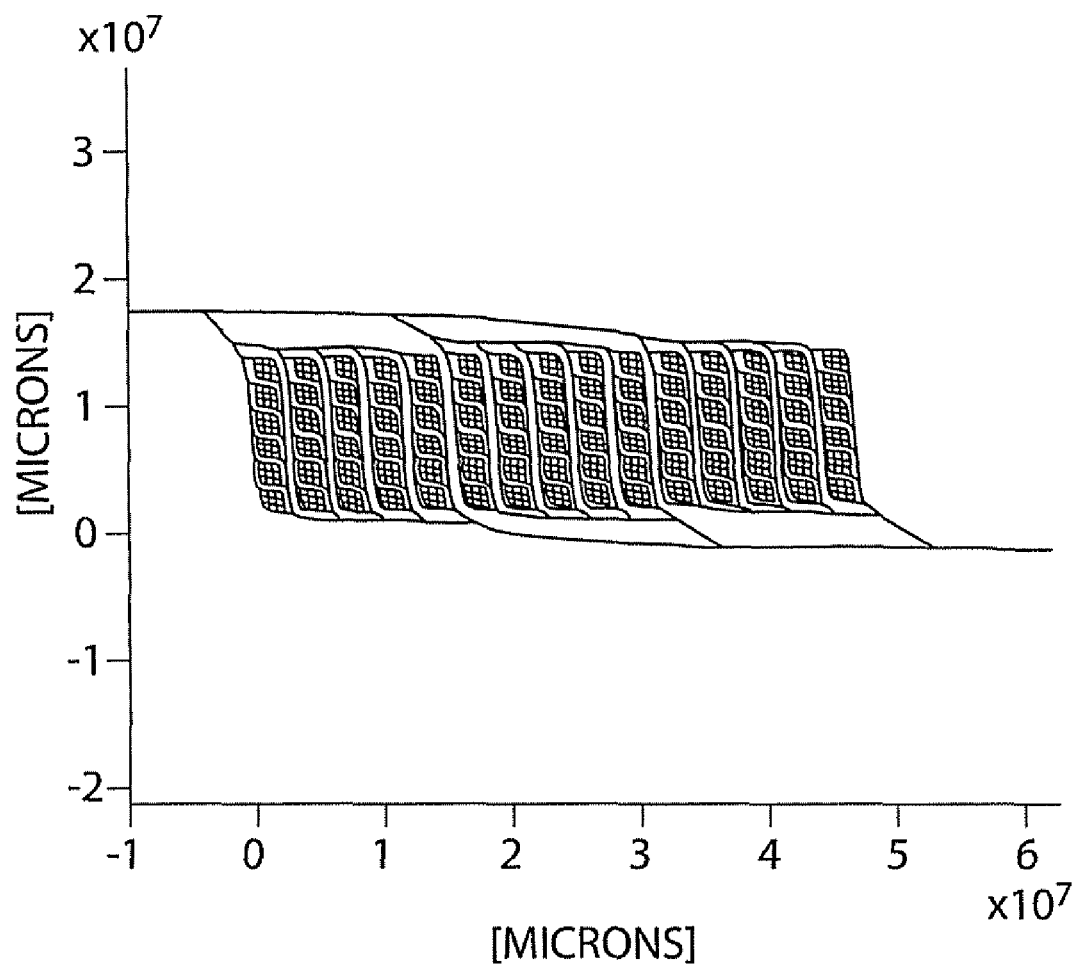
FIG. 32 is a diagram illustrating the topology of a network, referred to as Testnet-1.
Figure 33A:
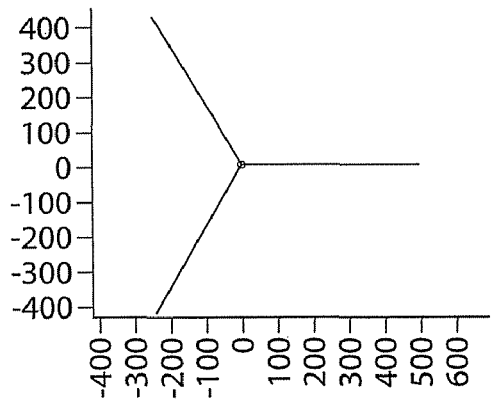
In FIG. 33A, the pattern begins by branching in three directions from a single node.
Figure 33B:
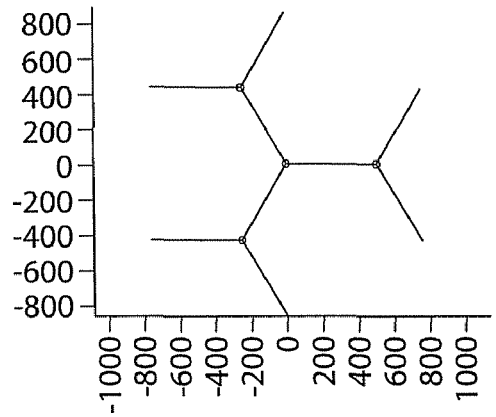
In FIG. 33B, the same branching pattern is applied to nodes other than the starting node.
Figure 33C:
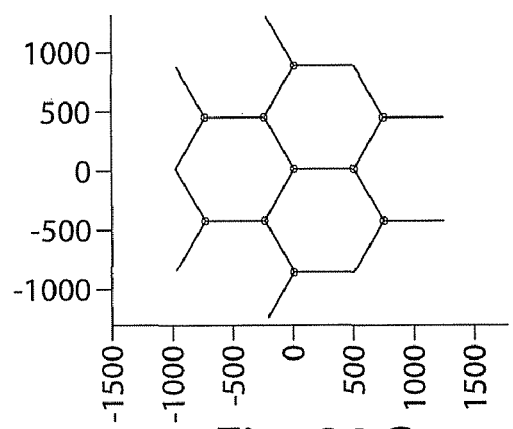
FIG. 33C shows the hexagonal pattern created by the fractal.
Figure 33D:
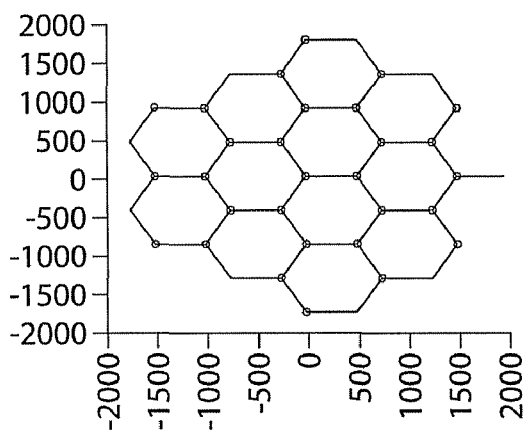
FIG. 33D shows that the pattern can be allowed to grow to any size.

FIG. 32 is a diagram illustrating a network, Testnet-1, using this method.

This network was created to match the branching pattern of a physiological capillary bed. The network was then multiplied over a larger area and more connections were drawn in, creating the full topology of the design shown in FIG. 32.

The topography of a three-dimensional stacked design may be based on a fractal algorithm. This algorithm was chosen because it can be used to create patterns of any size with the vessels spaced evenly throughout, and avoids sharp angles between intersecting vessels. The algorithm may include steps as follows:
1. Define a reference direction in the plane.
2. Define a vessel length L.
3. Define an origin.
4. Define a maximum pattern diameter.
5. Create three vessels with one node at the origin, each length L: one extending parallel to the reference direction, one at 120° from the reference direction, and one 240° from the reference direction.
6. Iterate through all of the newly created nodes. At each node, redefine the reference direction as the direction of a vessel connected to that node, redefine the origin as the current node, and perform step 5.
7. Repeat steps 5 and 6 until no new nodes can be added within the maximum pattern diameter.

Figure 40:
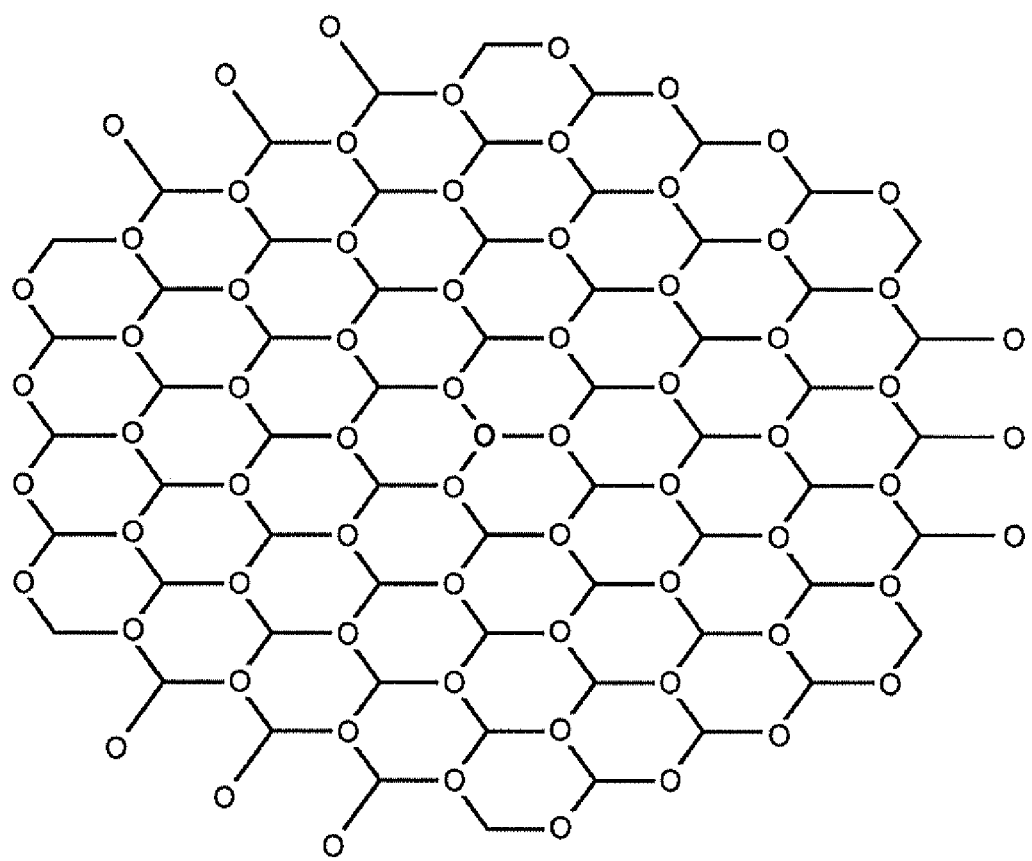
FIG. 40 shows a two-dimensional pattern produced by a fractal algorithm in accordance with an embodiment of the invention.
Figure 41:
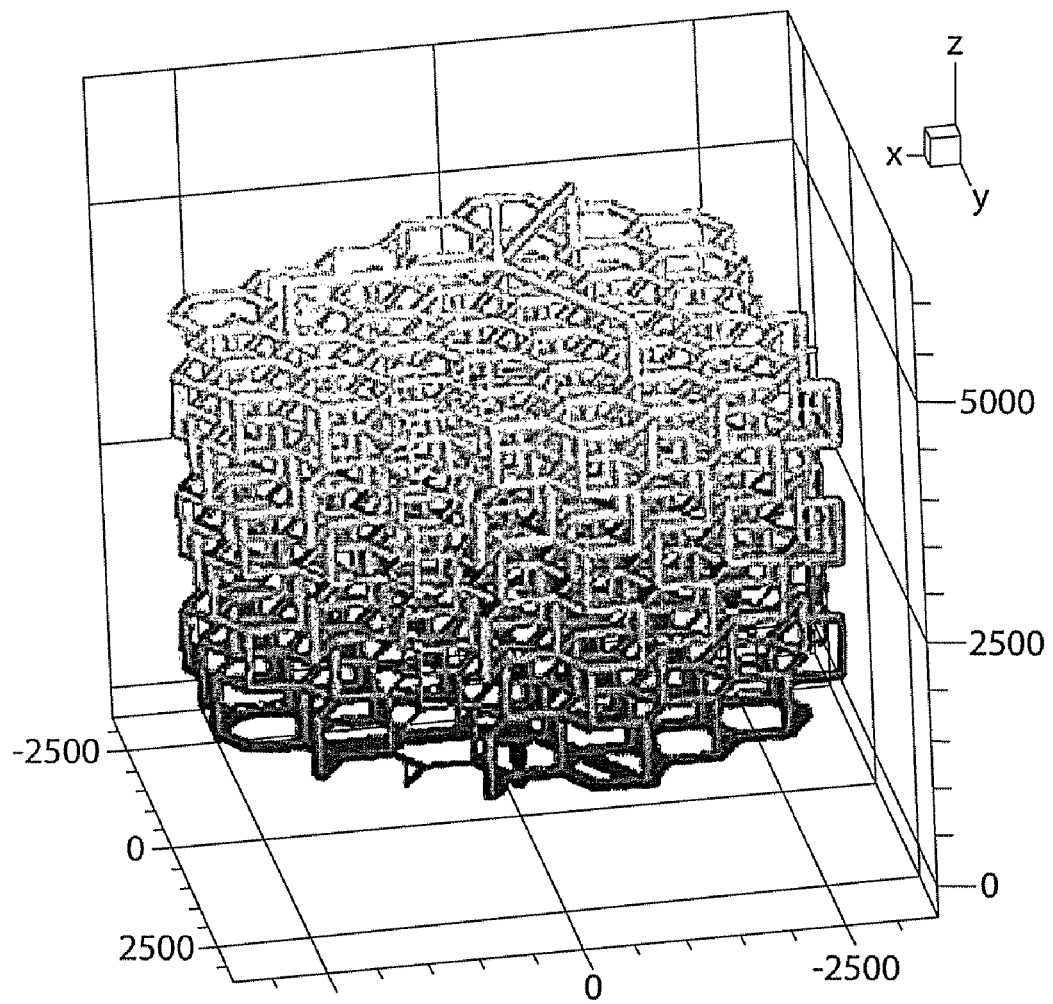
FIG. 41 shows a sample initial network in accordance with an embodiment of the invention.

A two-dimensional pattern produced by this algorithm is shown in FIG. 40. A three-dimensional network may be generated by stacking a set of two-dimensional layers. Layers in the middle of the pattern may be identical, while layers on the outside may be less dense to act as distribution layers. The software may search through all nodes in the network, connecting each pair of nodes that are found on adjacent layers and are aligned vertically. Inlet and outlet vessels may be added to either end, completing the initial network. A sample initial network is shown in FIG. 41.

Figure 34A:
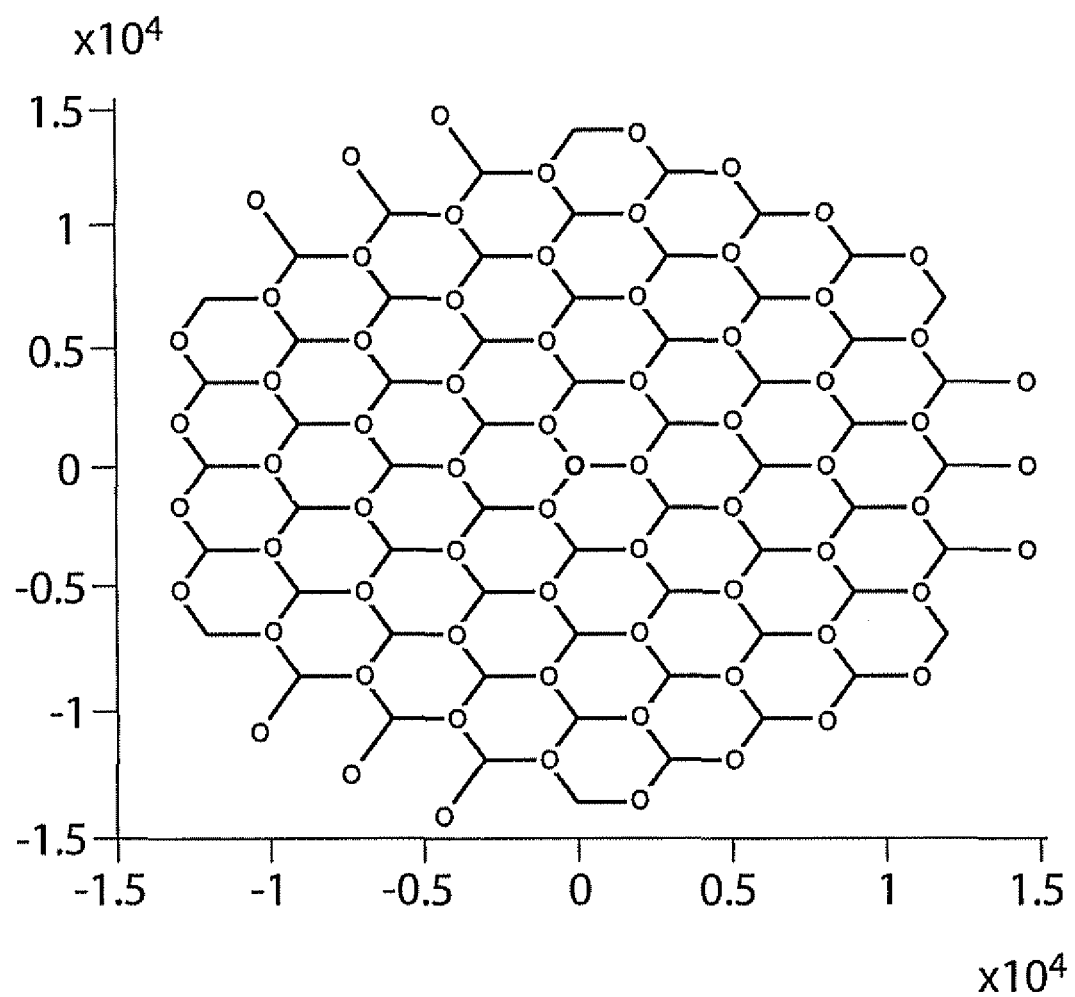
FIG. 34A shows layer B.
Figure 34B:
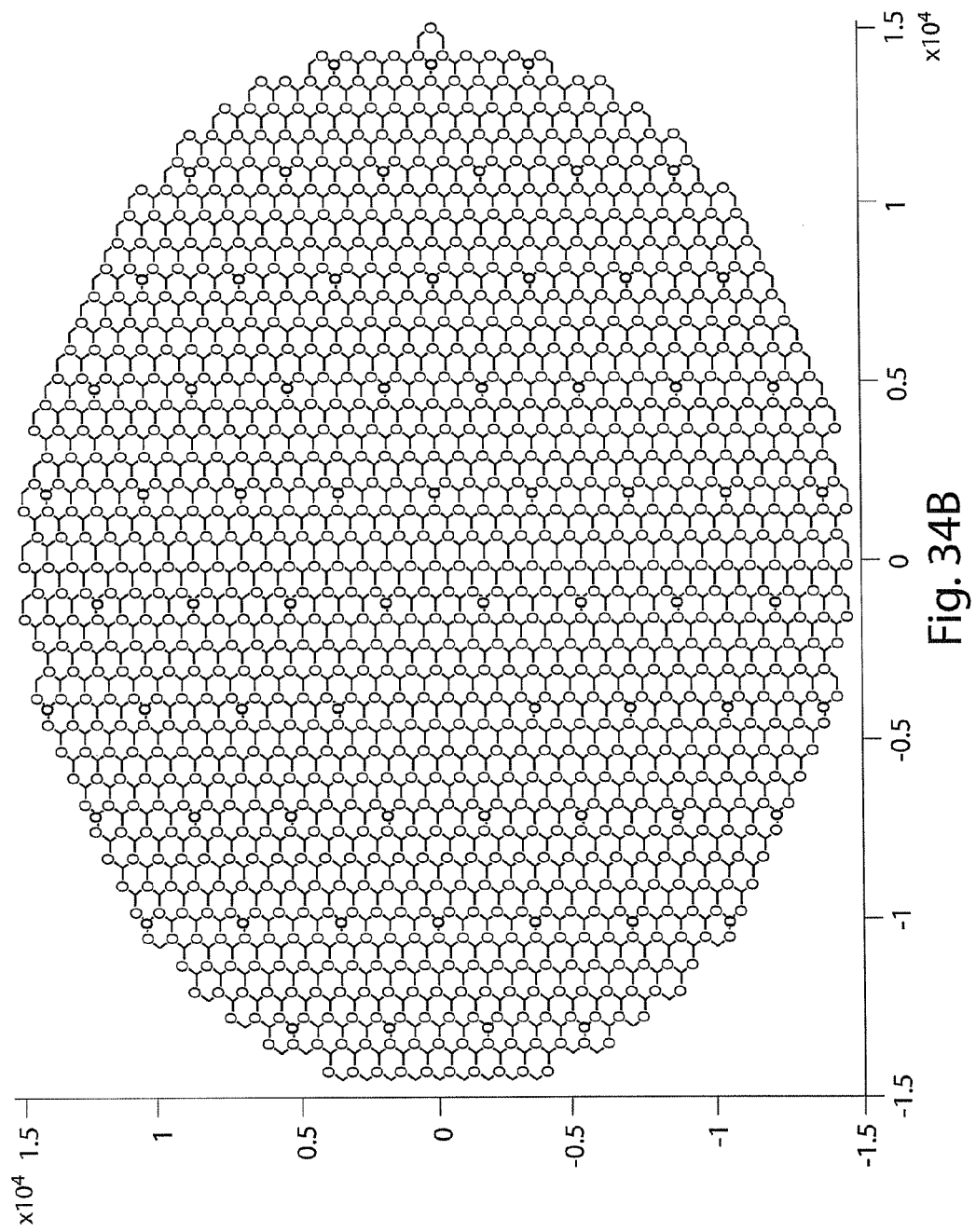
FIG. 34B shows layer D.
Figure 35A:
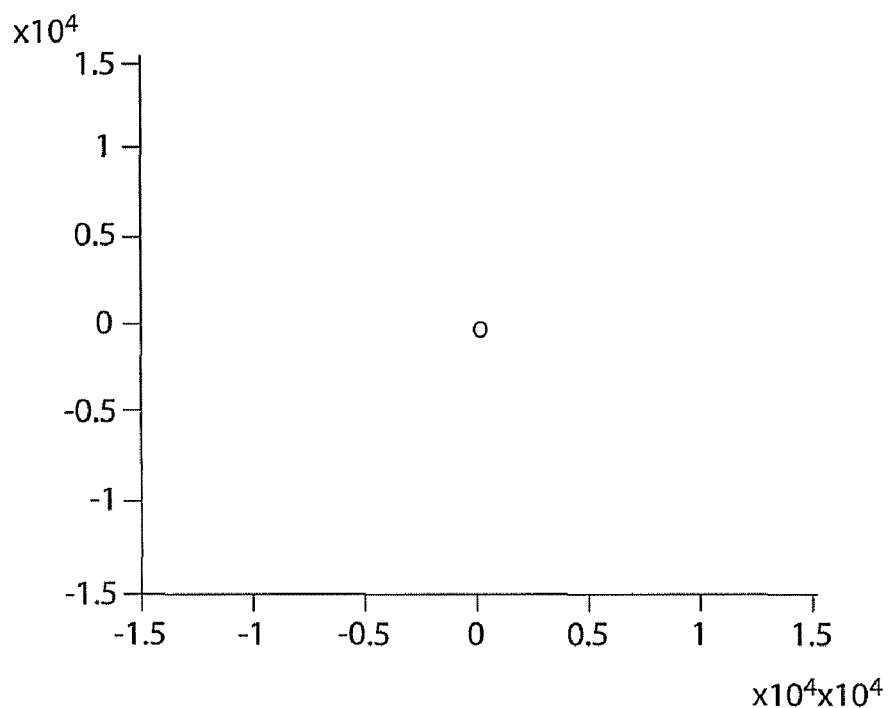
FIG. 35A shows layer A.
Figure 35B:
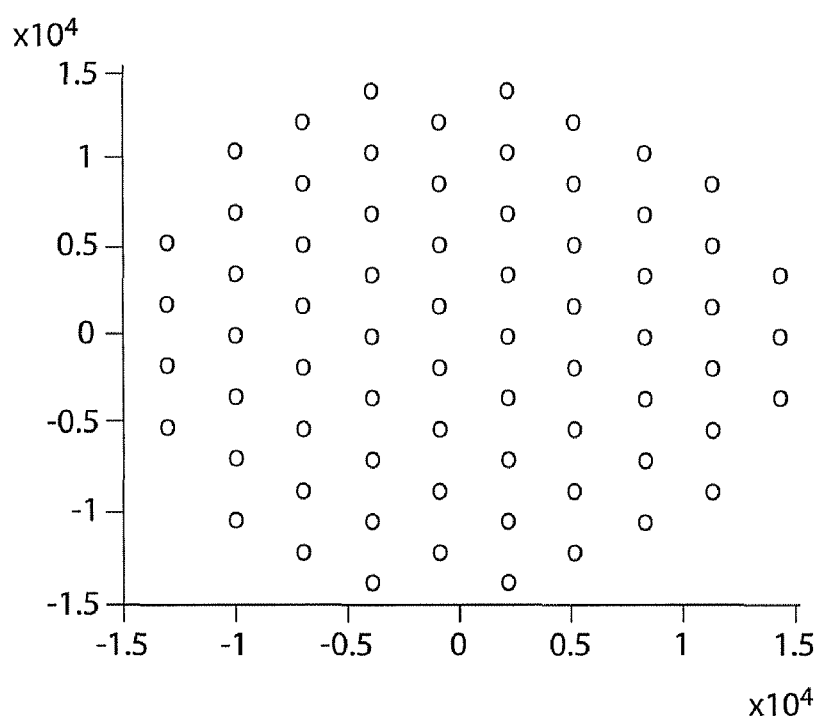
FIG. 35B shows layer C.
Figure 35C:
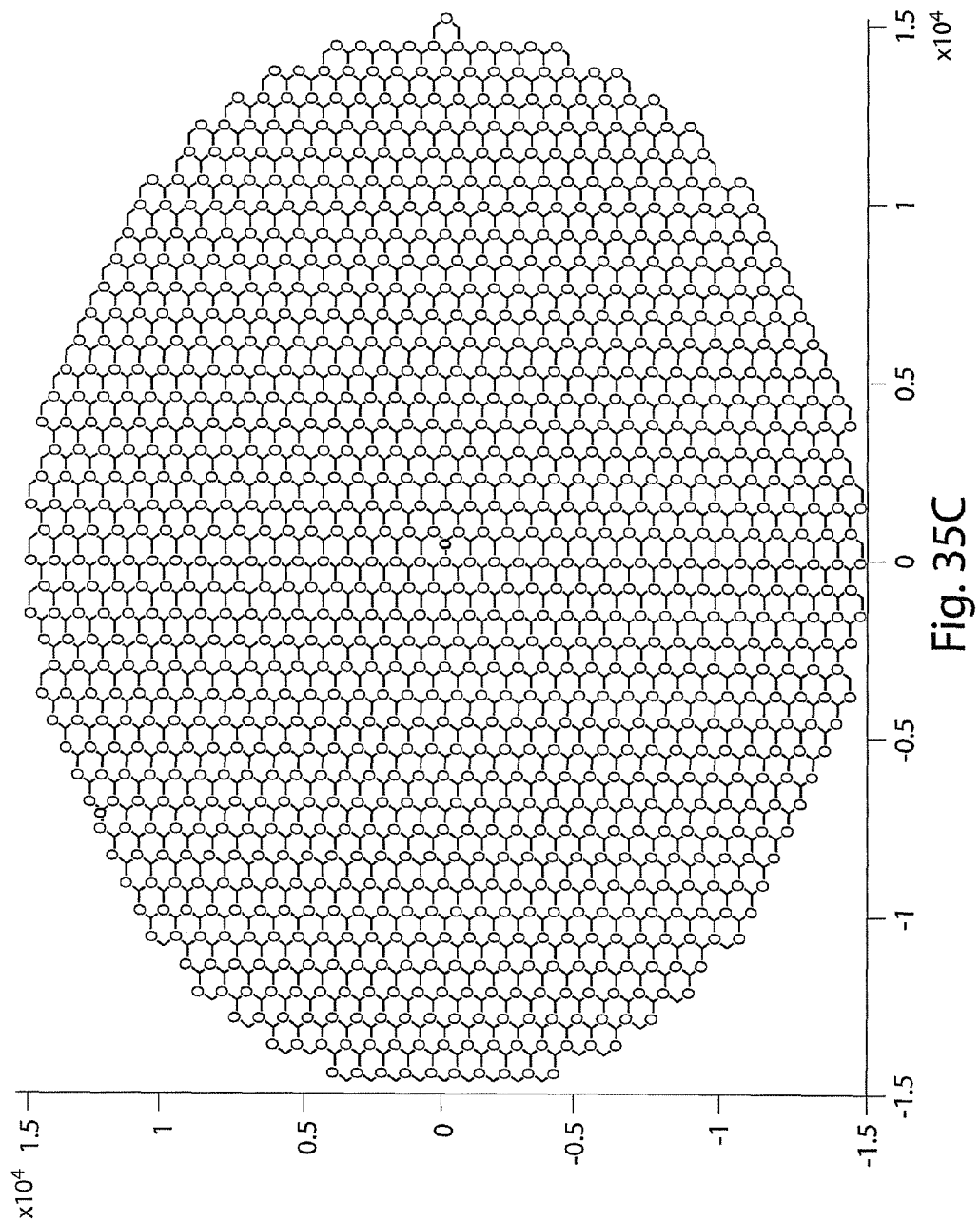
FIG. 35C shows layer E.
Figure 35D:
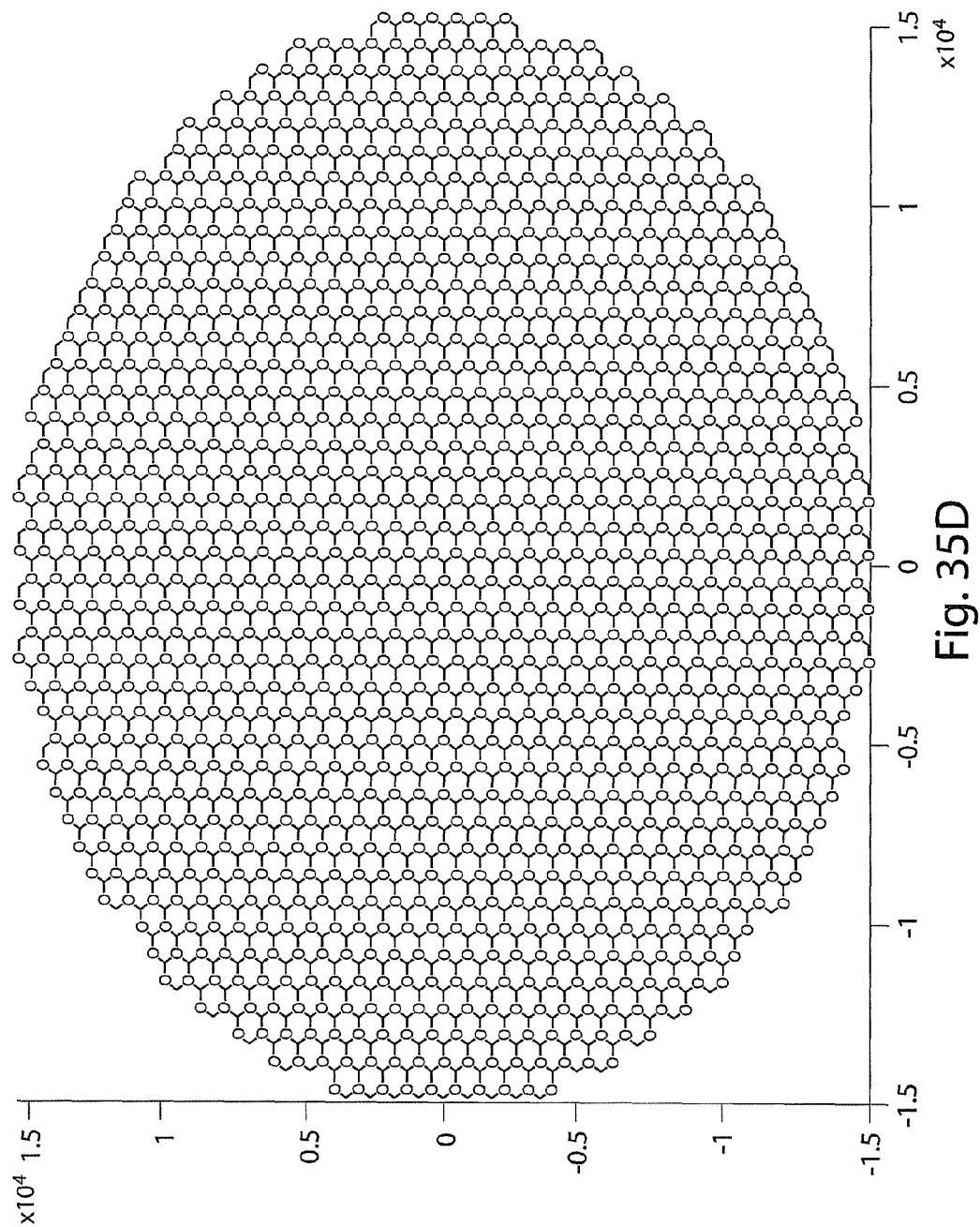
FIG. 35D shows layer F.

FIG. 34 illustrates a three-dimensional design, referred to here as "Hextak." As shown in FIG. 34, a series of vessel layers may be laid out on different wafers. The vessels in various layers may be interconnected by a pattern of vertical vessels. These vertical vessels are added to the design by placing them at regular distances throughout the patterns and are also shown in FIG. 34. The Hextak design may include four separate layers of vertical vessels, as shown in FIG. 34. A method for this Hextak design will be described in further detail below. The above-described methods create a network topology and describe it in node-vessel format. The node-vessel format may then be used to model the fluidic behavior in the network.

Predicting Flow Through a Single Microfabricated Vessel

The flow behavior and geometry of a cylindrical blood vessel can be related by a single equation, $$\mu \frac{Q}{\Delta P} = \frac{\pi D^4}{128 L}, \quad (3)$$

where Q is the flow rate through the vessel, µ is the viscosity of the fluid flowing through the vessel, $\Delta P$ is the pressure drop in the vessel, D is the diameter of the vessel, and L is the length of the vessel. The terms on the left-hand side of Equation (3) are representative of the flow behavior while the terms on the right-hand side are representative of the geometry of the vessel. Thus, if the geometry of a vessel is known, the flow behavior can be calculated and if the flow behavior is known, the geometry can be calculated.

The vessel can be described as a fluidic resistor, analogous to an electrical resistor. In this case the relation between flow rate and pressure drop may be given by $$\frac{\Delta P}{Q} = R, \quad (4)$$

where R is the fluidic resistance of the vessel, which is dependent only on the geometry of the vessel and the viscosity of the fluid. Equations 3 and 4 can be rearranged to find the resistance of a cylindrical vessel $$R_i = \frac{8 \mu L}{\pi D^4} \quad (5)$$

Similar equations for various non-cylindrical vessels, including etched vessels, may also be used. The flow in a lithography-etched vessel may be accurately predicted by the relation for flow in a rectangular vessel $$\Delta P = \frac{\mu L (x+y)^2}{8(xy)^3} \left(96 - 95\left(\frac{x}{y}\right) + 56\left(\frac{x}{y}\right)^2\right) Q, \quad (6)$$

where $\Delta P$ is the pressure drop from one end of the vessel to the other end, µ is the viscosity of the fluid flowing through the vessel, L is the length of the vessel, x is the width of the vessel, y is the depth of the vessel, and Q is the flow rate through the vessel.

Combining Equations (4) and (6) gives the expression for the fluidic resistance of a vessel:

$$R = \frac{8(xy)^3}{\mu L (x+y)^2} \left(96 - 95\left(\frac{x}{y}\right) + 56\left(\frac{x}{y}\right)^2\right)^{-1} \quad (7)$$

Predicting Flow Through a Network of Vessels

As a single vessel can be modeled by a fluidic resistor, a network of vessels can be modeled by a network of resistors (i.e. an electric circuit). Thus, methods for analyzing electrical resistor networks may be used for analyzing analogous fluidic networks.

The node-vessel topology can be translated into a set of equations describing the flow behavior in the network. The first network calculation is to find the flow rates throughout the network. Since it is desirable to have the flow throughout a network be evenly distributed, vessels may be designated as capillaries in size and a flow rate for each may be assigned accordingly. The flow rates may be stored in a list where each vessel has a corresponding flow rate. The equation for continuity in fluidic networks, or the analogous Kirchoff Current Law in electrical circuits, tells that the sum of all flow rates at any node in the network is zero. As long as enough capillaries are defined, this law may be used to find the flow rates throughout the network. The software goes through the list of nodes calculating flow rates at every node that it can. For example, if a node has three vessels connected to it and two of those vessels have known flow rates, the flow rate in the third vessel can be found. Thus, the flow rates of all of the vessels in the network may be determined.

Once all the flow rates are known, a system of equations describing the flow behavior in the network can be created. The network where the pressures and resistances throughout the network are unknown may be described by a set of simultaneous linear equations. In matrix form, $$\begin{bmatrix} [N] & [Q] \\ & [K] \end{bmatrix} \begin{bmatrix} \overline{P} \\ \overline{R} \end{bmatrix} = \begin{bmatrix} \overline{0} \\ \overline{k} \end{bmatrix}, \quad (8)$$

where [N] is a matrix that picks values out of the pressure vector to go in the element equations, [Q] is a diagonal vector with entries corresponding to the flowrate in each vessel, $\overline{P}$ is the vector of unknown pressures, $\overline{R}$ is the vector of unknown resistances, [K] is a matrix of values representing the constraint equations, $\overline{0}$ is a vector of zeros, and $\overline{k}$ is a vector of known values.

The upper section of Equation (8), $$[N][Q]\begin{bmatrix} \overline{P} \\ \overline{R} \end{bmatrix} = [\overline{0}], \quad (9)$$

represents a set of Equation (4)'s, one for each vessel. This set of equations is set up by counting through the list of vessels, representing the two nodes at the end of each vessel in [N], and representing the flow rate in each vessel in [Q].

The bottom section of Equation (8), $$[K]\left[\frac{\overline{P}}{\overline{R}}\right] = [\overline{k}], \quad (10)$$

represents the constraint equations. The system cannot be solved unless the number of rows in the matrix on the left-hand side of Equation (8) is equal to the number of pressures plus the number of resistances, i.e. there are n equations and n unknowns. Equation (9) supplies a number of rows equal to the number of resistances, so Equation (10) may be used to supply a number of rows equal to the number of pressures, also equal to the number of nodes in the system. The constraint equations can set pressures or resistances to constant values, or set relationships between resistances or relationships between pressures, or any combination. The pressure at the inlet and outlet of the network may always be set to constant values in accordance with physiological requirements. Other relations may be to set pressure fronts where groups of nodes have the same pressure, or to set resistance groups, such as forcing all capillaries to have the same resistance. Some sets of constraints do not yield a solution, but others are guaranteed to always have a solution as long as reasonable numerical values are placed on the constraints. One of these sets is to constrain all of the pressures in the network and solve only for resistance.

Equation (7) is asymmetric and must be solved using Sparse Gaussian Elimination. The result is a list of the pressures and resistances throughout the network. When the resistances are known and an etch depth for each layer is specified, Equation (7) can be used to find the width of each vessel. Equation (7) cannot be solved explicitly for the width given the value of R, so a Newton Method may be used to solve Equation (7) for the width. Once the width of each vessel is known, the design is complete; the orientation and shape of all vessels in the network is known.

Figure 36A:
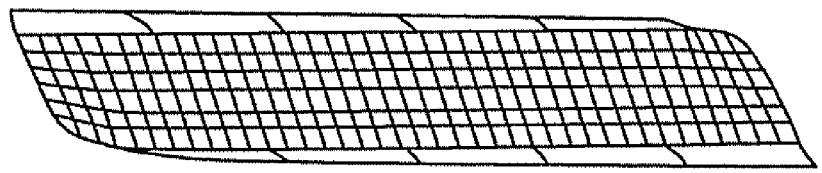
FIG. 36 is a diagram showing the schematics of the completed two-dimensional network designs for Testnet-0 (FIG. 36A) and Testnet-1 (FIG. 36B).
Figure 36B:
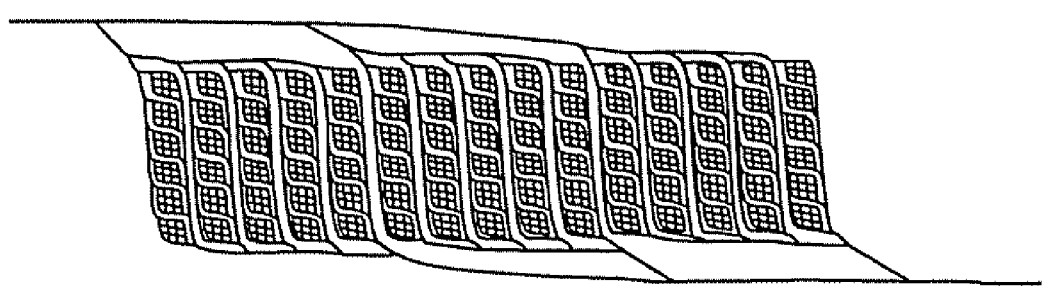
Figure 37:
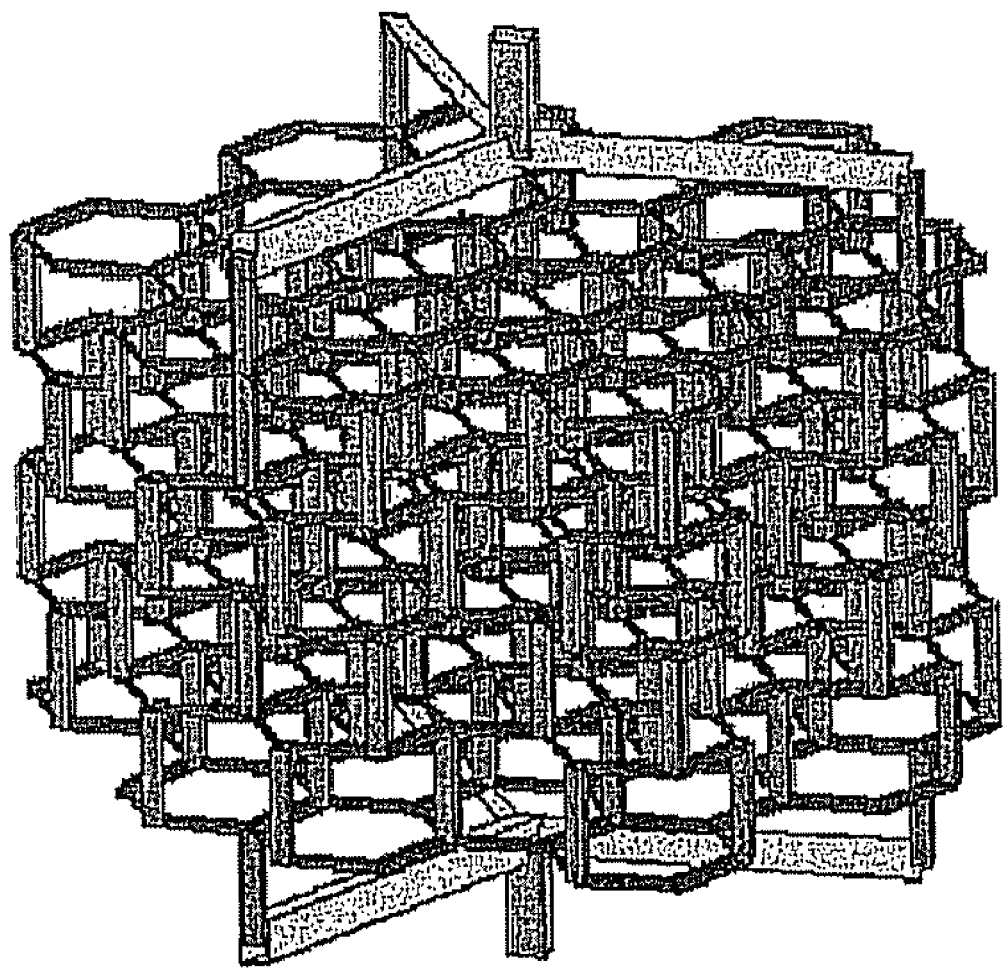
FIG. 37 is a diagram of a section of Hextak where each vessel is plotted as an individual three-dimensional element.

Schematics of the completed designs for Testnet-0 and Testnet-1 are shown in FIG. 36. FIG. 37 is a diagram of a section of Hextak where each vessel is plotted as an individual three-dimensional element.

Experimental Verification of Fluidic Model

Figure 38A:
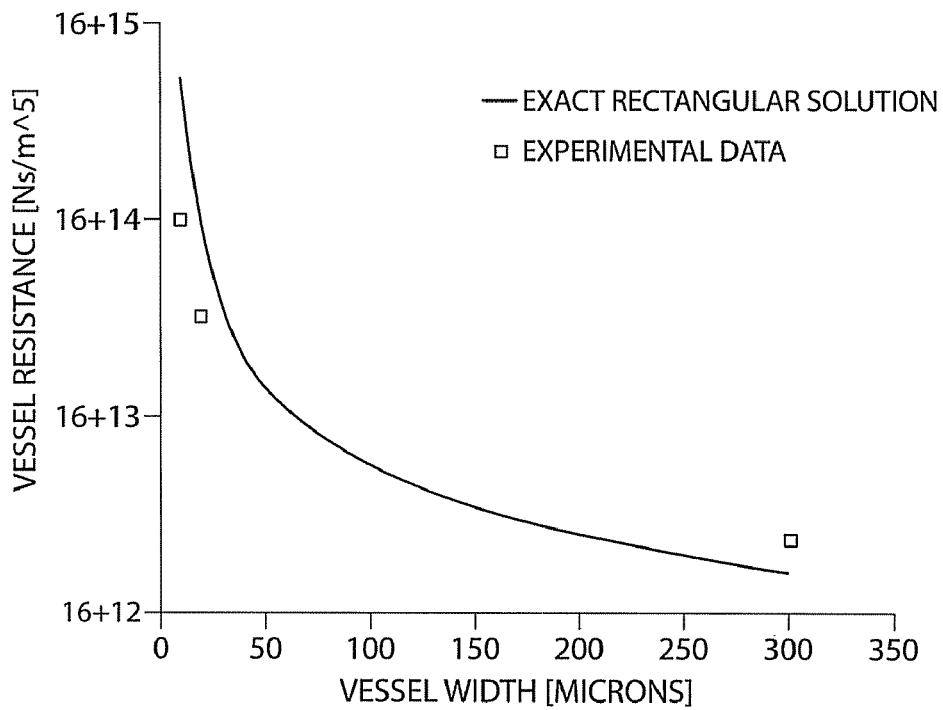
FIG. 38 shows fluidic resistance of vessels with varying widths (FIG. 38A) and varying lengths (FIG. 38B).
Figure 38B:
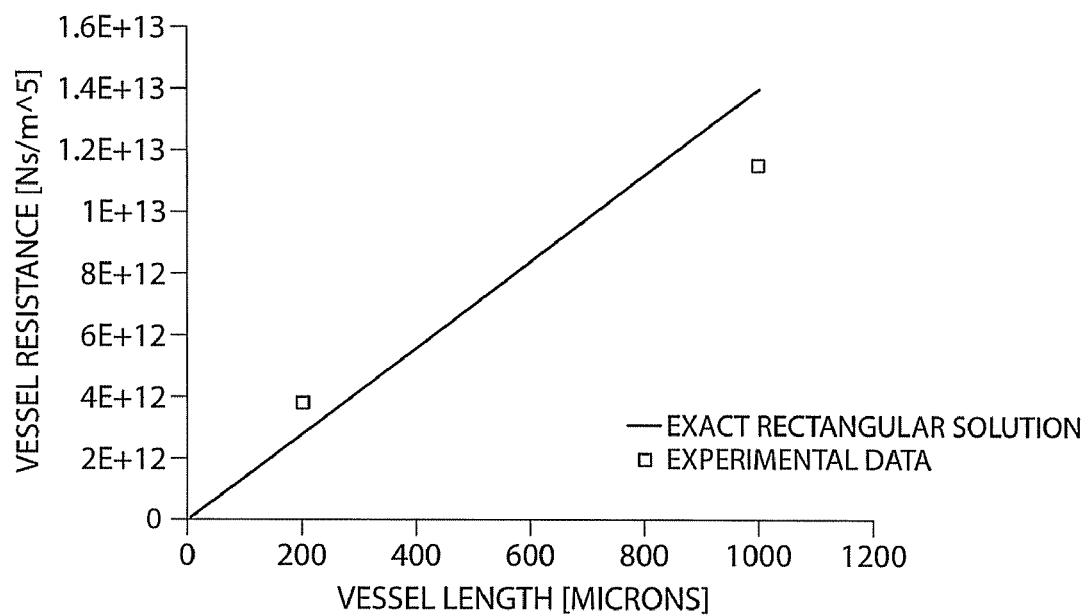

The model of flow in a single vessel and predictions of flows in small patterns have been shown to be accurate by measuring the flow rates through individual vessels and small patterns. An example from this work is presented in FIG. 38, showing the ability to predict the fluidic resistance of vessels with varying widths or varying lengths. The model was also shown to be accurate in small patterns in predicting flows at varying pressures and flow rates through vessels of varying depths and topology.

Figure 39:
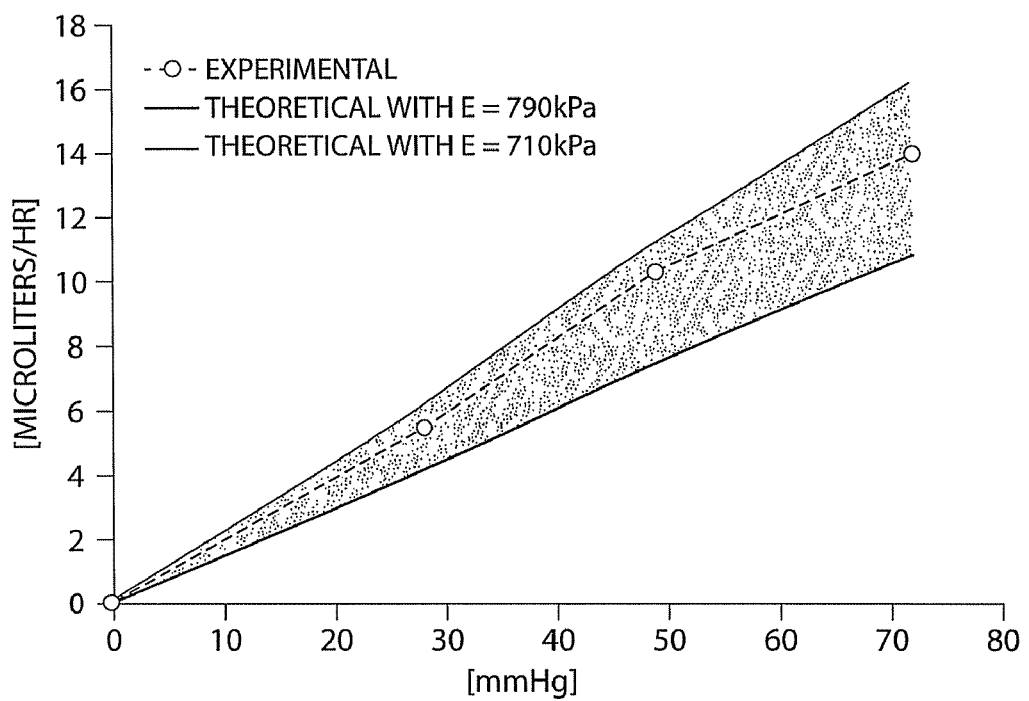
FIG. 39 is a diagram showing a comparison of the prediction made by the network modeling software to experimental data for the total flow rate through the vessel versus the pressure drop across the device for a Testnet-1.

The theoretical model has been shown to accurately predict gross behavior of full networks. As shown in FIG. 39, the model predictions match the experimental behavior within an acceptable error for variation in the elasticity of the material used to construct the network.

Implementation of Design Method

The design method may be implemented in any programming language, such as the C programming language and so forth. Programming code may be compiled using the GNU compiler collection. As described before, system 100 may include any general purpose computing device. For example, compiling and computation may be performed on an SGI Origin 2000 workstation. Graphics may be plotted using Matlab, Tecplot, or the like.

The design method may include steps as follows:
1. Generate a network topology in Node-Vessel format using a fractal method.
2. Generate the system of flow equations (Equation 9).
3. Set the system of constraint equations (Equation 10).
4. Solve all of the equations (Equation 8) simultaneously to determine the vessel resistances.
5. Use the resistance-geometry relation (Equation 4) to determine the geometry of each vessel.

Figure 42:
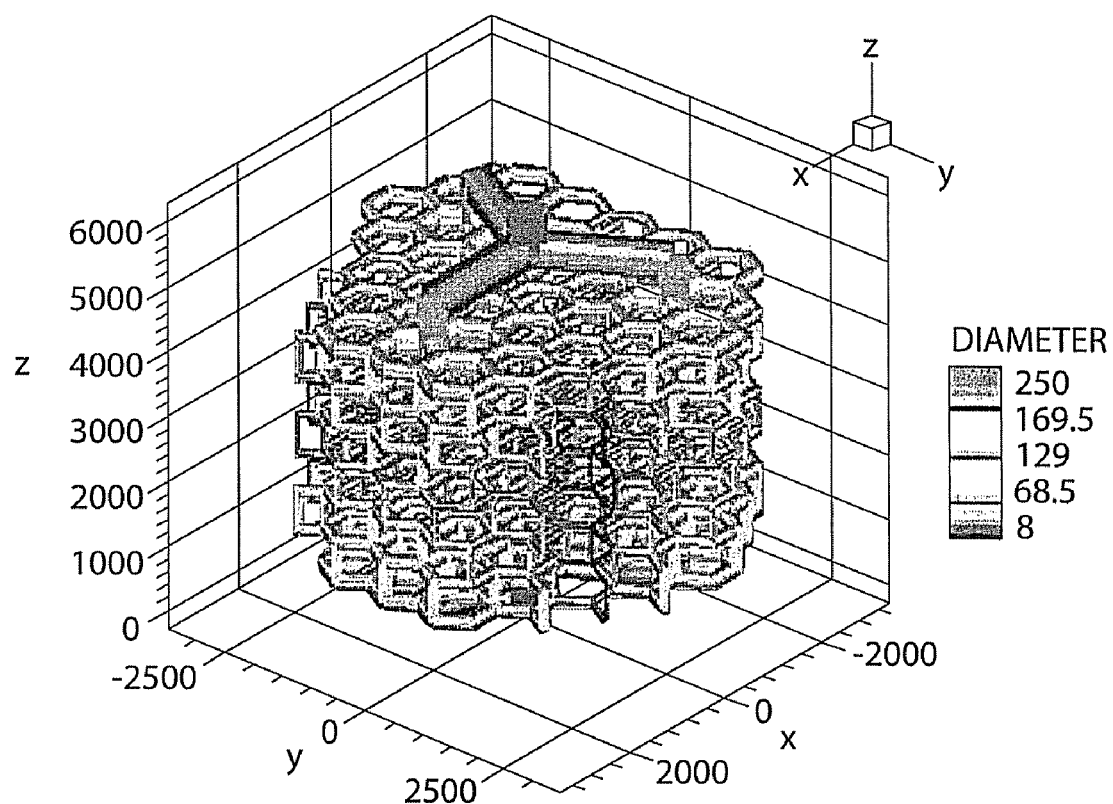
FIG. 42 depicts a full version of the design as shown in FIG. 28.

A full network appropriate for use as support for a tissue engineered organ is shown in FIG. 42.

Comparison of Network Designs to Physiological Systems

Once a network design has been completed, the Strahler ordering system can be applied to compare the network to physiological data. For the diameter-defined Strahler system, the diameter distribution of a designed network may match that of measured physiological systems.

Flow properties may be used as inputs to the design so that the flow properties throughout the network also match physiological values. The number of vessels of each order may be compared. Mass transport occurs in the smallest vessels, so a network must have the appropriate number of small vessels to viably support an organ. A highly interconnected stacked device such as the Hextak provides the necessary number of vessels.

Micromachining and Chemical Processing of Silicon and Other Mold Materials

Molds can be made by creating small mechanical structures in silicon, metal, polymer, and other materials using microfabrication processes. These microfabrication processes are based on well-established methods used to make integrated circuits and other microelectronic devices, augmented by additional methods developed by workers in the field of micromachining.

Microfabrication processes that can be used in making the molds disclosed herein include lithography; etching techniques, such as lasers, plasma etching, photolithography, or chemical etching such as wet chemical, dry, and photoresist removal; or by solid free form techniques, including three-dimensional printing (3DP), stereolithography (SLA), selective laser sintering (SLS), ballistic particle manufacturing (BPM) and fusion deposition modeling (FDM); by micromachining; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination or by combinations thereof. See Jaeger, *Introduction to Microelectronic Fabrication* (Addison-Wesley Publishing Co., Reading Mass. 1988); Runyan, et al., Semiconductor Integrated Circuit Processing Technology (Addison-Wesley Publishing Co., Reading Mass. 1990); *Proceedings of the IEEE Micro Electro Mechanical Systems Conference* 1987-1998; Rai-Choudhury, ed., *Handbook of Microlithography, Micromachining & Microfabrication* (SPIE Optical Engineering Press, Bellingham, Wash. 1997). The selection of the material that is used as the mold determines how the surface is configured to form the branching structure. The following methods are preferred for making molds.

Typically, micromachining is performed on standard bulk single crystal silicon wafers of a diameter ranging between about 50 and 300 millimeters (mm), preferably approximately 100 mm, and of thickness ranging between about 200 and 1200 µm. These wafers can be obtained from a large number of vendors of standard semiconductor material, and are sawn and polished to provide precise dimensions, uniform crystallographic orientation, and highly polished, optically flat surfaces. Wafers made from pyrex borosilicate or other glasses can also be procured and inserted into micromachining processes, with alternative processes used to etch the glassy materials.

The geometry of the mold, in particular the number of different feature depths required, is the major factor determining the specific process sequence. The simplest case is that of a single depth dimension for the mold. Specifically, for a silicon substrate, the process sequence is as follows: first, the silicon wafer is cleaned, and a layer of photosensitive material is applied to the surface. Typically, the layer is spun on at a high revolution rate to obtain a coating of uniform thickness. The photoresist is baked, and the wafer is then exposed to ultraviolet or other short-wavelength light though a semi-transparent mask. This step can be accomplished using any one of several masking techniques, depending on the desired image resolution. The resist is then developed in an appropriate developer chemistry, and the wafer is then hard-baked to remove excess solvent from the resist. Once the lithographic process has been completed, the wafer can be etched in a plasma reactor using one of several possible chemistries. Etching serves to transfer the two-dimensional pattern into the third dimension: a specified depth into the wafer. Plasma parameters are determined by the desired shape of the resulting trench (semi-circular, straight-walled profile, angled sidewall), as well as by the selectivity of the etchant for silicon over the masking photoresist. Once the etching has been completed, the photoresist can be removed and the wafer prepared for use in the tissue molding process.

Increased flexibility in the geometry of wafer mold can be obtained by inserting additional cycles of masking and etching, as shown in FIG. 1. Here, a second step in which a masking layer has been applied, and open areas etched, is shown. This modification provides the opportunity to machine channels of varying depths into the wafer mold. To design a mold that is suitable for the culturing of endothelial cells, increased flexibility is very important due to the need for vascular branches with different diameters. The techniques can be extended to provide as many additional layers and different depths as are desired. In addition, these techniques can be used to create secondary patterns within the pattern of microchannels. For example, it may be advantageous to have wells within the microchannels for culturing additional cell types such as feeder cells. The pattern of microchannels also can be designed to control cell growth, for example, to selectively control the differentiation of cells.

Glass and polymeric wafer molds can be fabricated using a similar sequence, but the actual process can be modified by the addition of an intervening masking layer, since etchants for these materials may attack photoresist as well. Such intervening materials simply function to transfer the pattern from the photoresist to interlayer and then on to the wafer below. For silicon etched in one of several wet chemistries, an intervening layer may also be necessary.

The size distribution of the etched porous structure is highly dependent on several variables, including doping kind and illumination conditions, as detailed in Lehmann, "Porous Silicon—A New Material for MEMS", *IEEE Proceedings of the Micro Electro Mechanical Systems Conference*, pp. 1-6 (1996). Porous polymer molds can be formed, for example, by micromolding a polymer containing a volatilizable or leachable material, such as a volatile salt, dispersed in the polymer, and then volatilizing or leaching the dispersed material, leaving a porous polymer matrix in the shape of the mold. Hollow molds can be fabricated, for example, using combinations of dry etching processes (Laermer, et al., "Bosch Deep Silicon Etching: Improving Uniformity and Etch Rate for Advanced MEMS Applications," *Micro Electro Mechanical Systems*, Orlando, Fla., USA, (Jan. 17-21, 1999); Despont, et al., "High-Aspect-Ratio, Ultrathick, Negative-Tone Near-UV Photoresist for MEMS", *Proc. of IEEE 10$^{th}$ Annual International Workshop on MEMS*, Nagoya, Japan, pp. 518-522 (Jan. 26-30, 1997)); micromold creation in lithographically-defined polymers and selective sidewall electroplating; or direct micromolding techniques using epoxy mold transfers.

Polymeric molds can also be made using microfabrication. For example, the epoxy molds can be made as described above, and injection molding techniques can be applied to form the structures. These micromolding techniques are relatively less expensive to replicate than the other methods described herein.

Three-dimensional printing (3DP) is described by Sachs, et al., *Manufacturing Review* 5, 117-126 (1992) and U.S. Pat. No. 5,204,055 to Sachs, et al. 3DP is used to create a solid object by ink-jet printing a binder into selected areas of sequentially deposited layers of powder. Each layer is created by spreading a thin layer of powder over the surface of a powder bed. The powder bed is supported by a piston, which descends upon powder spreading and printing of each layer (or, conversely, the ink jets and spreader are raised after printing of each layer and the bed remains stationary). Instructions for each layer are derived directly from a computer-aided design (CAD) representation of the component. The area to be printed is obtained by computing the area of intersection between the desired plane and the CAD representation of the object. The individual sliced segments or layers are joined to form the three-dimensional structure. The unbound powder supports temporarily unconnected portions of the component as the structure is built but is removed after completion of printing.

SFF methods other than 3DP that can be utilized to some degree as described herein are stereo-lithography (SLA), selective laser sintering (SLS), ballistic particle manufacturing (BPM), and fusion deposition modeling (FDM). SLA is based on the use of a focused ultra-violet (UV) laser that is vector scanned over the top of a bath of a photopolymerizable liquid polymer material. The UV laser causes the bath to polymerize where the laser beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired apparatus is obtained. The most recently created layer in each case is always lowered to a position for the creation of the next layer slightly below the surface of the liquid bath. A system for stereolithography is made and sold by 3D Systems, Inc., of Valencia, Calif., which is readily adaptable for use with biocompatible polymeric materials. SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer. A suitable system adaptable for use in making medical devices is available from DTM Corporation of Austin, Tex.

BPM uses an ink-jet printing apparatus wherein an ink-jet stream of liquid polymer or polymer composite material is used to create three-dimensional objects under computer control, similar to the way an ink jet printer produces two-dimensional graphic printing. The mold is formed by printing successive cross-sections, one layer after another, to a target using a cold welding or rapid solidification technique, which causes bonding between the particles and the successive layers. This approach as applied to metal or metal composites has been proposed by Automated Dynamic Corporation of Troy, N.Y. FDM employs an x-y plotter with a z motion to position an extrudable filament formed of a polymeric material, rendered fluid by heat or the presence of a solvent. A suitable system is available from Stratasys, Incorporated of Minneapolis, Minn.

The design of the channels in the mold can be constructed by a number of means, such as fractal mathematics, which can be converted by computers into two-dimensional arrays of branches and then etched onto wafers. Also, computers can model from live or preserved organ or tissue specimens three-dimensional vascular channels, convert to two-dimensional patterns and then help in the reconversion to a three-dimensional living vascularized structure. Techniques for producing the molds include techniques for fabrication of computer chips and microfabrication technologies. Other technologies include laser techniques.

Semi-Permeable Membrane

A semi-permeable membrane can be used to separate the first mold or polymer scaffold from the second mold or polymer scaffold in the microfabricated apparatuses of the invention. Preferably, the pore size of the membrane is smaller than the cell diameters, thus, cells will not be able to pass through (i.e. a low permeability for animal cells), while low molecular weight nutrients and fluids can pass through (i.e. a high permeability for nutrients), thereby providing adequate cell-to-cell signaling. Cell sizes vary but in general, they are in the range of microns. For example, a red blood cell has a diameter of 8 μm. Preferably, the average membrane pore size is on a submicron-scale to ensure effective screening of the cells.

In specific embodiments, the semi-permeable membrane will contain an endothelial layer, in order to inhibit passage of metabolites between layers. For example, a microfabricated apparatus could comprise bilayer units, each layer separated by an endothelized membrane, wherein an upper layer comprises vasculature and a lower layer comprises liver cells. Upon application to the vasculature, the test agent would circulate through flow connectors into the lower layer, where it is metabolized. Metabolites would then flow out of the system with the bile (e.g., through bile ducts).

The endothelial lining of the semi-permeable membrane can comprise extra cellular matrix components for support. Alternatively, a polymer layer that does not inhibit flow between layers, such as a polycarbonate or polyethersulfone layer, can be applied.

Semi-permeable membranes of the present invention comprise a wide array of different membrane types and morphologies, which can be classified as follows:
(1) Track-etch membranes consisting of cylindrical through-holes in a dense polymer matrix. These membranes are typically made by ion-etching; or
(2) Fibrous membranes made by various deposition techniques of polymeric fibers. While these membranes do not have a well-defined pore topology, production methods have been sufficiently refined so that fibrous membranes have specific molecular weight cut-offs.

Track-etch type membranes are preferred, as they limit the fluid motion in one direction. Preferably, fluid motion is in the vertical direction. Fibrous membranes permit fluid motion both laterally and vertically.

The development of an appropriate membrane will mirror the device progression. Biocompatible and non-degradable membranes can be incorporated in microchannels that are made from poly(dimethyl siloxane) (PDMS). Since PDMS is non-degradable, the membranes do not need to be degradable either. However, degradable membranes and materials for microchannels can also be used. There exists a variety of commercial track-etch membranes with well-defined pore sizes that can be used for this purpose. Care must be taken to properly incorporate the membranes into the existing microchannels without leaking. To this end, the membranes can be bonded with either an oxygen plasma or a silicone-based adhesive. A small recession can be designed into the microchannels so that the membrane can fit tightly therein.

In principle, membrane formation from polymers relies on phase-phase separation. Polymer-solvent interactions are complex, and polymer phase diagrams are significantly more complicated than those for monomeric materials, e.g., metals. Phase separation can be induced either by diffusion (diffusion-induced phase separation or "DIPS") or by thermal means (thermal induced phase separation or "TIPS").

A DIPS system comprises polymer, solvent and non-solvent. The polymer solution is cast as a thin film and then immersed in a coagulation bath containing the non-solvent. This process is governed by the diffusion of various low molecular weight components. The exchange of solvent and non-solvent between the polymer solution and the coagulation bath leads to a change in the composition in the film and phase separation is induced. After some time, the composition of the polymer-rich phase reaches the glass transition composition and the system solidifies. To avoid macrovoid formation, a small amount of non-solvent can be mixed with the polymer solution. In a preferred embodiment, the polymer is polycaprolactone (PCL) and the separation system is chloroform/methanol. Specifically, a polymer solution with a concentration ranging from about 5-10% wt. is made. PCL is prepared by dissolving it in chloroform at room temperature under gentle stirring. Once the polymer has completely dissolved, a small amount is placed on a clean mirror surface, and a membrane knife is used to spread out a film with preset thickness. The thickness of the film can be adjusted by changing the gap between the knife blade and the mirror surface. Once the film has been spread, the entire mirror is immersed in a methanol bath. Phase separation occurs almost instantaneously, but the film and mirror are left in the coagulation bath for up to about 10 minutes to lock in the morphology. A typical membrane thickness is about 100 μm, and the pore size is on the order of about 1 μm, preferably between about 0.01 and 20 μm. Membrane morphology can be varied by altering the composition/concentration of the polymer solution, the film thickness, the components of the coagulation bath, and/or the process conditions. One skilled in the art would understand how to vary any one of these parameters to achieve the desired result.

A TIPS system comprises a thermal gradient to induce phase separation. By choosing a polymer-solvent system that is miscible at high temperatures, but immiscible at low temperatures, e.g., room temperature, phase separation can be induced upon cooling down the polymer solution. In a preferred embodiment, the polymer is PCL and the separation system is DMF/10% $C_3H_8O_3$.

Cells to be Seeded onto the Mold or Polymer Scaffold

The tissue will typically include one or more types of functional, mesenchymal or parenchymal cells, such as smooth or skeletal muscle cells, myocytes (muscle stem cells), fibroblasts, chondrocytes, adipocytes, fibromyoblasts, ectodermal cells, including ductile and skin cells, hepatocytes, kidney cells, pancreatic islet cells, cells present in the intestine, and other parenchymal cells, osteoblasts and other cells forming bone or cartilage, and hematopoietic cells. In some cases it may also be desirable to include nerve cells. The vasculature will typically be formed from endothelial cells. "Parenchymal cells" include the functional elements of an organ, as distinguished from the framework or stroma. "Mesenchymal cells" include connective and supporting tissues, smooth muscle, vascular endothelium and blood cells.

Cells can be obtained by biopsy or harvest from a living donor, cell culture, or autopsy, all techniques well known in the art. Cells are preferably autologous. Cells to be implanted can be dissociated using standard techniques such as digestion with a collagenase, trypsin or other protease solution and are then seeded into the mold or polymer scaffold immediately or after being maintained in culture. Cells can be normal or genetically engineered to provide additional or normal function. Immunologically inert cells, such as embryonic or fetal cells, stem cells, and cells genetically engineered to avoid the need for immunosuppression can also be used. Methods and drugs for immunosuppression are known to those skilled in the art of transplantation.

Undifferentiated or partially differentiated precursor cells, such as embryonic germ cells (Gearhart, et al., U.S. Pat. No. 6,245,566), embryonic stem cells (Thomson, U.S. Pat. Nos. 5,843,780 and 6,200,802), mesenchymal stem cells (Caplan, et al. U.S. Pat. No. 5,486,359), neural stem cells (Anderson, et al., U.S. Pat. No. 5,849,553), hematopoietic stem cells (Tsukamoto, U.S. Pat. No. 5,061,620), multipotent adult stem cells (Furcht, et al., WO 01/11011) can be used in this invention. Cells can be kept in an undifferentiated state by co-culture with a fibroblast feeder layer (Thomson, U.S. Pat. Nos. 5,843,780 and 6,200,802), or by feeder-free culture with fibroblast conditioned media (Xu, et al. *Nat. Biotechnol.,* 19, 971 (2001)). Undifferentiated or partially differentiated precursor cells can be induced down a particular developmental pathway by culture in medium containing growth factors or other cell-type specific induction factors or agents known in the art. Some examples of such factors are shown in Table 1.

TABLE 1

Selected Examples of Differentiation Inducing Agents

| Agent | Progenitor | Differentiated Cell |
|---|---|---|
| Vascular Endothelial Growth Factor | Embryonic Stem Cell | Hematopoietic Cell[1] |
| Sonic Hedgehog | Floor Plate | Motor Neuron[2] |
| Insulin-like Growth Factor II | Embryonic Stem Cell | Myoblast[3] |
| Osteogenin | Osteoprogenitor | Osteoblast[4] |
| Cytotoxic T Cell Differentiation Factor | Spleen Cell | Cytotoxic T Lymphocyte[5] |
| β-catenin | Skin Stem Cell | Follicular Keratinocyte[6] |
| Bone Morphogenic Protein 2 | Mesenchymal Stem Cell | Adipocytes, Osteoblasts[7] |
| Interleukin 2 | Bone Marrow Precursor | Natural Killer Cells[8] |
| Transforming Growth Factor β | Cardiac Fibroblast | Cardiac Myocyte[9] |

TABLE 1-continued

Selected Examples of Differentiation Inducing Agents

| Agent | Progenitor | Differentiated Cell |
|---|---|---|
| Nerve Growth Factor | Chromaffin Cell | Sympathetic Neuron[10] |
| Steel Factor | Neural Crest | Melanocyte[11] |
| Interleukin 1 | Mesencephalic Progenitor | Dopaminergic Neuron[12] |
| Fibroblast Growth Factor 2 | GHFT | Lactotrope[13] |
| Retinoic Acid | Promyelocytic Leukemia | Granulocyte[14] |
| Wnt3 | Embryonic Stem Cell | Hematopoietic Cell[15] |

[1]Keller, et al. (1999) *Exp. Hematol.* 27: 777-787.
[2]Marti, et al. (1995) *Nature.* 375: 322-325.
[3]Prelle, et al. (2000) *Biochem. Biophy. Res. Commun.* 277: 631-638.
[4]Amedee, et al. (1994) *Differentiation.* 58: 157-164.
[5]Hardt, et al. (1985) *Eur. J. Immunol.* 15: 472-478.
[6]Huelsken, et al. (2001) *Cell.* 105: 533-545.
[7]Ji, et al. (2000) *J. Bone Miner. Metab.* 18: 132-139.
[8]Migliorati, et al. (1987) *J. Immunol.* 138: 3618-3625.
[9]Eghbali, et al. (1991) *Proc. Natl. Acad. Sci.* USA. 88: 795-799.
[10]Niijima, et al. (1995) *J. Neurosci.* 15: 1180-1194.
[11]Guo, et al. (1997) *Dev. Biol.* 184: 61-69.
[12]Ling, et al. (1998) *Exp. Neurol.* 149: 411-423.
[13]Lopez-Fernandez, et al. (2000) *J. Biol. Chem.* 275: 21653-60.
[14]Wang, et al, (1989) *Leuk Res.* 13: 1091-1097.
[15]Lako, et al. (2001) *Mech. Dev.* 103: 49-59.

A stem cell can be any known in the art, including, but not limited to, embryonic stem cells, adult stem cells, neural stem cells, muscle stem cells, hematopoietic stem cells, mesenchymal stem cells, peripheral blood stem cells and cardiac stem cells. Preferably, the stem cell is human. A "stem cell" is a pluripotent, multipotent or totipotent cell that can undergo self-renewing cell division to give rise to phenotypically and genotypically identical daughter cells for an indefinite time and can ultimately differentiate into at least one final cell type.

The quintessential stem cell is the embryonal stem cell (ES), as it has unlimited self-renewal and multipotent and/or pluripotent differentiation potential, thus possessing the capability of developing into any organ, tissue type or cell type. These cells can be derived from the inner cell mass of the blastocyst, or can be derived from the primordial germ cells from a post-implantation embryo (embryonal germ cells or EG cells). ES and EG cells have been derived from mice, and more recently also from non-human primates and humans. Evans et al. (1981) *Nature* 292:154-156; Matsui et al. (1991) *Nature* 353:750-2; Thomson et al. (1995) *Proc. Natl. Acad. Sci. USA.* 92:7844-8; Thomson et al. (1998) *Science* 282: 1145-1147; and Shamblott et al. (1998) *Proc. Natl. Acad. Sci. USA* 95:13726-31.

The terms "stem cells," "embryonic stem cells," "adult stem cells," "progenitor cells" and "progenitor cell populations" are to be understood as meaning in accordance with the present invention cells that can be derived from any source of adult tissue or organ and can replicate as undifferentiated or lineage committed cells and have the potential to differentiate into at least one, preferably multiple, cell lineages.

The hepatocytes added to the apparatus of the invention can be highly proliferative hepatocytes, known as small hepatocytes (SHCs), which have the ability to proliferate in vitro for long periods of time (Mitaka, et al., *Biochem Biophys Res Commun* 214, 310 (1995); Taneto, et al, *Am J Pathol* 148, 383 (1996)). Small hepatocytes express hepatocyte specific functions such as albumin production (Mitaka, et al., *Hepatology* 29, 111 (1999)).

Methods for Seeding Cells into Molds or Polymer Scaffolds

After the mold with the desired high degree of micromachining is prepared, the molds themselves or polymer scaffolds are seeded with the desired cells or sets of cells. The distribution of cells throughout the mold or polymer scaffold can influence both (1) the development of a vascularized network, and (2) the successful integration of the vascular device with the host. The approach used in this invention is to provide a mechanism for the ordered distribution of cells onto the mold or polymer scaffold. Cells that are enriched for extracellular matrix molecules or for peptides that enhance cell adhesion can be used. Cells can be seeded onto the mold or polymer scaffold in an ordered manner using methods known in the art, for example, Teebken, et al., *Eur J. Vasa Endovasc. Surg.* 19, 381 (2000); Ranucci, et al., *Biomaterials* 21, 783 (2000). Also, tissue-engineered devices can be improved by seeding cells throughout the polymeric scaffolds and allowing the cells to proliferate in vitro for a predetermined amount of time before implantation, using the methods of Burg et al., *J. Biomed. Mater. Res* 51, 642 (2000).

For purposes of this invention, "animal cells" can comprise endothelial cells, parenchymal cells, bone marrow cells, hematopoietic cells, muscle cells, osteoblasts, stem cells, mesenchymal cells, stem cells, embryonic stem cells, or fibroblasts. Parenchymal cells can be derived from any organ, including heart, liver, pancreas, intestine, brain, kidney, reproductive tissue, lung, muscle, bone marrow or stem cells.

In one embodiment, the mold or polymer scaffold is first seeded with a layer of parenchymal cells, such as hepatocytes or proximal tubule cells. This layer can be maintained in culture for a week or so in order to obtain a population doubling. It can be maintained in a perfusion bioreactor to ensure adequate oxygen supply to the cells in the interior. The apparatus is then seeded with a layer of endothelial cells and cultured further. In regions where the matrix is resorbed rapidly, the tissue can expand and become permeated with capillaries.

Cell Seeding of Horizontal Layer by Laminar Flow

A structure comprising joined or fastened molds and/or polymer scaffolds, with or without a semi-permeable membrane between them, is called an "apparatus" for purposes of this invention. Sets of cells can be added to or seeded into the three-dimensional apparatuses, which can serve as a template for cell adhesion and growth by the added or seeded cells. The added or seeded cells can be parenchymal cells, such as hepatocytes or proximal tubule cells. Stem cells can also be used. A second set of cells, such as endothelial cells, can be added to or seeded onto the assembled apparatus through other vessels than those used to seed the first set of cells. The cell seeding is performed by slow flow. As a practical matter, the geometry of the apparatus will determine the flow rates. In general, endothelial cells can enter and form vessel walls in micromachined channels that are about 10-50 μm. Thus, in addition to serving as a mechanical framework for the organ, the assembled apparatus provides a template for all of the microstructural complexity of the organ, so that cells have a mechanical map to locate themselves and form subsystems, such as blood vessels in the liver.

Optionally, functional cells are seeded into both a first and second mold and/or polymer scaffold with microchannels on their surfaces, and the two molds and/or polymer scaffolds are joined or fastened with a semi-permeable membrane between them, allowing gas exchange, diffusion of nutrients, and waste removal. One layer comprises the circulation through which blood, plasma or media with appropriate levels of oxygen can be continuously circulated to nourish the second layer. The second layer comprises a reservoir for the functional cells of an organ, and optionally includes inlets for neural innervation, urine flow, biliary excretion or other activity. This results in an apparatus for making tissue lamina, wherein each of the first and second molds and/or polymer scaffolds and the semi-permeable membrane are comprised of material that is suitable for attachment and culturing of animal cells. The sheet of tissue created by the apparatuses and/or methods of the invention is referred to as "tissue lamina".

Channels in the horizontal direction typically proceed from larger to smaller to larger. The geometries can be as complex as desired in-plane (horizontal direction). Thus, one can use small geometries in-plane (such as horizontal conduits of about 5-20 μm). The alignment of through-holes creates vertical conduits or channels in the z-axis. However, the vertical channels need not go from larger to smaller to larger. In the vertical direction, the vertical channels are typically parallel to each other and have diameters on the micron level, large enough only to allow cell seeding (e.g., hepatocytes are about 40 μm). In one embodiment, different types of cells are seeded horizontally onto different layers of the assembled apparatus. In another embodiment, the different types of cells are seeded using pores or channels from different directions.

Although described herein with particular reference to formation of vascularized tissue, it should be understood that the channels can be used to form lumens for passage of a variety of different fluids, not just blood, but also bile, lymph, nerves, urine, and other body fluids, and for the guided regeneration or growth of other types of cells, especially nerve cells. The tissue layer can include some lumens for forming vasculature and some for other purposes, or be for one purpose, typically providing a blood supply to carry oxygen and nutrients to and from the cells in the tissue.

Molecules such as growth factors or hormones can be covalently attached to the surface of the molds and/or polymer scaffolds and/or semi-permeable membrane to effect growth, division, differentiation or maturation of cells cultured thereon.

EXAMPLES

The Examples presented herein demonstrates that present invention can be adapted to suit the needs of all living tissues. The following examples are put forth so as to provide those of ordinary skill in the art with a complete disclosure and description of how to make and use the three-dimensional systems of the invention, and are not intended to limit the scope of what the inventors regard as their invention. The Examples are provided to further describe the invention, and should not be considered to limit its scope in any way.

Example 1

Micromaching of Template to Tissue Engineer Branched Vascularized Channels for Liver Fabrication Micromachining technologies were used on silicon and pyrex surfaces to generate complete vascular systems that can be integrated with engineered tissue before implantation. Trench patterns reminiscent of branched architecture of vascular and capillary networks were etched using standard photolithographic techniques onto silicon and pyrex surfaces to serve as templates. Hepatocytes and endothelial cells were cultured and subsequently lifted as single-cell monolayers from these two dimensional molds. Both cell types were viable and proliferative on these surfaces. In addition, hepatocytes maintained albumin production.

Materials and Methods

Micromachining Techniques

Templates for the formation of sheets of living vascularized tissue were fabricated utilizing micromachining technology. For the present work, a single level etch was utilized to transfer a vascular network pattern into an array of connected trenches in the surface of both silicon and pyrex wafers.

In this prototype, a simple geometry was selected for patterning the vascular network. Near the edge of each wafer, a single inlet or outlet was positioned, with a width of 500 µm. After a short length, the inlet and outlet branched into three smaller channels of width 250 µm; each of these branched again into three 125 µm channels, and finally down to three 50 µm channels. Channels extend from the 50 µm channels to form a capillary network, which comprises the bulk of the layout. In between these inlet and outlet networks lies a tiled pattern of diamonds and hexagons forming a capillary bed and filling the entire space between the inlet and outlet. In one configuration, the capillary width was set at 25 µm, while in the other, capillaries were fixed at 10 µm. This geometry was selected because of its simplicity as well as its rough approximation to the size scales of the branching architecture of the liver. Layout of this network was accomplished using CADENCE software (Cadence, Chelmsford, Mass.) on a Silicon Graphics workstation. A file with the layout was generated and sent electronically to Align-Rite (Burbank, Calif.), where glass plates with electron-beam-generated patterns replicating the layout geometry were produced and returned for lithographic processing.

Starting materials for tissue engineering template fabrication were standard semiconductor grade silicon wafers (Virginia Semiconductor, Powhatan, Va.), and standard pyrex wafers (Bullen Ultrasonics, Eaton, Ohio) suitable for MEMS processing. Silicon wafers were 100 mm diameter and 525 µm thick, with primary and secondary flats cut into the wafers to signal crystal orientation. Crystal orientation was <100>, and wafers were doped with boron to a resistivity of approximately 5 W-cm. The front surface was polished to an optical finish and the back surface ground to a matte finish. Pyrex wafers were of composition identical to Corning 7740 (Corning Glass Works, Corning N.Y.), and were also 100 mm in diameter, but had a thickness of 775 µm. Both front and back surfaces were polished to an optical finish. Prior to micromachining, both wafer types were cleaned in a mixture of 1 part $H_2SO_4$ to 1 part $H_2O_2$ for 20 minutes at 140° C., rinsed 8 times in deionized water with a resistivity of 18 MW, and dried in a stream of hot $N_2$ gas.

For silicon and pyrex wafers, standard photolithography was employed as the etch mask for trench formation. Etching of pyrex wafers requires deposition of an intermediate layer for pattern transfer which is impervious to the etch chemistry. A layer of polysilicon of thickness 0.65 µm over the pyrex was utilized for this purpose. This layer was deposited using Low Pressure Chemical Vapor Deposition (LPCVD) at 570° C. and 500 mTorr via the standard silane decomposition method. In the case of silicon, photoresist alone could withstand limited exposure to two of the three etch chemistries employed. For the third chemistry, a 1.0 µm layer of silicon dioxide was thermally deposited at 1100° C. in hydrogen and oxygen.

Once the wafers were cleaned and prepared for processing, images of the prototype branching architecture were translated onto the wafer surfaces using standard MEMS lithographic techniques. A single layer of photoresist (Shipley 1822, MicroChem Corp., Newton, Mass.) was spun onto the wafer surfaces at 4000 rpm, providing a film thickness of approximately 2.4 µm. After baking at 90° C. for 30 minutes, the layer of photoresist was exposed to UV light using a Karl Suss MA6 (Suss America, Waterbury, Vt.) mask aligner. Light was passed through the lithographic plate described earlier, which was in physical contact with the coated wafer. This method replicates the pattern on the plate to an accuracy of 0.1 µm. Following exposure, wafers were developed in Shipley 319 Developer (MicroChem. Corp., Newton, Mass.), and rinsed and dried in deionized water. Finally, wafers were baked at 110° C. for 30 minutes to harden the resist, and exposed to an oxygen plasma with 80 Watts of power for 42 seconds to remove traces of resist from open areas.

Silicon wafers were etched using three different chemistries, while pyrex wafers were processed using only one technique. For pyrex, the lithographic pattern applied to the polysilicon intermediate layer was transferred using a brief (approximately 1 minute) exposure to $SF_6$ in a reactive-ion-etching plasma system (Surface Technology Systems, Newport, United Kingdom). Photoresist was removed, and the pattern imprinted into the polysilicon layer was transferred into trenches in the silicon using a mixture of 2 parts $HNO_3$ to 1 part HF at room temperature. With an etch rate of 1.7 µm per minute, 20 µm deep trenches were etched into the pyrex wafers in approximately 12 minutes. Since the chemistry is isotropic, as the trenches are etched they become wider. Processing with the layout pattern with 25 µm wide capillary trenches tended to result in merging of the channels, while the use of 10 µm wide trenches avoided this phenomenon. Interferometric analysis of the channels after etching showed that surface roughness was less than 0.25 µm. Once channel etching of pyrex wafers was completed, polysilicon was removed with a mixture of 10 parts $HNO_3$ to 1 part HF at room temperature, and wafers were re-cleaned in 1 part $H_2SO_4$ to 1 part HF.

Three different chemistries were employed to etch silicon in order to investigate the interaction between channel geometry and cell behavior. First, a standard anisotropic plasma etch chemistry, using a mixture of $SF_6$ and $C4F_8$ in a switched process plasma system from STS[24], was used to produce rectangular trenches in silicon. Narrower trenches are shallower than deep trenches due to a phenomenon known as RIE lag. A second process utilized a different plasma system from STS, which produces isotropic trenches with a U-shaped profile. While the process is isotropic, widening of the trenches is not as severe as is experienced in the isotropic pyrex etching process described earlier. In both of these plasma etching cases, trenches were etched to a nominal depth of 20 µm. For the third process, anisotropic etching in KOH (45% w/w in $H_2O$ at 88° C.), the intermediate silicon dioxide layer mentioned above was employed. First, the silicon dioxide layer was patterned using HF etching at room temperature. The KOH process produces angled sidewalls rather than the rectangular profile or U-shaped profile produced by the first two recipes, respectively. Crystal planes in the <111> orientation are revealed along the angled sidewalls, due to anisotropic properties of the KOH etch process as a function of crystal orientation. Due to the self-limiting nature of the channels produced by this process, trench depth was limited to 10 µm. After completion of the silicon wafer etching, all layers of photoresist and silicon dioxide were removed, and wafers were cleaned in 1 part $H_2SO_4$:1 part $H_2O_2$ at 140° C., followed by rinsing in deionized water and drying in nitrogen gas.

For this set of experiments, no attempt was made to alter the surface chemistry of the silicon and pyrex wafers. Prior to processing, silicon wafers were uniformly hydrophobic, while pyrex wafers were equally hydrophilic, as determined by observations of liquid sheeting and sessile drop formation. After processing, unetched surfaces appeared to retain these characteristics, but the surface chemistry within the channels was not determined.

Animals

Adult male Lewis rats (Charles River Laboratories, Wilmington, Mass.), weighing 150-200 g, were used as cell donors. Animals were housed in the Animal Facility of Massachusetts General Hospital in accordance with NIH guide lines for the care of laboratory animals. They were allowed rat chow and water ad libitum and maintained in 12-hour light and dark cycle

Cell Isolations

Male Lewis rats were used as hepatic cell donors. HCs were isolated using a modification of the two-step collagenase perfusion procedure as previously described by Aiken, et al., *J Pediatr Surg* 25, 140 (1990) and Seglen, *Methods Cell Biol* 13, 29 (1976). Briefly, the animals were anesthetized with Nembutal Sodium Solution (Abbott Laboratories, North Chicago, Ill.), 50 mg/kg, and the abdomen was prepared in sterile fashion. A midline abdominal incision was made and the infrahepatic inferior vena cava was cannulated with a 16-gauge angiocatheter (Becton Dickinson). The portal vein was incised to allow retrograde efflux and the suprahepatic inferior vena cava was ligated. The perfusion was performed at a flow rate of 29 ml/min initially with a calcium-free buffer solution for 5 to 6 minutes, then with a buffer containing collagenase type 2 (Worthington Biomedical Corp., Freehold, N.J.) at 37° C. The liver was excised after adequate digestion of the extracellular matrix and mechanically agitated in William's E medium (Sigma, St. Louis, Mo.) with supplements to produce a single cell suspension. The suspension was filtered through a 300 μm mesh and separated into two fractions by centrifugation at 50 g for 2 minutes at 4° C. The pellet containing the viable HC fraction was resuspended in William's E medium and further purified by an isodensity Percoll centrifugation. The resulting pellet was then resuspended in Hepatocyte Growth Medium, and cell counts and viabilities of HCs were determined using the trypan blue exclusion test.

The endothelial cells were derived from rat lung microvessels and they were purchased directly from the vendor, Vascular Endothelial Cell Technologies (Rensellaer, N.Y.).

Hepatocyte Culture Medium

William's E medium supplemented with 1 g sodium pyruvate (Sigma, St. Louis, Mo.) and 1% glutamine-penicillin-streptomycin (Gibco BRL, Gaithersburg, Md.) were used during the cell isolation process. The plating medium was Dulbecco's modified eagle medium (Gibco BRL) supplemented with 10% fetal bovine serum, 1% penicillin-streptomycin, 44 mM sodium-bicarbonate, 20 mM HEPES, 10 mM niacinamide, 30 microgram/ml L-proline, 1 mM ascorbic acid 2 phosphate, 0.1 μM dexamethasone (Sigma), insulin-transferrin-sodium selenite (5 mg/L-5 mg/L-5 μgram/L, Roche Molecular Biomedicals, Indianapolis, Ind.), and 20 ng/mL epidermal growth factor (Collaborative Biomedical Products, Bedford, Mass.).

Endothelial Cell Culture Medium

Dulbecco's modified eagle medium (Gibco BRL) was supplemented with 10% fetal bovine serum, 1% penicillin-streptomycin, 25 mg of ascorbic acid (Sigma), 10 mg L-alanine (Sigma), 25 mg L-proline (Sigma), 1.5 microgram cupric sulfate (Sigma), glycine (Sigma) and 1M Hepes buffer solution (Gibco BRL). The media was supplemented with 8 mg of ascorbic acid every day.

Cell Attachment to Non-Etched Silicon and Pyrex Wafers

Silicon and pyrex were both tested as possible substrates for the culture of endothelial cells and hepatocytes. Prior to cell seeding, the pyrex wafers were sterilized with 70% ethanol (Fisher, Pittsburgh, Pa.) overnight and washed three times with sterile phosphate buffered saline (Gibco BRL). Silicon wafers were first soaked in acetone for 1 hr, followed a methanol rinse for 15 minutes, and overnight sterilization in 100% isopropyl alcohol. Rat lung microvascular endothelial cells was cultured on non-coated pyrex and silicon surfaces, as well as wafers coated with vitrogen (30 microgram/ml), Matrigel® (1%), or Gelatin (10 mg/ml). Once isolated, the cells were resuspended in endothelial cell culture medium, seeded uniformly onto the wafer at a density of $26.7 \times 10^3$ cells/cm$^2$, and cultured at 5% $CO_2$ and 37° C.

The rat hepatocytes were also cultured on non-coated pyrex and silicon, as well as wafers coated with a thin and thick layers of vitrogen (30 microgram/ml and 3 microgram/ml) and Matrigel (1%) in order to determine the optimal methods for lifting hepatocyte sheets. Once isolated, the hepatocytes were resuspended in hepatocyte growth media, seeded onto the wafer at a density of $111.3 \times 10^3$ cells/cm$^2$, and cultured at 5% $CO_2$ and 37° C. Cell attachment and growth was observed daily using microscopy.

Immunohistochemical Staining

Both membranes were fixed in 10% buffered formalin for 1 hr and harvested for histological study, and the hepatocytes were stained immunohistochemically.

The hepatocyte cell monolayer membrane was fixed in 10% buffered formalin and processed for hematoxylin-eosin and immunohistochemical staining using a labeled streptavidin biotin method (LSAB2 kit for rat specimen, DAKO, Carpinteria, Calif.). The primary antibody was rabbit anti-albumin (ICN, Costa Mesa, Calif.). Three-micron sections were prepared and deparafinized. The specimens were treated with peroxidase blocking buffer (DAKO) to prevent the non-specific staining. Sections were stained with albumin diluted with phosphate buffered saline, followed by biotinylated anti-rabbit antibody and HRP conjugated streptavidin. Sections were treated with DAB as substrate and were counterstained with hematoxylin.

Albumin Production

Figure 10:
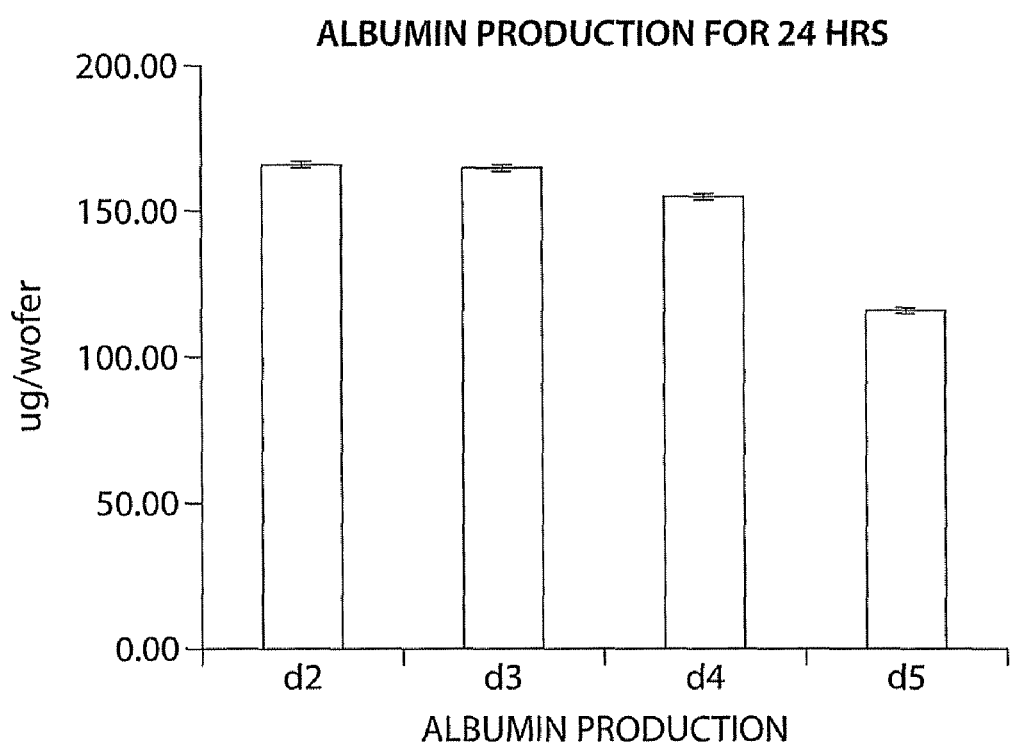
FIG. 10 shows a set of bar graphs demonstrating continued albumin production by hepatocyte cells cultured in a polymer scaffold of the invention. Albumin concentration in culture medium was measured every 24 hours for 5 days pre-cell detachment using an enzyme linked immunosorbent assay. No significant differences were observed between day 2, day 3, and day 4 ($p<0.05$ by the paired t-test).

To assess hepatocyte function, albumin concentration in the culture medium was measured every 24 hours for 5 days pre-cell detachment using an enzyme linked immunosorbent assay (n=5), as described by Schwere, et al., *Clinica Chemica Acta* 163, 237 (1987). In brief, a 96 well microplate was coated with anti-rat albumin antibody (ICN). After blocking non-specific responses with a 1% gelatin solution, each sample was seeded onto the plate and incubated for 1 hour at 37° C. This was followed by another 1 hour incubation with peroxidase conjugated anti-rat albumin antibody (ICN). Finally, the substrate was added and extinction was measured with a microplate reader at 410 nm. $R^2$ of the standard curve was >0.99. Results demonstrate continued production of albumin by cultured hepatocytes (FIG. 10).

Statistical Analysis

All data was expressed as mean±SD. Statistical analysis was performed with a paired t-test. Statistical significance was determined as when the p value of each test was less than 0.05.

Cell Attachment to Etched Silicon and Pyrex Wafers

Endothelial cells and hepatocytes were also seeded onto etched silicon and pyrex wafers. Prior to cell seeding, the pyrex wafers were sterilized with 70% ethanol (Fisher) overnight and washed three times with sterile phosphate buffered saline (Gibco BRL). Silicon wafers were first soaked in acetone for 1 hr, followed a methanol rinse for 15 minutes, and overnight sterilization in 100% isopropyl alcohol. Onto these wafers were seeded rat lung microvascular endothelial cells at a density of $26.7 \times 10^3$ cells/cm$^2$, or rat hepatocytes at a density of $111.3 \times 10^3$ cells/cm$^2$. These cells were cultured at 5% $CO_2$ and 37° C., and their attachment and growth observed daily using microscopy.

Results

Micromachining

Figure 11A:
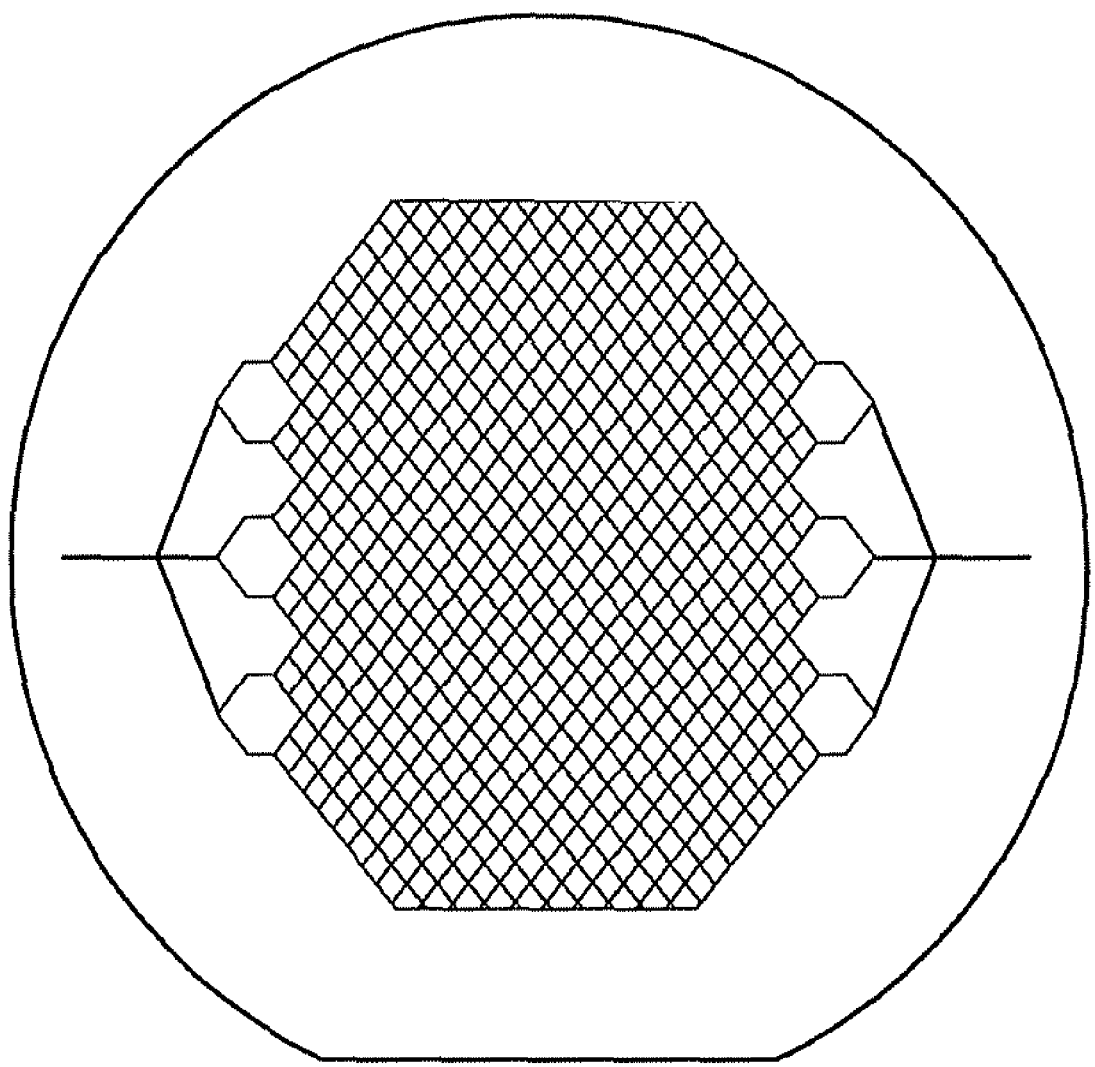
FIG. 11A shows a sample vascular branching network pattern used for silicon and pyrex wafer micromachining.
Figure 11B:
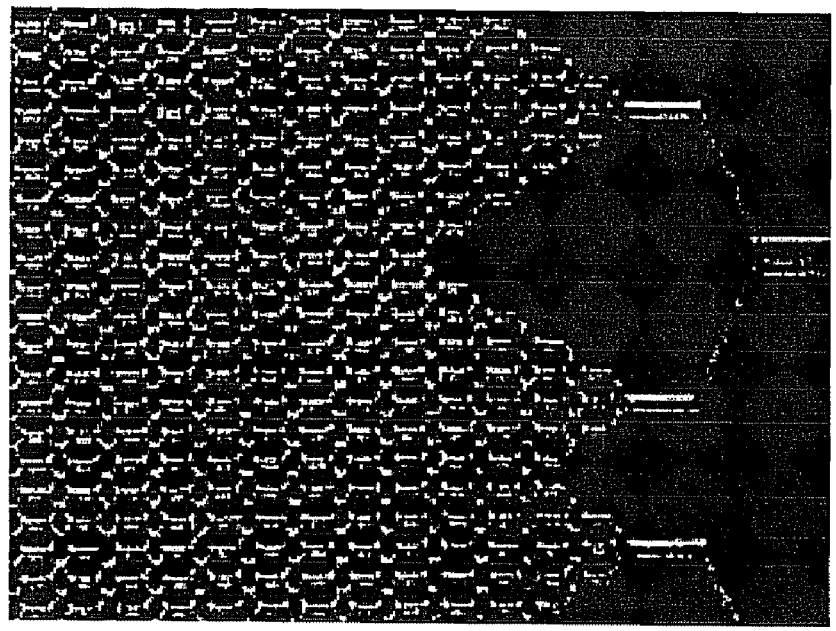
FIG. 11B shows the optical micrograph or portion of a capillary network etched into a silicon wafer.
Figure 11C:
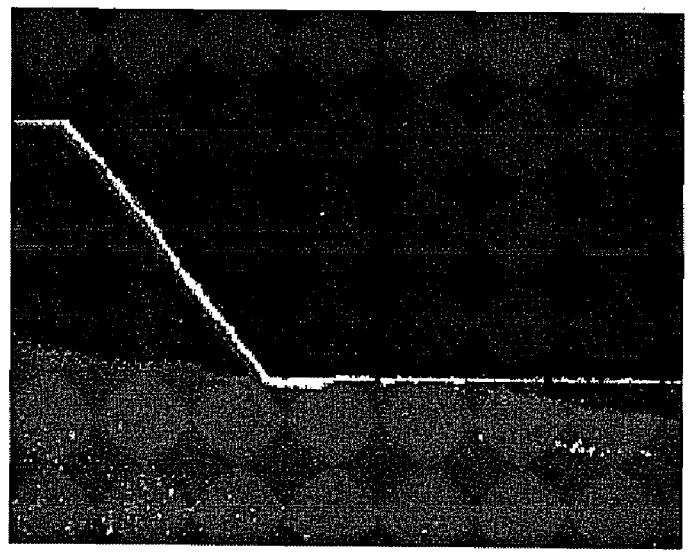
FIG. 11C shows a scanning electron micrograph of an anisotrophic etching process used to form angled sidewall trenches.

A schematic of the vascular branching network design used as a template for micromachining is shown in FIG. 11A. This pattern was transferred to silicon and pyrex wafers using the processes described in the Materials and Methods section. Typical trench depths of 20 μm on silicon and 10 μm on glass were achieved utilizing these processes. An optical micrograph of a portion of the capillary network etched into a silicon wafer is shown in FIG. 11B. In FIG. 11C, a Scanning Electron Micrograph cross-section of an angled trench etched using the anisotropic etching process described earlier is shown. This process resulted in excellent adhesion and enhanced lifting of living tissue.

Growth of Cells on Silicon and Pyrex Wafers

The adhesion and growth of endothelial cells and hepatocytes on several different substrate surfaces were compared. On all pyrex wafers, coated or non-coated, the endothelial cells proliferated and grew to confluence within four days. Hepatocytes also attached and spread well on all coated and non-coated pyrex wafers. Histological assessment of the detached cell monolayers of both hepatocytes and endothelial cells manifested promising results. Hemotoxylin and Eosin (H&E) staining of both showed that all cells were viable and that most were undergoing mitoses. The endothelial cells were observed to be primarily attenuated and to form a single-celled alignment. The monolayer of hepatocytes showed each cell to be of a spheroid configuration with eosinophilic flocculent cytoplasm and a large nucleus with a bright red nucleolus, similar to that seen in the native liver. Moreover, cellular attachments were less attenuated than the endothelial cells. Thus, these results are reminiscent of each of the cell types' specific functions. In biological systems, the endothelium functions to provide a thin, smooth outer surface of a barrier and a transport channel and so it is understandable that these cells are observed here to be primarily attenuated and in a single-celled array. The hepatocytes have more of a tendency to form tissue and so less of a single-celled array and more of a rounded multi-layered array is seen.

Albumin secretion into the hepatocyte culture medium at day 2, 3, 4, and 5 was 165.96±29.87, 164.44±17.22, 154.33±18.46, 115.47±18.09 (microgram/day, Graph 1), respectively. Though there was a statistically significant difference between day 4 and day 5, no significant differences were observed between day 2, day 3, and day 4 ($p<0.05$ by the paired t-test). Hence, this data shows that cells cultured on silicon wafers were able to maintain a fairly constant albumin production rate until day 4.

Moreover, through immunohistochemical staining of the detached hepatocyte monolayers, many cells were stained positive for albumin indicating further that hepatocyte function was maintained on silicon wafers.

Implantation of Hepatocyte Sheet into the Rat Omentum

H&E staining of hepatocyte sheets implanted into rat omentum demonstrated that all cells were viable and showed proliferation at four weeks and three months. The implanted hepatocyte monolayer sheets, when harvested, were over 5 cell layers thick in most areas.

This study demonstrates that silicon microfabrication technology can be utilized to form large sheets of living tissue. It also demonstrates the feasibility of etching ordered branching arrays of channels that allow living endothelial cells to line the luminal surface of the channels. In addition, it has been shown that organized sheets of engineered hepatocyte tissue and endothelial tissue can be lifted from the surface of silicon or pyrex wafers and can be folded into a compact three-dimensional configuration. The hepatocyte sheets have then been placed into rats on the highly vascular surface of the omentum. That structure has then been rolled into a three-dimensional cylinder as a model for an engineered vasculature. Vascularized hepatic tissue was formed as a permanent graft.

Example 2

Endothelialized Microvascular Networks Grown on Micromachined Pyrex® Templates for Tissue Engineering of Vital Organs This Example shows the design, modeling, and experimental/computational testing of the endothelialized microvascular matrices grown on micromachined Pyrex® templates.

Patterns of microvascular networks were etched using microfabrication technologies on Pyrex® wafers. The pattern consisted of 10 generations of bifurcations from a single inflow channel of width 3 mm down to channels of width of 30 μm.

The channels were then collected to a single outflow. All channels were etched to the same depth of 30 μm. The Pyrex® wafer was sealed to a flat silicone rubber sheet of the same size. Endothelial cells harvested from rat lung were successfully seeded and expanded under continuous flow conditions in this microvascular network. Red blood cells harvested from rat were heparinized and perfused into the endothelialized channels, and successfully collected at the output. Using micro-visualization techniques, the concentration of red blood cells (hematocrit) in the microvascular network was measured. The distribution of blood flow rate, pressure, and hematocrit was also calculated in the entire microvascular system using an earlier developed computational algorithm.

Epithelial cells were observed flowing through channels and attaching mainly around the walls of smallest channels on day 1 and growing to confluence along the channels under continuous flow conditions over the following 5 days. Rat lung endothelial cells attach in a single layer to the walls of these mold structures without occluding them.

Hematocrit compared well between the experimental measurements and numerical calculations. Red blood cells reach even the smallest vessels in the network, ensuring sustained transport of oxygen to the engineered capillaries.

In summary, microfabrication technology is demonstrated as an approach for organizing endothelial cells in vitro at the size scale of the microcirculation.

Example 3

Microfluidics Device for Tissue Engineering Microvasculature Endothelial Cell Culture In this Example, the fabrication of the microfluidic mold, in vitro seeding, and extended cell culture in the mold is demonstrated. Capillary networks were fabricated in biocompatible PDMS, sterilized, coated with cell adhesion molecules, and seeded with cells. Cell-containing molds were then connected to a closed-loop bioreactor for long-term culture. Continuous-flow culture of endothelial cells for up to 4 weeks without occlusion or contamination was achieved.

Traditional soft lithography microfluidics were used as a prototype matrix. These cell-containing microfluidics are capable of supporting long-term culture in vitro, because in vitro expansion of cells prior to implantation can take several weeks. The prototype matrix is designed to supply sufficient oxygen and nutrients and to remove excretory products while avoiding large shear stresses. The matrix is useful for long-term microfluidic cell culture, including the maintenance of sterility and the minimization of cell and bubble occlusions.

Microfluidic networks that support physiologic flows and pressures were developed by photopatterning SU-8, a high-aspect ratio negative photoresist, onto silicon. This was used as a mold for casting polydimethylsiloxane (PDMS). After removal from the mold, inlets and outlets were cored with blunted syringe needles, and the micropatterned polymer scaffold was irreversibly sealed to an unpatterned layer of Pyrex® or PDMS by oxygen plasma surface treatment. See Duffy, et al., *Anal. Chem.* 70, 4974 (1998). The microfluidic device was autoclave sterilized and perfused with a solution containing cell adhesion molecules (poly-L-lysine, collagen, gelatin, or fibronectin), which were allowed to adsorb for one hour.

The fluidic network was then seeded with a $1\times10^6$-$1\times10^8$ cells/mL cell suspension using a syringe pump at flow rates ranging from 10-100 µL/min. The cells were then allowed to attach for 24 hours, after which the device was connected in-line with a sterile bioreactor consisting of a peristaltic pump, oxygenator, bubble trap, and a reservoir of sterile culture medium. Sterile culture medium was pumped peristaltically from a sterile reservoir through an oxygenator consisting of along length of tubing semipermeable to oxygen. The oxygenator was followed by a small bubble trap, leading directly to the microfluidic circuit. Finally, the system was run closed-loop in an incubator at standard culture settings.

Autoclave sterilization of the microfluidic circuit caused no obvious pattern distortion. Coating the channels with cell adhesion molecules enhanced cell attachment when compared to phosphate buffered saline-coated control channels. Seeding of cells into channels of widths between 30-200 mm was optimized by varying concentrations and flow rates. The continuous-flow bioreactor was used to dynamically culture endothelial cells at flow rates between 0.01 mL/min and 0.1 mL/min. Both single channels and complex networks of channels (30-200 µm wide and 40 µm deep) were successfully seeded and cultured. In 100 µm×40 µm single channels, cells were cultured for more than 4 weeks without contamination or occlusion.

Long-term culture of cells in microfluidic devices was achieved. Cells successfully attached, proliferated, and migrated in closed microfabricated channels with small geometries.

Example 4

Generation of Functionally Differentiated, Three-Dimensional Hepatic Tissue from Two-Dimensional Sheets of Small Hepatocytes and Non-Parenchymal Cells In this Example, three-dimensional, vascularized liver tissue was fabricated in vivo from a non-vascularized monolayer or cell sheet of small hepatocytes (SHCs) formed on a silicon wafer. SHCs cells are smaller than mature hepatocytes (MHCs), but morphologically similar, with a highly proliferative capacity (Mitaka, et al., *Biochem Biophys Res Commun* 214, 310 (1995); Mitaka, et al., *Gastroenterol Hepatol* 13 Suppl, S70 (1998); Mitaka, et al., *Hepatology* 29, 111 (1999); Tateno, et al., *Am J Pathol* 148, 383 (1996); Tateno, et al., *Am J Pathol* 149, 1593 (1996)).

Cell sheets created from SHCs and NPCs were implanted onto rat omentum with maximal hepatotrophic stimulation by retrorsine, portacaval shunt, and partial hepatectomy, and their engraftment and function were evaluated. Using this cell type, co-cultured with non-parenchymal cells (NPCs), liver tissue that maintained a high level of albumin production was fabricated in a flow culture system. Animals as described in Example 1 were used as cell donors. Cells were cultured as described in the Hepatocyte Culture Medium section of Example 1.

Cell Isolation

SHCs and NPCs were isolated by the process described in Example 1, with the following modifications. Animals were anesthetized by an intramuscular injection with Ketamine and Xylazine. Cells were collected, suspended, filtered and centrifuged as previously described. Following centrifugation, the pellet containing a majority of MHCs was discarded. The supernatant was collected, and the fraction containing SHCs and NPCs was obtained as a pellet by additional centrifugation twice at 150×g for 5 minutes. The pellet was resuspended in the plating medium and the cell number and viability were counted using the trypan blue exclusion test.

In Vitro SHC Sheets Preparation

In order to obtain SHC sheets, the SHCs and NPCs were seeded and cultured on silicon wafers (10 cm diameter). Briefly, the silicon wafers were sterilized with ethylene oxide gas and coated with liquid collagen (Vitrogen 100, Collagen Corp., Palo Alto, Calif.). The mixture of SHCs and NPCs was resuspended in the plating medium at a density of $0.8\times10^6$ cells/mL. A 25 mL suspension was seeded onto the silicon wafer in a 15 cm Petri dish and incubated at 37° C., 5% $CO_2$. The plating medium was changed every other day.

Albumin Production

To assess SHC function before implantation, albumin concentration in the plating medium was measured at 3, 5, 7 and 10 days after cell seeding using an enzyme linked immunosorbent assay (ELISA) (n=11) as described in Example 1.

In Vivo Model

Retrorsine was administered into the peritoneal cavity of recipient rats (n=23) at a dose of 3 mg/ml/100 g on day 0, and after two weeks as previously reported (Laconi, et al., *Am J. Pathol* 153, 319 (1998)). Three weeks after the second administration, an end-to-side portacaval shunt was created using 8-0 Ethilon suture (ETHICON, Somerville, N.J.) to generate systemic hepatotrophic stimulation for SHC sheet implantation. One week later, a SHC sheet was spread onto the rat omentum and rolled from distal to proximal into a three-dimensional cylinder. The omentum was sutured to the anterior wall of the stomach using 7-0 Prolene suture (ETHICON). A 60% partial hepatectomy was performed simultaneously for hepatotrophic stimulation. Animals were sacrificed at the designated time points after SHC sheet implantation for specimen retrieval. The resected specimens were fixed in 10% formalin solution (Sigma), routinely processed and embedded in paraffin for subsequent hematoxylin-eosin (H & E) and immunohistochemical staining. Two specimens were fixed in 2.5% gluteraldehyde (Sigma) for electron microscopy (EM).

Immunohistochemical Staining

To characterize the implanted constructs, immunohistochemical staining using the Avidin-biotin peroxidase complex (ABC) method was performed. The primary antibodies included: rabbit anti-albumin (DAKO, Carpinteria, Calif.), rabbit anti-transferrin (ICN), mouse anti-pancytokeratin (Sigma), goat anti-γ-glutamyl transpeptidase (GTT) (a gift from Dr. Petersen, Department of Pathology, University of Florida, FL). Four μm paraffin sections were deparaffinized and treated with 4.5% $H_2O_2$ in methanol. The specimens were digested for 12 minutes with 0.1% trypsin solution, followed by treatment with avidin D (Vector) and 5% serum. Subsequently, slides were incubated with the respective primary antibody that were diluted in phosphate buffered saline with 1% bovine serum albumin overnight at 4° C. Biotinylated anti-mouse/rabbit/goat antibody was used as a secondary antibody in combination with the Vectastain ABC kit (Vector, Burlingame, Calif.). Finally, specimens were treated with 3-amino-9-ethylcarbazole (AEC) (Vector) as substrate and were counterstained with Mayer's hematoxylin solution (Sigma).

Electron Microscopy (EM)

Two rats at 4 months were sacrificed for EM study. Immediately after removal from the animal, 1 mm sections were placed into Karnovsky's KII solution (2.5% glutaraldehyde, 2.0% paraformaldehyde, 0.025% calcium chloride, in a 0.1 M sodium cacodylate buffer, pH 7.4), fixed overnight at 4° C., and routinely processed for EM. Representative areas were chosen from 1 μm sections stained with toluidine blue. The sections were examined using a Phillips 301 transmission electron microscope.

Morphologic and Quantitative Analysis

For morphologic and quantitative analysis, specimens were harvested at 2 weeks (n=7), 1 month (n=7), and 2 months (n=7). At each time point, the rolled omentum was cut perpendicularly to the greater curvature of stomach, and three to four cross-sections of tissue were obtained and stained with H & E. The area occupied by implanted constructs in each section was measured using computer assisted analysis with NIH Image version 1.61 software (Division of Computer Research and Technology, NIH, Bethesda, Md., USA). This was expressed as $\mu m^2$/section.

Statistical Analysis

All values are expressed as mean f SD and were statistically evaluated using the Mann-Whitney test or the paired t-test. A value of $p<0.05$ was considered statistically significant.

Cell Isolation and Growth in a Culture Flask

Figure 12A:
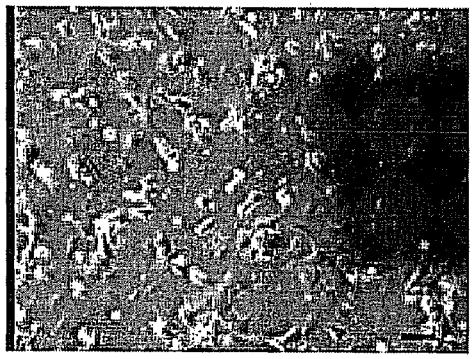
FIG. 12A shows cells in culture at Day 3.
Figure 12B:
FIG. 12B shows cells in culture at Day 5.
Figure 12C:
FIG. 12C shows cells in culture at Day 10. Scale bar, 100 μm (original magnification ×100).

All cell isolations yielded $8\text{-}14 \times 10^7$ cells comprising SHCs and NPCs with >90% overall viability. To evaluate the culture condition of SHCs on silicon wafers, a cell suspension was seeded on culture flasks at the same concentration. One day after seeding, most cells began to attach individually or occasionally form small clusters consisting of several SHCs. After 3 days, cells have completely attached and spread on the culture flask. After 5 days, many clusters had formed and NPCs were observed between the clusters. These small clusters united to form larger clusters and continued to grow until implantation (FIG. 12).

Cell Sheet Formation

Figure 13A:
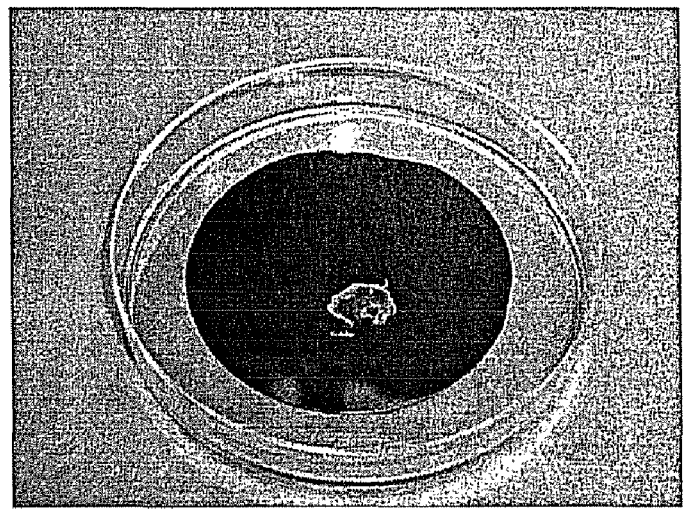
FIG. 13A shows macroscopic appearance and FIG. 13B shows microscopic appearance (original magnification ×30).
Figure 13B:
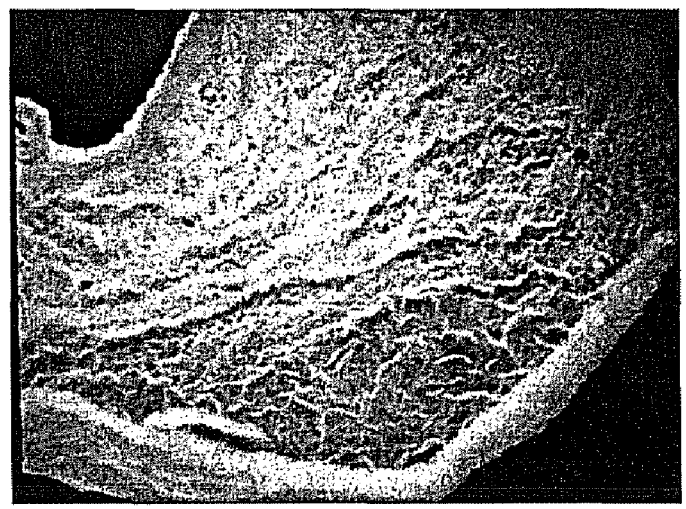

SHCs and NPCs cultured on silicon wafers grew similarly to the culture flask. Many large clusters were observed macroscopically on the silicon wafers after culturing for 10-14 days. Cultured cells were lifted as a sheet from all the silicon wafers. After lifting, cell sheets shrunk to approximately 2.5 cm in diameter (FIG. 13).

Albumin Production

Figure 14:
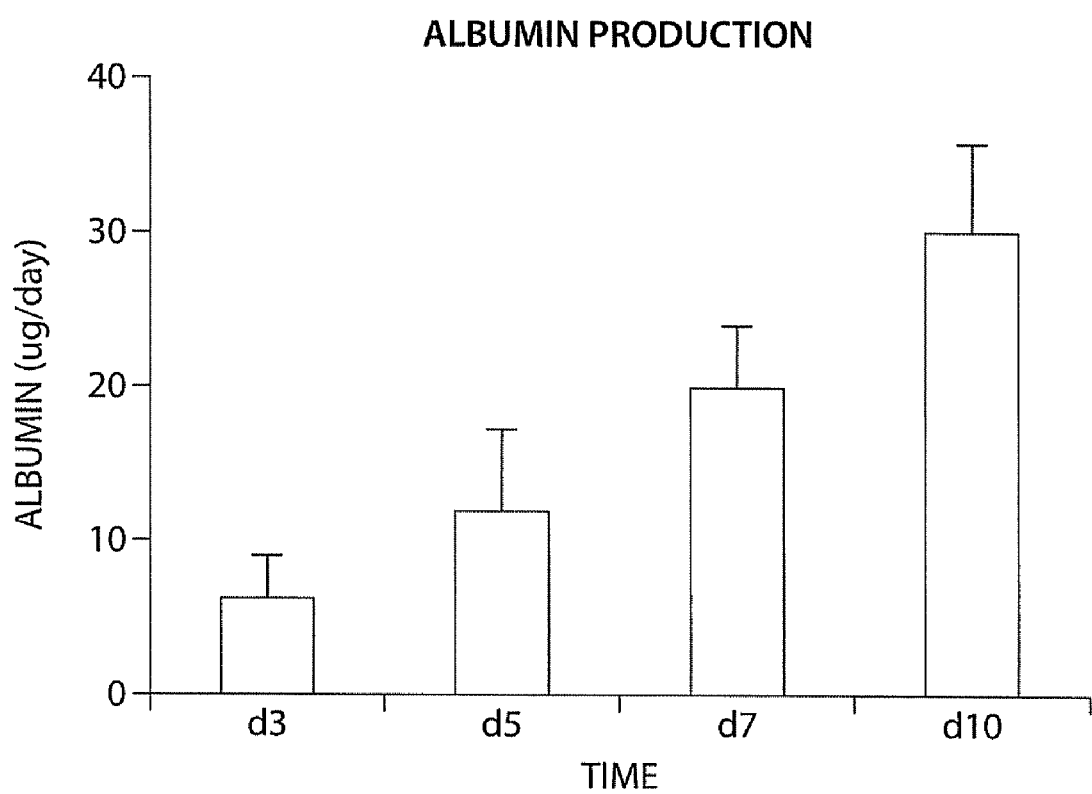
FIG. 14 shows albumin production by small hepatocytes at day 3, 5, 7, and 10 (μg/day).

Albumin secretion at day 3, 5, 7, and 10 was, 6.47±2.49, 12.08±5.18, 19.93±4.05, 30.14±5.46 (μg/day), respectively (FIG. 14). There were statistically significant differences between day 3 and day 5, day 5 and day 7, and day 7 and day 10 ($p<0.05$ by the paired t-test).

H & E Staining

Figure 15A:
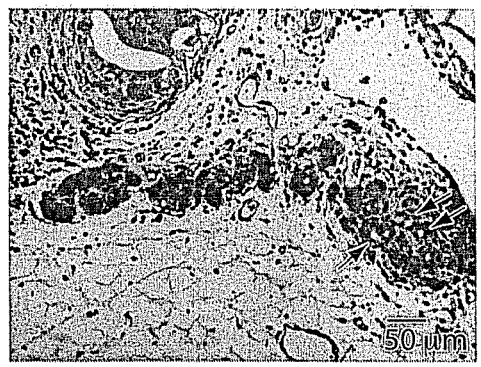
FIG. 15A shows constructs at 2 weeks. Arrows indicate bile ductular structures.
Figure 15B:
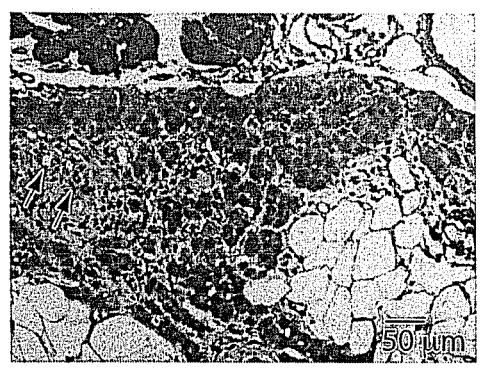
FIG. 15B shows constructs at 1 month. Arrows indicate bile ductular structures.
Figure 15C:
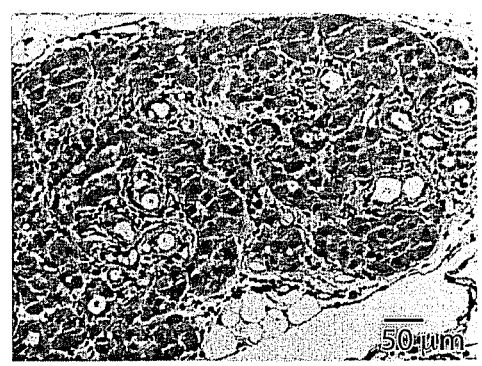
FIG. 15C shows constructs at 2 months. The large clusters of hepatocytes over five cell layers thick were observed at 1 and 2 months.
Figure 15D:
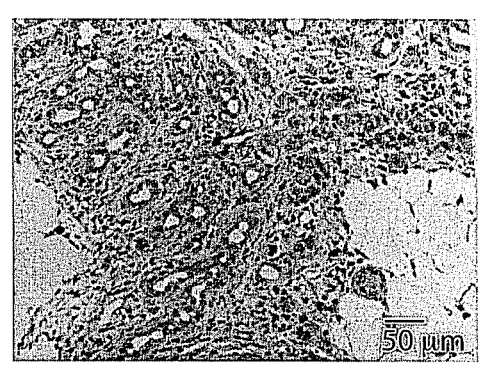
FIG. 15D shows constructs at 1 month. The implanted construct was occupied by the bile ductular structures.

The H & E staining of specimens harvested at 2 weeks after cell sheet implantation typically reveal large, polygonal, eosinophilic cells with round nuclei resembling hepatocytes, cuboidal cells resembling biliary epithelial cells, and capillary formation. At this time point the area of hepatocytes was less than five cell layers thick (FIG. 15A). At 1 and 2 months, large clusters of hepatocytes over five cell layers thick, cuboidal cells resembling biliary epithelial cells, and capillary formation could be observed (FIG. 15B-D). In some areas, hepatocytes exceeded ten cells layer thick. In the specimens at 2 weeks and 1 month, there were many areas that were occupied mainly by bile duct-like structures (FIG. 15D). As the implant matured in the omentum, the number of hepatocytes increased and the number of bile duct-like structures decreased at 2 months.

Immunohistochemistry

Figure 16A:
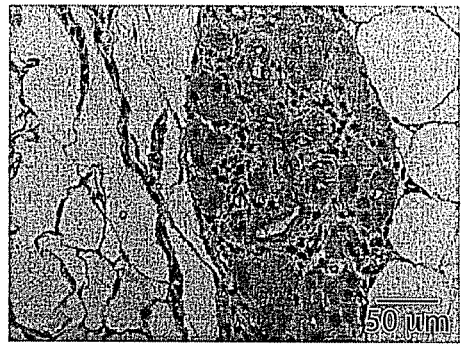
FIG. 16A shows pan-cytokeratin staining at 1 month.
Figure 16B:
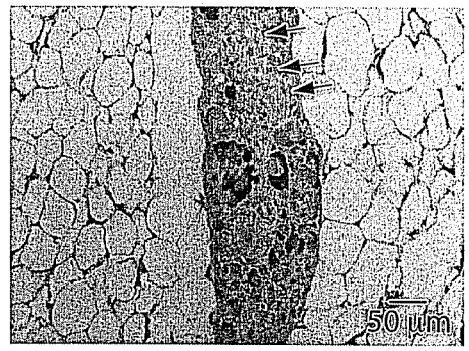
FIG. 16B shows albumin staining at 1 month. Arrows indicate bile ductular structures.
Figure 16C:
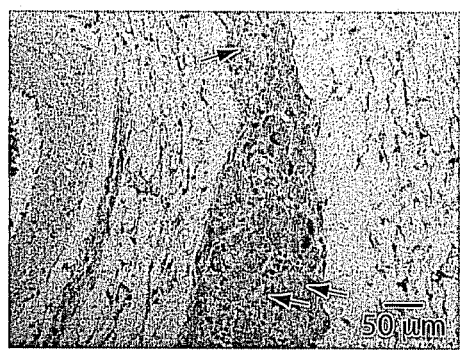
FIG. 16C shows transferrin staining at 1 month. Arrows indicate bile ductular structures.
Figure 16D:
FIG. 16D shows GGT staining at 1 month. Arrows indicate bile ductular structures with luminal staining. Arrow heads indicate slightly stained hepatocytes.

Both hepatocytes and bile duct-like structures stained positively with pan-cytokeratin. However, bile ductules stained more strongly positive than hepatocytes (FIG. 16A). Since there are normally no pan-cytokeratin positive cells in the omentum, it is likely that the cells originated from the implanted constructs. Some of the hepatocytes stained positively for albumin and transferrin, which suggests that they continued to express liver specific functions. The bile duct-like structures stained positively for GGT, an enzyme expressed at high levels in normal rat intrahepatic biliary epithelial cells but typically not detected in normal rat hepatocytes, and negatively for albumin and transferrin, which indicated that they were composed of cells resembling normal biliary epithelial cells (FIG. 16B-D).

Figure 17:
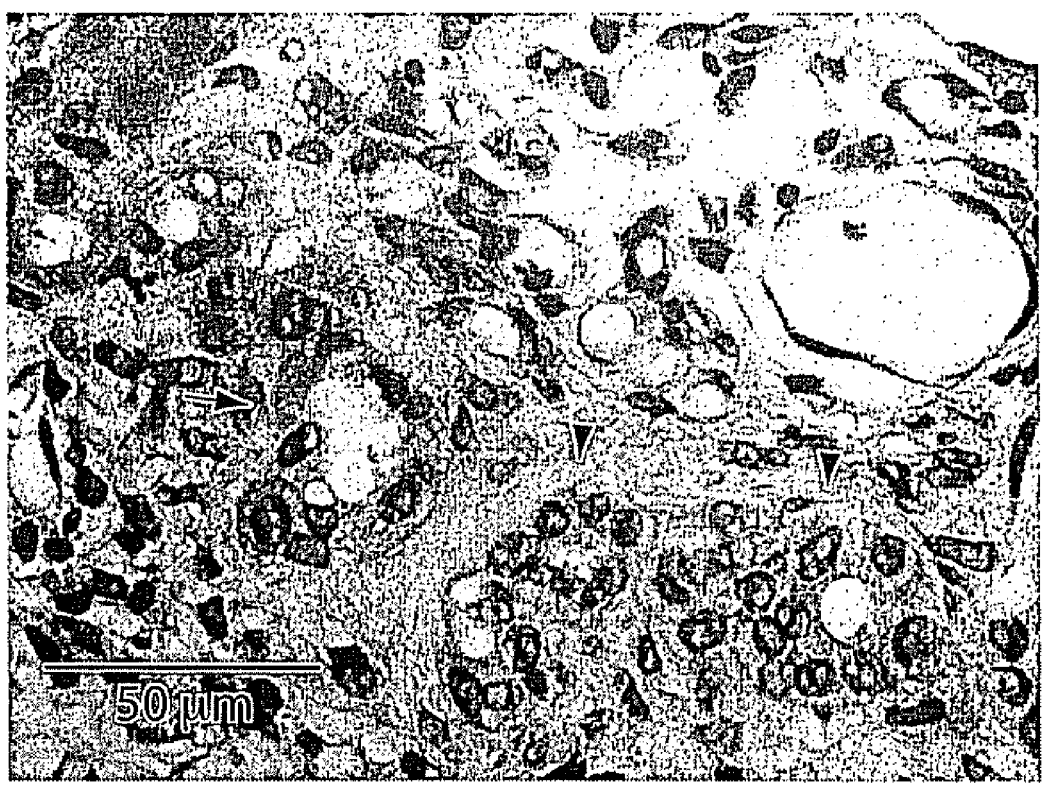
FIG. 17 shows H & E staining at 1 month. Arrow indicates the bile ductular structure composed of both biliary epithelial cells and a hepatocyte. Arrow heads indicate the bile ductular structures composed of biliary epithelial cells.

In one case, histology showed that one bile duct-like structure at 2 weeks was formed with both cells resembling biliary epithelial and cells which were morphologically more similar to hepatocytes (FIG. 17). This bile duct-like structure was located between the canaliculi-like structures composed of hepatocytes, and the bile duct-like structures formed solely by cells resembling biliary epithelial as if it were a transitional structure between the two. This phenomenon demonstrates that canaliculi-like structures and bile duct-like structures grow to confluence in tissue engineered constructs.

Ultrastructure of the Implanted Construct

Figure 18A:
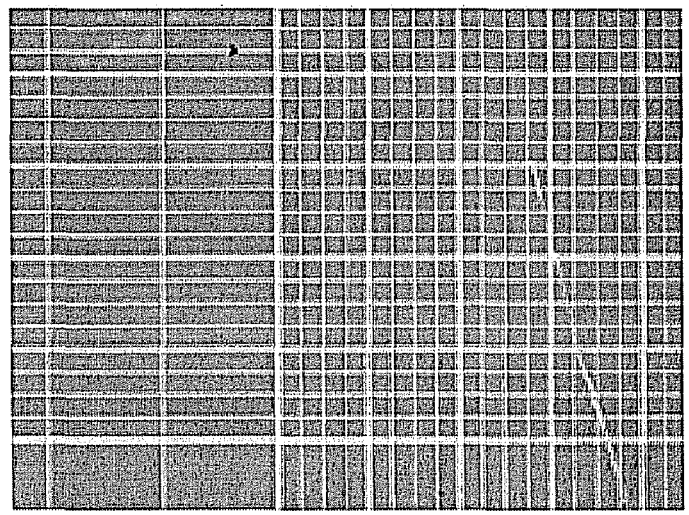
FIG. 18 shows transmission electron microscopy (TEM) of an implanted construct. (A) Low magnification (×2500). (B) High magnification (×15000).
Figure 18B:

TEM revealed that the engineered constructs were composed of cells with large round nuclei, numerous mitochondria and peroxisomes, and microvilli; characteristic of hepatocytes. These cells formed structures resembling bile canaliculi at the cell-cell borders. Capillaries were seen between hepatocytes (FIG. 18B).

Morphologic and Quantitative Analysis

Figure 19:
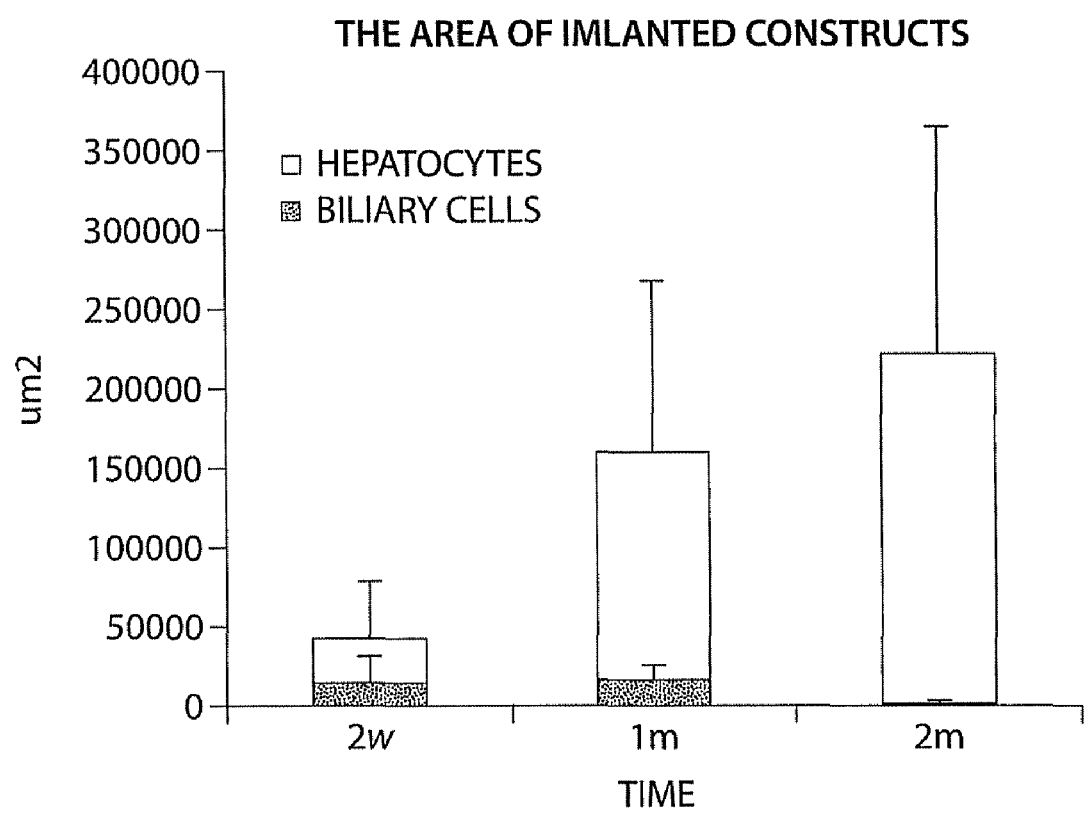
FIG. 19 shows the area occupied by implanted constructs (μg$^2$/section). Total area and bile ducts area are expressed as mean±SD.
Figure 20:
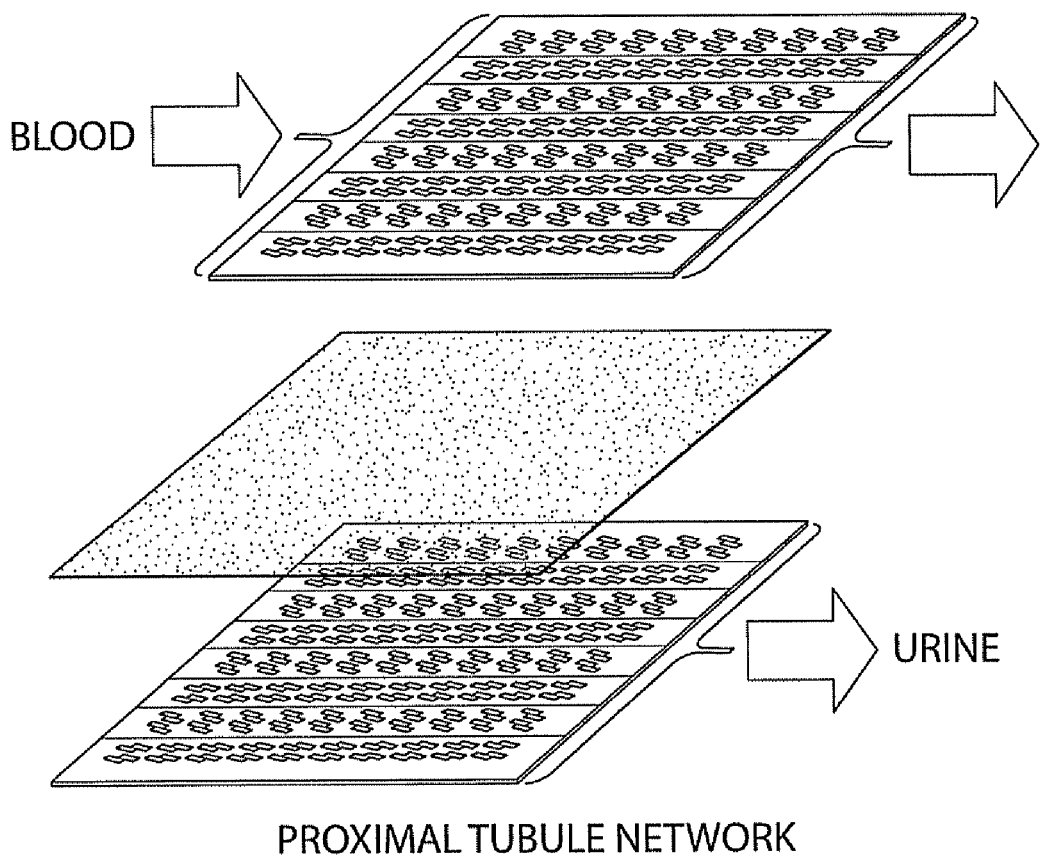
FIG. 20 shows a schematic diagram of a micromachined apparatus for tissue engineered renal replacement. The apparatus comprises a compartment with a glomerular endothelial filter for circulatory flow (42), a semi-permeable membrane for mass transfer of oxygen, nutrients and waste (44), and a compartment with a proximal tubule network excretory system, which includes inlets for filtration of urine (46).
Figure 21:
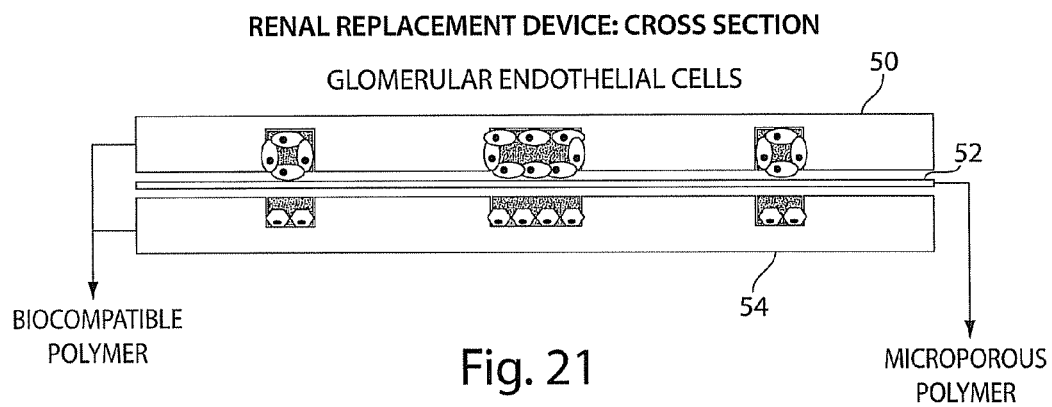
FIG. 21 shows a cross section of a micromachined apparatus for tissue engineered renal replacement. The apparatus comprises a compartment with a glomerular endothelial filter for circulatory flow, a semi-permeable membrane for mass transfer of oxygen, nutrients and waste, and a compartment with a proximal tubule network excretory system, which includes inlets for filtration of urine. Each compartmentalized layer of the apparatus comprises a biocompatible polymer and the layers are separated by a semi-permeable membrane comprising a microporous polymer.
Figure 22:
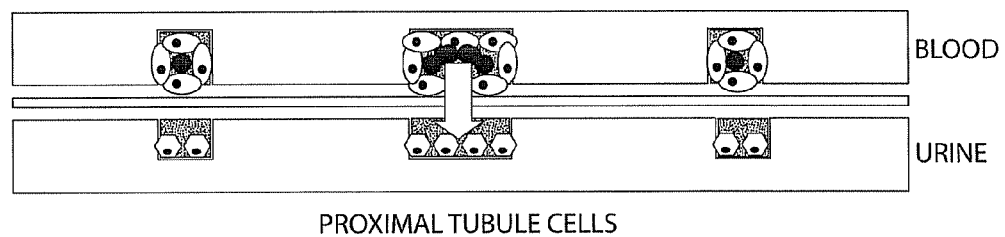
FIG. 22 shows a cross section of a micromachined apparatus for tissue engineered renal replacement. The direction of flow of glomerular ultrafiltrate is shown. Flow originates in the layer comprising glomerular endothelium, passes through the semi-permeable membrane to layer comprising the proximal tubule network where reabsorption occurs.
Figure 23:
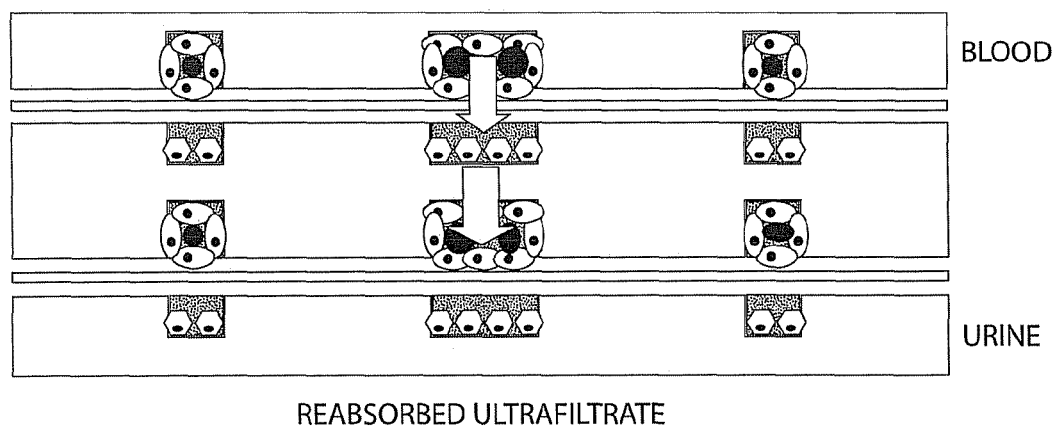
FIG. 23 shows a cross section of a micromachined apparatus for tissue engineered renal replacement comprising multiple stacked layers. The apparatus comprises repeating, stacked units, each unit comprising a compartment with a glomerular endothelial filter for circulatory flow, a semi-permeable membrane for mass transfer of oxygen, nutrients and waste, and a compartment with a proximal tubule network excretory system, which includes inlets for filtration of urine.

The calculated areas occupying implanted constructs were $43136 \pm 36181$, $153810 \pm 106422$, and $224332 \pm 142143$ $\mu m^2$/section at 2 weeks, 1 month, and 2 months, respectively. The mean area increased over time, and there were significant differences between 2 w and 1 m ($p<0.05$), and between 2 w and 2 m ($p<0.01$). No significant difference was observed between 1 m and 2 m. The areas occupied by bile duct-like structures were $13407 \pm 16984$, $15430 \pm 8980$, and $1290 \pm 2052$ $\mu m^2$/section at 2 weeks, 1 month, and 2 months, respectively. The areas were significantly greater at 2 weeks ($p<0.01$) and 1 month ($p<0.05$ by the Mann-Whitney U test), compared to the area at 2 months (FIG. 19).

This Example shows morphologically simple cell sheets created from SHCs and NPCs implanted and engrafted in the omentum. Given adequate hepatotrophic stimulation, implants formed morphologically complex three-dimensional tissue consisting of hepatocytes, structures resembling bile canaliculi, and ducts composed of cells resembling biliary epithelium. These results represent a significant advance toward the tissue engineering of complex vascularized thick tissues.

Example 5

Generation of an Ex Vivo Renal Device

This Example describes a microfabricated network of proximal tubules that could conduct the essential reabsorptive and excretory functions of the kidney ex vivo. (See FIGS. 20-23.) A glomerular endothelial cell-lined network can provide filtration while minimizing thrombosis. These two networks combined on bioresorbable polymer are the basis for an ex vivo tissue engineered renal device.

The design of an ex vivo tissue engineered system can be focused on the development of a glomerular endothelial filter in conjunction with a proximal tubule device for reabsorption and excretion. The endothelial filter is specifically designed to provide physiologic flow with low thrombogenicity and maximized surface area for solute transport. The proximal tubule device, containing an appropriate number of cells for renal replacement, has optimized surface area for solute reabsorption and an outlet for urine excretion (See FIG. 32). Several layers of molds and/or polymer scaffolds and semi-permeable membranes can be stacked to optimize filtration and reabsorption. Biocompatible, bioresorbable and microporous polymers are used throughout for optimal cell growth and function.

Materials and Methods

Configuring the Mold

MEMS replica molding was used to create the polymer molds used in this Example. Using the techniques described herein, an inverse pattern (i.e., protrusions rather than indentations) corresponding to the desired pattern of microchannels was formed on a silicon wafer. Poly-(dimethyl siloxane) (PDMS) was then cast onto the silicon template. After the template was removed, the PDMS was subjected to $O_2$ plasma treatment, and was fastened to a second layer of PDMS. In this Example, the second layer of PDMS was flat, however, in other embodiments, either or both surfaces of the second PDMS layer can contain a pattern of microchannels. In addition, a semi-permeable membrane can be fastened between the PDMS layers.

Cell Culture

Renal proximal tubule cells and glomerular endothelial cells from rat and pig models have been isolated using sieve filtration and separation over a Percoll gradient (Vinay, et al. Am J Physiol 241, F403 (1981); Misra, et al. *Am J Clin Path* 58, 135 (1972)). Human microvascular endothelial cells were isolated from normal neonatal foreskin in collaboration with Dr. Michael Detmar (Cutaneous Biology Research Center, MGH Charletown), and stained positively for endothelial cell markers CD-31 and von Willebrand's factor (vWF) within the PDMS devices.

Both renal proximal tubule cells and human microvascular endothelial cells were seeded into the MEMS-designed PDMS (poly(dimethyl siloxane)) devices at 20 million cells/ml. Cells were allowed to adhere at 37° C. for six hours. Devices were rotated 180 degrees at three hours to allow adherence of cells to both sides of the microchannels. Flow was then started via infusion pump with appropriate culture medium to maintain cell viability.

Results

Figure 24:
FIG. 24 shows human microvascular cells at 14 days after seeding in microchannels.

Human microvascular endothelial cells were seeded into poly(dimethyl siloxane) (PDMS) microchannels (smallest channel width 30 μm, depth 35 μm) using the specifically designed MEMS templates, and good cell adherence and proliferation within the channels was observed (FIG. 24).

A computational model is used to maximize blood flow through the glomerular cell filter, within normal hemodynamic parameters. Finite Element Modeling (FEM) technologies are used to maximize the surface area for filtration to simulate mass transport of solutes across the filter. The template topography and branching angles are designed to minimize thrombosis within the microchannels. Similarly, the proximal tubule network is optimized to provide even flow distribution, surface area for reabsorption, and an outflow tract for excretion of urine.

Cultured proximal tubular cells exhibit characteristic dome formation. Glomerular endothelial cells have also been isolated and maintained in culture. Further characterization of the cells is performed using immunohistochemical staining. Proximal tubule cells are stained for megalin (gp330) expression, and endothelial cells are stained for von Willebrand's factor (vWF) and CD-31.

Function of proximal tubule cells is assessed with the conversion of 1,25-OH-$D_3$ to 1,25-$(OH)_2D_3$ (1,25-dihydroxyvitamin $D_3$), the reclamation of glutathione and the generation of ammonium using a single pass perfusion system. 25-(OH) D3-12-hydroxylase is a cytochrome P-450 monooxygenase found in the inner mitochondrial membrane of proximal tubule cells. Proximal tubule glutathione reclamation is performed by the brush-border enzyme gamma-glutamyl transpeptidase. In addition, specific transport functions such as vectoral fluid transport (inhibited by ouabain, an $Na^+$—$K^+$-ATPase inhibitor), active bicarbonate and glucose transport (inhibited by acetazolamide and phlorizin respectively), and para-aminohippurate secretion (inhibited by probenecid) are also tested (Humes, et al., *Kid Int* 55, 2502 (1999); Humes, et al. *Nat Biotechnol* 17, 451 (1999)). Glomerular endothelial cell function is assessed for permeability to water and serum proteins, and the basement membrane components analyzed.

Figure 25:
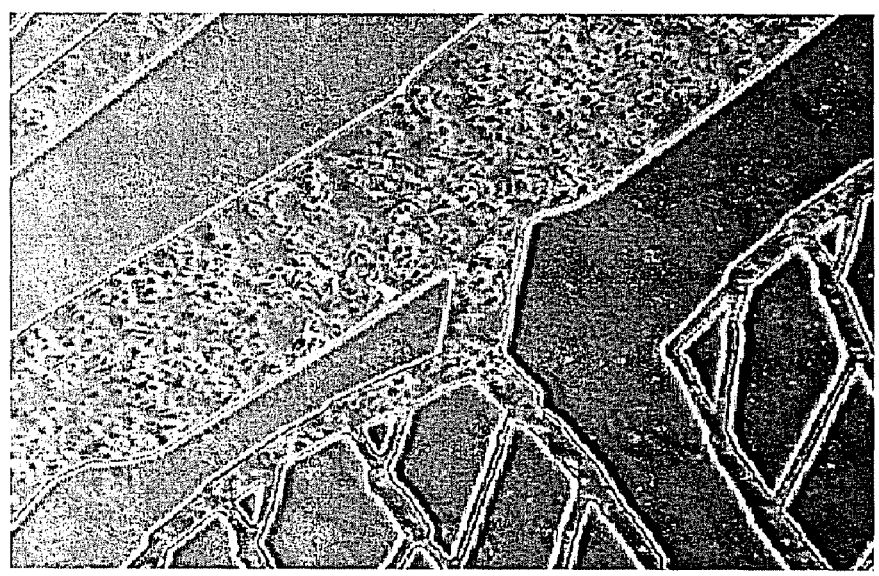
FIG. 25 shows proximal tubule cells growing in a poly dimethyl-siloxane (PDMS) polymer scaffold at approximately 5 hours after seeding.
Figure 26:
FIG. 26 shows proximal tubule cells growing in a poly dimethyl-siloxane (PDMS) polymer scaffold at 2 days after seeding.
Figure 27:
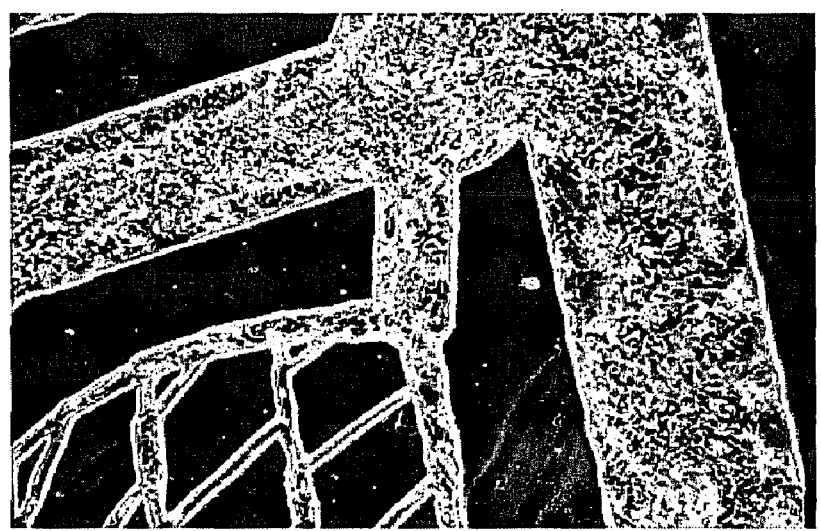
FIG. 27 shows proximal tubule cells growing in a poly dimethyl-siloxane (PDMS) polymer scaffold at 6 days after seeding.

Microvascular endothelial and proximal tubule cells into have been successfully seeded into PDMS networks made from MEMS templates. FIGS. 25-27 show proximal tubule cells growing in the microchannels of the polymer scaffold at various intervals after seeding.

Example 6

Drug Metabolism in Three-Dimensional Liver Tissue Engineered Systems

Generation of Vascular and Hepatic Tissues on Microfabricated Substrates

Figure 43A:
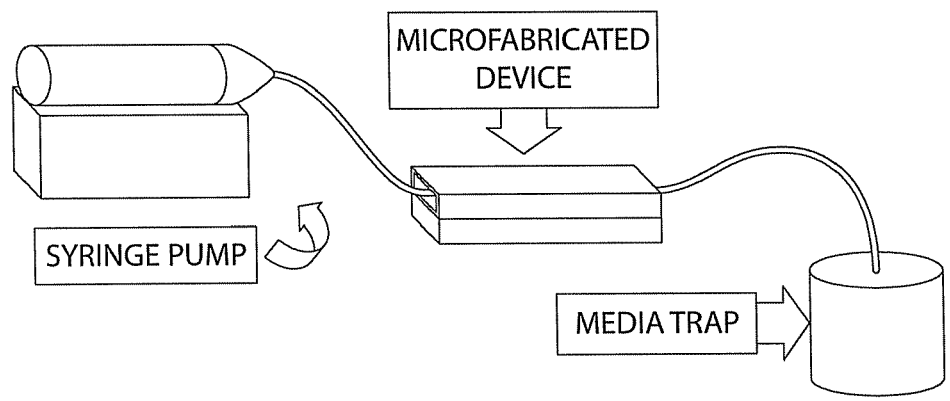
FIG. 43a depicts a single-pass flow microfabricated device set up.
Figure 43B:
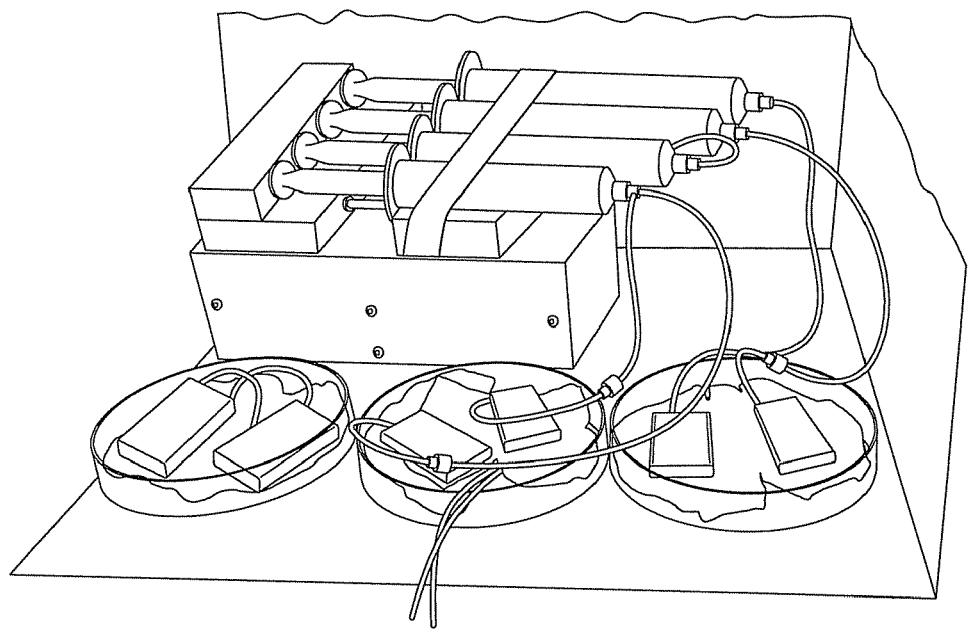
FIG. 43b depicts microfabricated devices with Hep G2/C3a connected to syringe pumps.
Figure 44A:
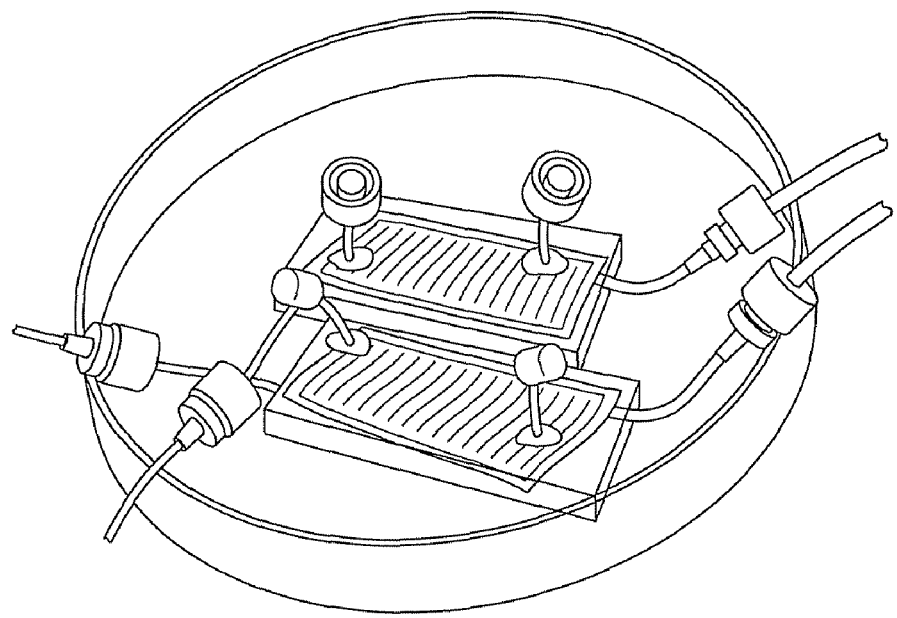
FIG. 44a depicts a picture of a microfabricated device containing Hep G2/C3 cells.

HepG2/C3a cells were suspended in modified Eagle's medium α (MEMα), supplemented with 10% fetal bovine serum (no other supplements were added). The cells were seeded into the parenchymal chamber of a microfabricated device at 2 million cells per ml, or 0.5 million cells per device. The opposite side of the chamber comprised the engineered vascular tissue. Cultures were maintained at 37° C. FIG. 43A depicts a schematic of the single-pass flow microfabricated device and the photographs of FIGS. 43B and 44A show HepG2/C3a cells seeded into the device. This single-pass flow microfabricated polydimethylsiloxane ("PDMS") device allows for fresh media to pass through the vasculature channels, allowing for nutrient, waste and gas exchange to occur through a polycarbonate membrane ("PC") separating the parenchymal chamber. To initialize the device prior to cell seeding, a 30 mL syringe was filled with media and placed on a Harvard Apparatus PHD 2000 Infusion pump. The syringe was connected by luer locks to silastic tubing, which connects to the inlet of the microvascular side on the device. The outlet of the microfabricated channels were connected to another length of silastic tubing that is connected to a 22-gauge needle. The needle was inserted into a bug stopper and bottle where effluent media was collected.

Figure 44B:
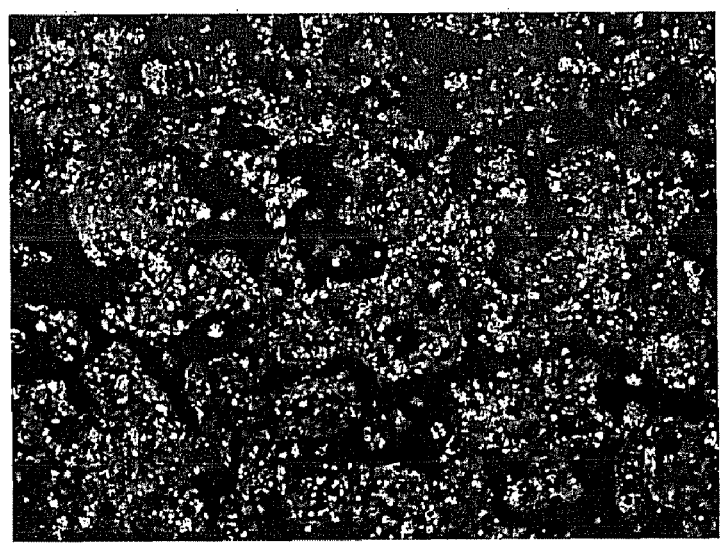
FIG. 44b depicts a picture of Hep G2/C3a cells in tissue culture flask stained with Live/Dead assay demonstrating appearance of healthy Hep G2/C3a under normal culture conditions.
Figure 45A:
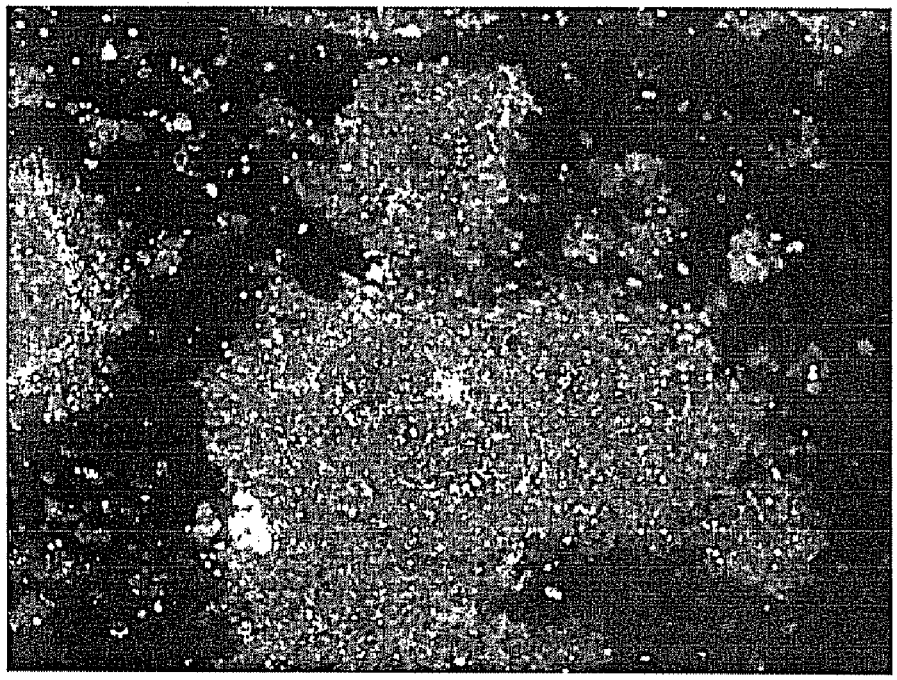
FIG. 45 depicts Hep G2/C3a cells in a microfabricated device after 2 weeks incubation and stained with Live/Dead stain (Molecular Probes).
Figure 45B:
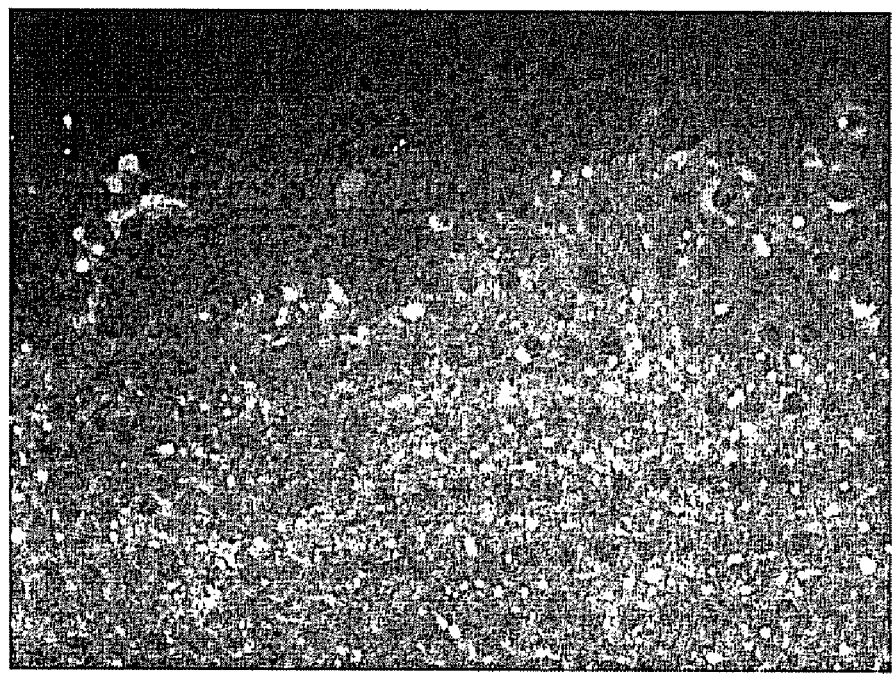

HepG2/C3a cell viability was determined using the LIVE/DEAD® stain (Molecular Probes, Eugene, Oreg.). FIG. 44B shows the appearance of healthy hepatocytes under normal culture conditions. These viability assays have been carried out to two weeks to demonstrate HepG2/C3a survival in the MEMS system (FIG. 45).

DNA Content of Human Hepatocyte Cells

HepG2/C3a cells were assayed for DNA content after growth in the microfabricated device for a total of 10 days. The DNA levels of HepG2/C3a cells increased up to day 10. The DNA levels were determined using the Dneasy Kit from Qiagen at day 1, 3, 5, 7, and 10. The cells were lysed in the parenchymal chamber of the device using 200 μL of PBS, 20 μL of Proteinase K, and 200 μL Buffer AL while placed in a 70° C. water bath. After 10 minutes the devices were removed and 200 μL of 200 proof ethanol was added. The solution was then flushed into spin columns and centrifuged for 1 minute at 8,000 RPM. The collection tube was discarded, 500 μL of Buffer AW1 was added to the column, and then centrifuged for 1 minute at 8,000 RPM. Again the collection tube was discarded, 500 μL of Buffer AW2 was added to the column, and then centrifuged for 3 minutes at full speed. The column was placed in a clean microcentrifuge tube and 200 μL of Buffer AE was pipeted onto the membrane. The column was incubated at room temperature for one minute and centrifuged at 8,000 RPM. The resulting elutant was analyzed for DNA content using ultra violet spectrophotometry at wavelengths 260 nm and 280 nm. DNA standard regression curves were compiled using the same protocol and known number of HepG2/C3a cells.

Liver Cell Function

Liver function was assessed by measuring the production of albumin, alphafetoprotein and transferrin by ELISA. Serum-free Hepatocyte Maintenance Media ("HMM") was recovered from the device on day 1, 3, 5, 7 and 10. At each time point, 100 μl was taken and analyzed for the presence of the liver markers by Enzyme-Linked Immunosorbent Assay (ELISA). The ELISA was performed in a 96 well plate coated with 100 μL of 11.2 μg/mL of unconjugated Rabbit anti-human Albumin by Dako diluted in a bicarbonate buffer coating solution (0.159 g Sodium Carbonate Anhydrous, 0.0293 g Sodium Bicarbonate, 0.02 g Sodium Azide, 100 mL distilled water, pH 9.6) and refrigerated overnight. The plates were washed three times using PBS-Tween (16 g NaCl, 0.04 g Na $H_2PO_4$ monobasic, 2.82 g $NaH_2PO_4$ sodium monobasic, 0.4 g KCl, 1 mL Polyoxy Ethylene Sorbitan, 2 L Distilled Water, pH 7.4) and blocked with 200 μL 1% Gelatin Blocking Solution in PBS-Tween. Beginning with 200 μL, eight serial dilutions decreasing the concentration by half, but keeping a total of 200 μL were made of both the bioreactor sample and the standard 25 ηg/mL Human Albumin (Pierce). The plate was incubated for one hour and then washed three times with PBS-Tween. The prepared conjugated antibody was Dako rabbit anti-human Albumin conjugated to HRP. 50 μL of the stock conjugated antibody was diluted into 950 μL of PBS-Tween. 900 μL of the resulting solution was diluted into 22 mL of PBS-Tween; 100 μL of this solution was added to each well and incubated at 37° C. for one hour. The wells were washed three times with PBS-Tween and 100 μL of substrate solution was added to each well. The absorbance was measured at 405 ηm in a Wallac Victor$^2$ 1420 MultiLabel Counter plate reader. The absorbance was recorded and the measurement of albumin synthesis was calculated in mcg/dL of media.

ELISA kits for human alphafetoprotein, AFP ELISA Kit (catalog #0500-AFP), were purchased from Alpha Diagnostic (San Antonio, Tex.). Protocol was followed per Alpha Diagnositc Lab's instructions. In brief, 96 well strip plates were supplied by Alpha Diagnostic labs, which were pre-coated with primary antibody and ready-to use. One hundred microliter of samples were then placed into each well of the first row for serial dilution and in duplicates. They were incubated at room temperature for 30 minutes before washing 5 times with tap water. One hundred microliter of secondary antibody linked to HRP enzyme conjugate was then applied for 30 minutes at room temperature and washed 5 times with tap water. Finally, HRP-substrate solution was applied and allowed to react for 10 minutes in the dark at room temperature before applying 50 µl of stop solution. All plates were read by the Wallac Victor$^2$ 1420 MultiLabel Counter plate reader at 450 nm.

ELISA kit for human transferrin (catalog #E80-129) was purchased from Bethyl Labs (Montgomery, Tex.). Protocol per Bethyl Labs was followed. In brief, primary anti-human transferring antibody supplied by Bethyl Labs was used to coat 96 well plates (Nunc) for 60 minutes, washed 3 times with wash solution, blocked for 30 minutes with blocking solution, and washed again for 3 times. After this, the plate was used for standards and sample testing. One hundred microliter of sample or standard was placed in each well in duplicates and for serial dilution. As per protocol a 1:100,000 dilution of the HRP conjugate and diluent was placed in each well and allowed to incubate for 60 minutes. After the incubation step, the wells were washed 5 times. One hundred microliter of TMB ELISA solution was placed into each well and allowed to react for 30 minutes after which Stop Solution [2M $H_2SO_4$] was added to each well. The plate was then read by the Wallac Victor$^2$ 1420 MultiLabel Counter plate reader at 450 nm.

Metabolism of 7-ethoxycoumarin

The hepatocyte culture medium was changed from MEMα to Hepatocyte Maintenance Medium (Clonetics™), which comprised 50 UL of Dexamethasone (0.5 mL), 57 UL Insulin, Bovine (0.5 mL), and 0.5 mL Gentamicin Sulphate Amphotericin-B (0.5 mL) (Single Quots® by Clonetics™). Hepatocyte maintenance medium (HMM) does not contain serum. For the purposes of measuring metabolic function of the hepatocyte cell cultures, the hepatocyte culture medium was additionally supplemented with 35 µM 7-ethoxycoumarin (ECOD). The ECOD/HMM was allowed to perfuse through the device for 48 hours.

The HMM was not only assayed for the presence of liver cell markers, but also ECOD and its metabolites. A Supelcosil LC-8 high performance liquid chromatography (HPLC) column (5 µm; 5×0.46 cm) was used to detect ECOD and breakdown products thereof. The flow rate was set at 1 ml/min, and the products detected in the ultraviolet range, at 325 nm. The total run time was 20 minutes, using a two-solvent gradient. Solvent A was comprised of 5 ml 1M tetrabutyl ammonium dihydrogen phosphate (TBAP), 2.25 ml glacial acetic acid, 900 ml of deionized water, and HPLC-grade acetonitrile to a final volume of 1000 ml. The solution was adjusted to pH 4.7 using NaOH. Solvent B comprised 5 ml of 1M TBAP, 1.25 ml glacial acetic acid, 500 ml water, and acetonitrile to a final volume of 1000 ml. Solvent B was adjusted to pH 4.7 using NaOH. Table 1 presents the percentage of each solvent present in the gradient, correlating to the run time of the HPLC program.

TABLE 1

| Time | Percentage of Solvent | |
|---|---|---|
| (minutes) | Solvent A | Solvent B |
| 0 | 90 | 10 |
| 4 | 90 | 10 |
| 12 | 50 | 50 |
| 12.5 | 90 | 10 |
| 15 | 90 | 10 |

Four standards were used: 7-ethoxycoumarin, which was prepared as 1 mg/ml solution in methanol, and 10 µg/ml solutions prepared from the 1 mg/ml solutions in distilled water; the Phase I metabolite of ECOD, 7-hydroxycoumarin (7-HC), which was prepared as a 1 mg/ml solution in 50:50 methanol:water, and 10 µg/ml solutions diluted in distilled water; the Phase II metabolite, 7-HC-glucuronide, which was prepared as a 1 mg/ml solution in 50:50 methanol:water, and subsequently diluted in distilled water to yield a 10 µg/ml solution; and 7-HC-sulphate, prepared as a 1 mg/ml solution in 50:50 methanol:water, and subsequently diluted in distilled water to yield a 10 µg/ml solution. ECOD elutes between 12.919 to 14.647 minutes from the column, while 7-HC elutes at 3.709 to 4.668 minutes. The subsequent breakdown product, 7HC-glucuronide, is retained at 2.265 to 3.947 minutes, and 7HC-sulphate is retained from 10.230 to 12.878 minutes.

Figure 46:
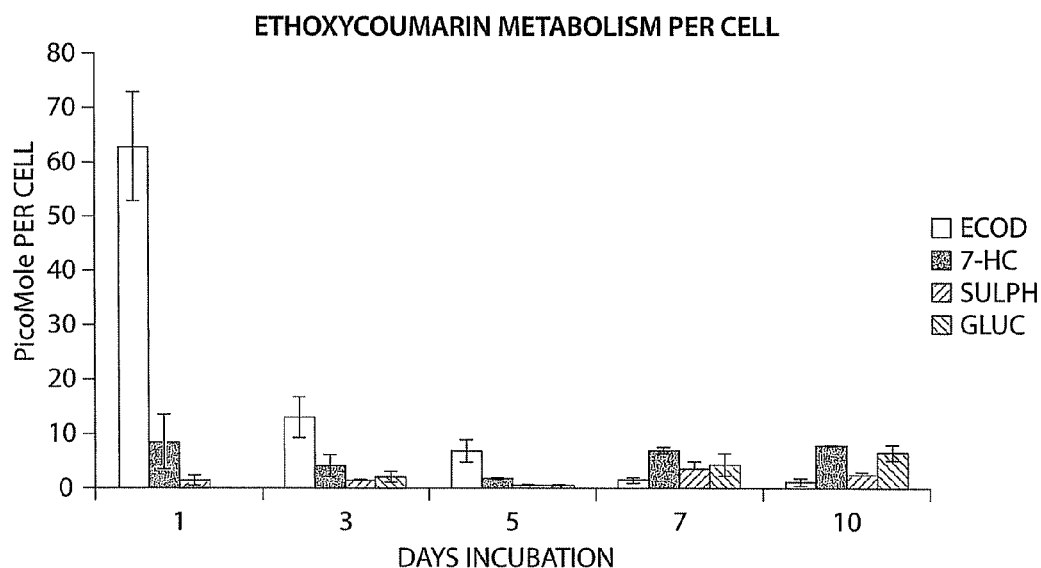
FIG. 46 is a graph demonstrating the amount of ECOD and its subsequent breakdown products in picomoles per cell after 1, 3, 5, 7, and 10 days of incubation in the microfabricated device.
Figure 47:
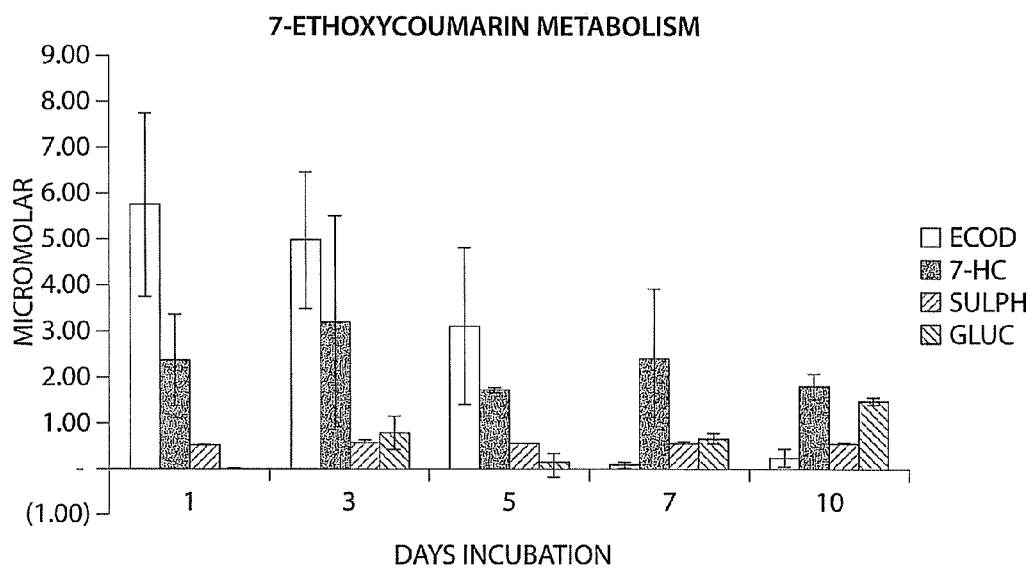
Figure 48:
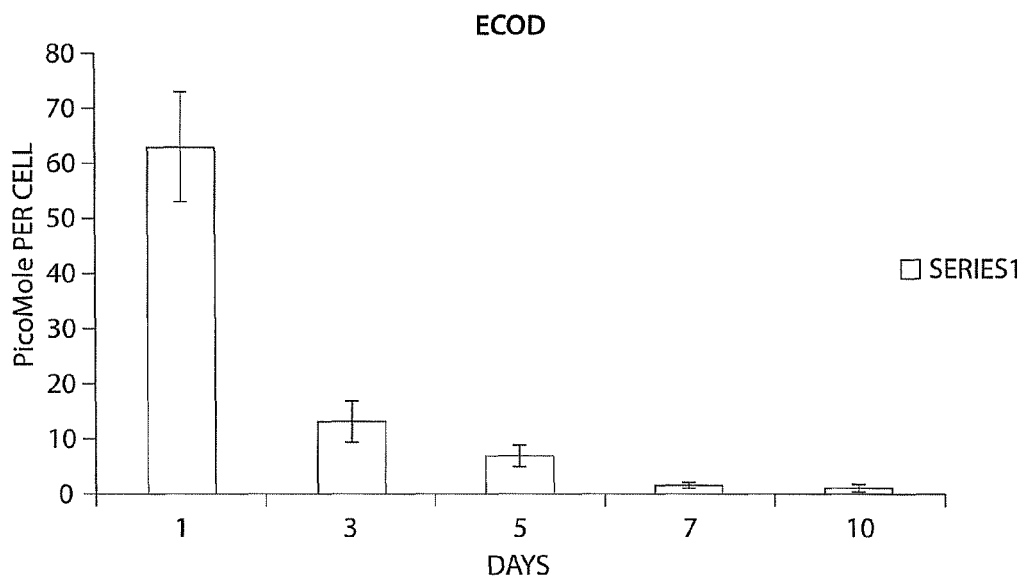
FIGS. 48-51 depict graphs showing each individual metabolite alone on the same time scale.
Figure 49:
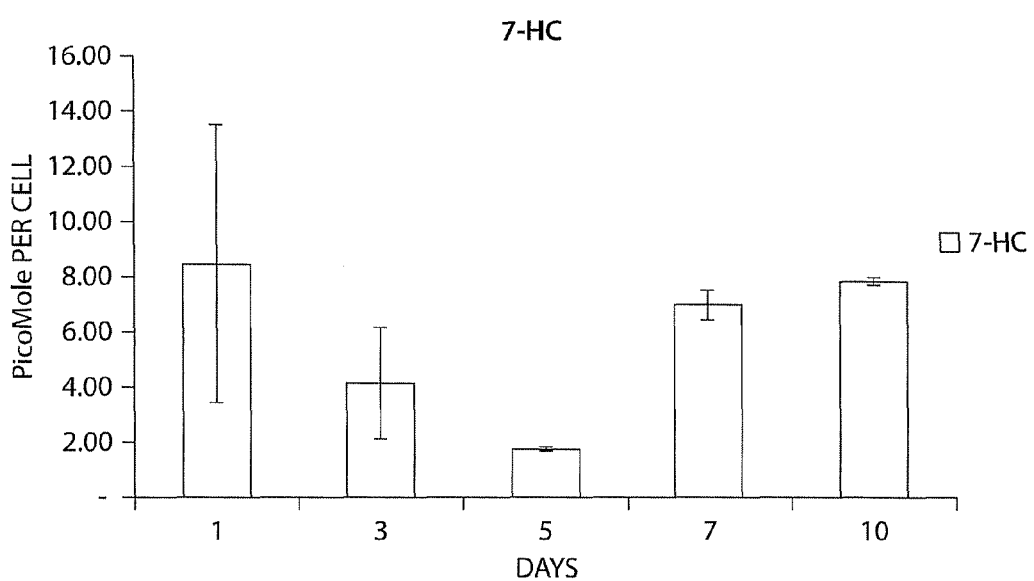
Figure 50:
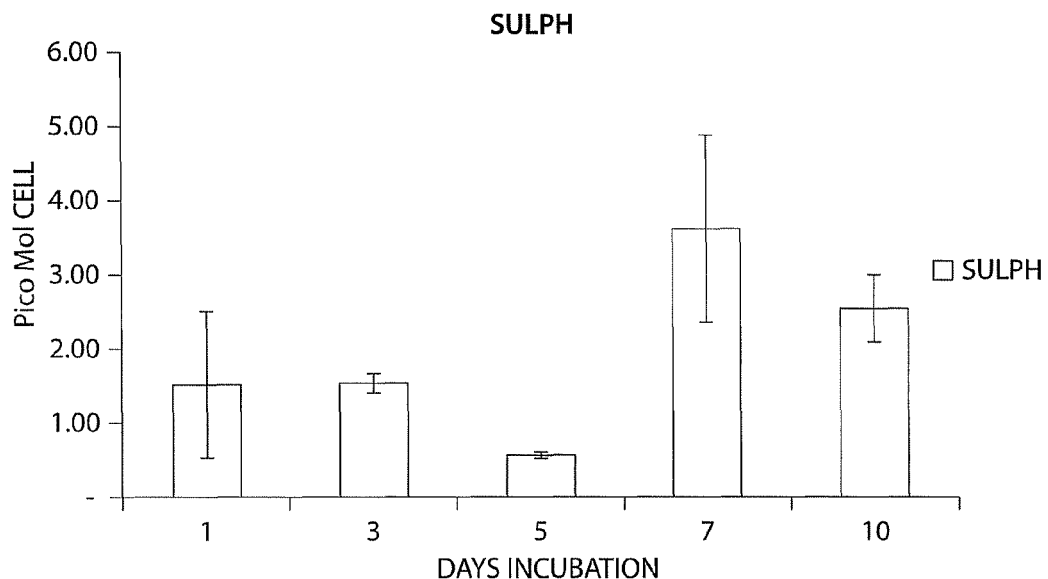
Figure 51:
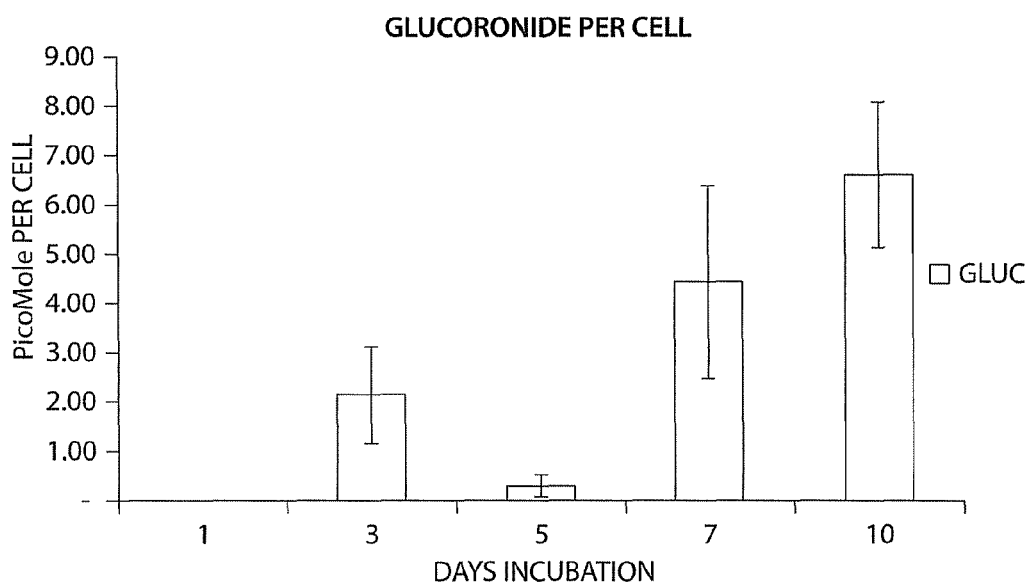

FIG. 46 depicts a graph of the amount of ECOD and its subsequent breakdown products in picomoles per cell after 1, 3, 5, 7, and 10 days of incubation in the microfabricated device. A related graph shown in FIG. 47 depicts the same data in terms of total micromoles of ECOD or its metabolites (FIG. 46 depicts the metabolism on a cellular basis and FIG. 47 depicts the metabolism occurring in the device as a whole). FIGS. 48-51 depict graphs showing each individual metabolite alone on the same time scale.

The results indicate that three-dimensional liver tissue engineered systems metabolize drugs that use Phase I and Phase II cytochrome P450 (CYP450) pathways.

* * *

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

The invention claimed:

1. A method for detecting one or more metabolites of a test agent in a tissue comprising:
   A) incubating a test agent and an enzyme within a three-dimensional structure comprising a first mold or polymer scaffold, a semi-permeable membrane, and a second mold or polymer scaffold, wherein the semi-permeable membrane is disposed between the first and second molds or polymer scaffolds, and wherein the first mold or polymer scaffold has microchannels that form a fluidic branching network that mimics the forces and transport of natural vasculatures and wherein the second mold or polymer scaffold comprises cells;

B) forming an enzyme-substrate complex between the enzyme and the test agent; and C) detecting one or more metabolites of the test agent.

2. The method of claim 1, wherein the structure comprises liver tissue, kidney tissue, cardiac tissue, cartilage tissue, or bone marrow tissue, and combinations thereof.

3. The method of claim 1, wherein the test agent comprises a compound selected from the group consisting of opioid analgesics, anti-inflammatory drugs, diuretics, cardiovascular drugs, cardiac drugs, agents that affect hyperlipoproteinemias, anti-neoplastic agents, immunomodulators, anti-diabetic agents, and anti-microbial agents.

4. The method of claim 1, wherein the enzyme is selected from the group consisting of cytochrome P450, alkaline phosphatase, α-galactosidase, β-galactosidase, α-glucosidase, β-glucosidase, α-glucuronidase, β-glucuronidase, α-amylase, NADPH-cytochrome P450 reductase, cytochrome $b_5$, N-demethylase, O-demethylase, acetylcholinesterase, pseudocholinesterase, epoxide hydrolase, amidases, uridine diphosphate (UDP)-glucuronosyltransferases, phenol sulfotransferase, alcohol sulfotransferase, sterid sulfotransferase, and arylamine sulfotransferase, UDP-glycosyltransferases, purine phosphoribosyltransferase, N-acetyltransferases, glutathione S-transferase, phenylethanolamine N-methyltransferase, non-specific N-methyltransferase, imidazole N-methyltransferase, catechol-O-methyltransferase, hydroxyindole-O-methyltransferase, S-methyltransferase, alcohol dehydrogenase, aldehyde dehydrogenase, xanthine oxidase, monoamine oxidases, diamine oxidases, flavoprotein N-oxidases, hydroxylases, aromatases, cysteine conjugate β-lyase, and alkylhydrazine oxidase.

5. The method of claim 1, wherein the enzyme is endogenously expressed in the tissue.

6. The method of claim 1, wherein the enzyme has normal enzymatic activity compared to an enzyme containing a polymorphism or mutation and having altered enzymatic activity.

7. The method of claim 1, wherein the enzyme contains a polymorphism or mutation.

8. The method of claim 1, wherein the enzyme is a recombinant enzyme.

9. The method of claim 1, wherein the enzyme is cytochrome P450.

10. The method of claim 1, wherein the one or more metabolites are detected by liquid chromatography, mass spectrometry, nuclear magnetic resonance, or spectrophotometry.

11. The method of claim 1, wherein the membrane is endothelialized.

12. The method of claim 1, further comprising circulating a physiological fluid through the microchannels, wherein the physiological fluid is selected from the group consisting of media, blood, plasma and combinations thereof.

13. The method of claim 3, wherein the anti-inflammatory drugs are selected from the group consisting of antihistamines and non-steroidal anti-inflammatory drugs (nsaids).

14. The method of claim 3, wherein the diuretics are selected from the group consisting of carbonic anhydrase inhibitors, loop diuretics, high-ceiling diuretics, thiazides and potassium-sparing diuretics.

15. The method of claim 3, wherein the cardiovascular drug is an angiotensin converting enzyme inhibitor.

16. The method of claim 3, wherein the cardiac drugs are selected from the group consisting of organic nitrates, calcium channel blockers, sympatholytic agents, vasodilators, β-adrenergic receptor agonists, β-adrenergic receptor antagonists, cardiac glycosides and anti-arrhythmic drugs.

17. The method of claim 3, wherein the agent that affects hyperlipoproteinemias is a 3-hydroxymethylglutaryl-coenzyme a (hmg-coa) inhibitor.

18. The method of claim 3, wherein the anti-neoplastic agents are selected from the group consisting alkylating agents and antimetabolites.

19. The method of claim 3, wherein the anti-microbial agents are selected from the group consisting antibiotics, antibacterial agents, antiviral agents, antifungal agents, antiprotozoal agents and antihelminthic agents.

* * * * *